United States Patent
Talavera-Adame et al.

(10) Patent No.: US 11,920,160 B2
(45) Date of Patent: Mar. 5, 2024

(54) PANCREATIC INSULIN-PRODUCING BETA-CELL LINES DERIVED FROM HUMAN PLURIPOTENT STEM CELLS

(71) Applicant: Cedars-Sinai Medical Center, Los Angeles, CA (US)

(72) Inventors: Dodanim Talavera-Adame, Canyon Country, CA (US); Donald C. Dafoe, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/769,420

(22) PCT Filed: Feb. 21, 2014

(86) PCT No.: PCT/US2014/017823
§ 371 (c)(1),
(2) Date: Aug. 20, 2015

(87) PCT Pub. No.: WO2014/130887
PCT Pub. Date: Aug. 28, 2014

(65) Prior Publication Data
US 2015/0376574 A1 Dec. 31, 2015

Related U.S. Application Data

(60) Provisional application No. 61/768,197, filed on Feb. 22, 2013.

(51) Int. Cl.
*C12N 5/071* (2010.01)
*A61K 35/39* (2015.01)

(52) U.S. Cl.
CPC ............ *C12N 5/0676* (2013.01); *A61K 35/39* (2013.01); *C12N 5/0677* (2013.01); *C12N 2501/105* (2013.01); *C12N 2501/11* (2013.01); *C12N 2501/117* (2013.01); *C12N 2501/12* (2013.01); *C12N 2501/16* (2013.01); *C12N 2501/30* (2013.01); *C12N 2501/385* (2013.01); *C12N 2501/40* (2013.01); *C12N 2501/415* (2013.01); *C12N 2501/999* (2013.01); *C12N 2502/28* (2013.01); *C12N 2506/02* (2013.01); *C12N 2506/45* (2013.01); *C12N 2533/90* (2013.01)

(58) Field of Classification Search
CPC .............. C12N 5/0677; C12N 2533/90; C12N 2501/117; C12N 2501/16; C12N 2501/385; C12N 2501/415; C12N 2502/28; C12N 2506/02; C12N 2506/45; C12N 2501/12; C12N 2501/11; C12N 5/0676; C12N 2501/999; C12N 2501/40; C12N 2501/30; C12N 2501/105; A61K 35/39; A61K 2300/00; A61K 35/12; A61K 38/22; A61K 38/30; A61K 35/545
See application file for complete search history.

(56) References Cited

U.S. PATENT DOCUMENTS

2015/0159139 A1* 6/2015 Rezania ................ C12N 5/067
424/93.7
2021/0000880 A1 1/2021 Svendsen et al.

FOREIGN PATENT DOCUMENTS

WO 2014130887 A1 8/2014
WO 2019/183597 A1 9/2019

OTHER PUBLICATIONS

Talavera-Adame Stem cell Rec. 2011, 7, 532-543.*
Xu Mech Dev. Sep. 2011; 128(7-10): 412-427, 1-26.*
Jaramillo and Banerjee et al (J Vis Exp. 2012; (61): e3759, 1-6.*
Kleinman et al (Seminars in Cancer Biology 15 (2005) 378-386.*
Lock et al Tissue Engineering, 2007, 13, 7, 1399-1412.*
Zhang et al Cell Research 2009, 19:429-438.*
Banerjee et al Journal of Tissue Engineering and Reg. Medicine, 2010, 1-6.*
Van Hoof et al Stem cell Research, 2011, 6, 276-285.*
Nikolova et al Dev. Cell 10, 397-405.*
Fujikawa et al (American Journal of Pathology, 2005, 166, 1781-1791.*
Nikolova et al TRENDS in Cell Biology 2007, vol. 17 No. 1, 19-25.*
Weber et al Tissue Engineering, 14, 12, 1959-1568 (Year: 2008).*
Mathew et al. BMC Systems Biology 2012, 6:154, 1-13 (Year: 2012).*
D'Amore Nature Biotechnology,24, 1392- 1401 (Year: 2006).*
Blum et al Nature Biotech, 30, 261-264 (Year: 2012).*
Li et al Endocrinology 144(7):3216-3224) (Year: 2003).*
Pounce et al Cir. Res. 84, 688-694 (Year: 1999).*
Zhu et al Diabetologia 54:2325-2336 (Year: 2011).*

(Continued)

*Primary Examiner* — Anoop K Singh
(74) *Attorney, Agent, or Firm* — Nixon Peabody LLP; Linda B. Huber; Suwei Zhu

(57) ABSTRACT

Production of beta-cells from stem cells from pluripotent stem cells have always been significantly lacking in at least one of the following properties: 1) functional properties related to insulin-production and glucose signaling response, 2) mature phenotype such as biochemical markers or cell structures, 3) efficiency in production of differentiated cells. Described herein is multistep differentiation protocol which substantially overcomes all of the existing limitations. Pluripotent stem cells, including induced pluripotent stem cells (iPSCs), and embryonic stem cells (ESCs) can be differentiated using an embryoid body (EB) formation step, followed by B maturation via endothelial cells (EC) co-culturing and incubation with a sequential series of bone morphogenic protein (BMP)-related growth factor cocktails. The resulting cells displayed functional properties, including insulin-production and glucose signaling response, and mature phenotype of C-peptide expression.

7 Claims, 32 Drawing Sheets

Specification includes a Sequence Listing.

(56) References Cited

OTHER PUBLICATIONS

Talavera, D Molecular Biology of the Cell, vol. 22, No. 24. Abstract No. 2069 (Year: 2011).*
Talavera et al American Journal of Transplantation, vol. 11, Supp. SUPPL. 2, pp. 245. Abstract No. 717 (Year: 2011).*
Talavera et al American Journal of Transplantation, vol. 11, Supp. SUPPL. 2, pp. 245. Abstract No. 717, pp. 1-2 (Year: 2011).*
Nostro et al.Development 138, 861-871 (Year: 2011).*
Domogatskaya, A et al Annu. Rev. Cell Dev. Biol. 28, 523-553 (Year: 2012).*
Yap et al Trends in Cell Biology, December vol. 29, No. 12, , 987-1000 (Year: 2019).*
Keller et al Gene & Development, 19, 1129-1155 (Year: 2005).*
Baiu et al. Potential Pathways to Restore β-Cell Mass: Pluripotent Stem Cells, Reprogramming, and Endogenous Regeneration. Curr Diab Res (2011). 11(5):392-401.
Banerjee et al. Impact of co-culture on pancreatic differentiation of embryonicstem cells. J Tissue Eng Regen Med (2011). 5(4):313-323. Abstract Only.
Jaramillo et al. Endothelial cell co-culture mediates maturation of human embryonic stem cell to pancreatic insulin producing cells in a directed differentiation approach. J Vis Exp (2012). 61: e3759; 6 pages.
Jaramillo et al. Effect of Early Endoderm Induction on Late Stage Pancreatic Maturation of Differentiating Human Embryonic Stem Cells. AIChE Annual Meeting Proceedings (2012); 1 page.
Talavera-Adame et al. Endothelial Cells in Co-culture Enhance Embryonic StemCell Differentiation to Pancreatic Progenitorsand Insulin-Producing Cellsthrough BMP Signaling. Stem Cell Rev and Resp (2011). 7:532-543.
Zhang et al. Highly efficient differentiation of human ES cells and iPS cells into mature pancreatic insulin-producing cells. Cell Res (2009). 19(4):429-438.

International Search Report and Written Opinion for International application No. PCT/US2014/017823 dated May 20, 2014.
Takahisa Fujikawa et al., "Teratoma Formation Leads to Failure of Treatment for Type I Diabetes Using Embryonic Stem Cell-Derived Insulin-Producing Cells," American Journal of Pathology, Jun. 2005, pp. 1781-1791, vol. 166, No. 6, Department of Pathology, University of Florida, Gainesville, Florida, USA.
Dodanim Talavera-Adame et al., "Endothelial Cells in Co-culture Enhance Embryonic Stem Cell Differentiation to Pancreatic Progenitors and Insulin-Producing Cells through BMP Signaling," Stem Cell Rev and Rep, Sep. 2011, pp. 532-543, vol. 7, No. 3.
Lye T. Lock et al., "Stem/Progenitor Cell Sources of Insulin-Producing Cells for the Treatment of Diabetes," Tissue Engineering, Jul. 2007, pp. 1399-1412, vol. 13, No. 7, Department of Chemical and Biological Engineering, State University of New York at Buffalo, Buffalo, New York. USA.
Talavera et al., In Vitro Expansion and Characterization of Insulin-Producing Cells Derived From Human Pluripotent Stem Cells Co-Cultured With Endothelial Cells, poster at Stem Cell Summit, Convention Center, West Palm Beach Florida, USA, 2012.
Talavera-Adame et al., Effective endothelial cell and human pluripotent stem cell interactions generate functional insulin-producing beta cells, 2016, Diabetologia vol. 59, pp. 2378-2386.
Meulen et al., Urocortin 3 Marks Mature Human Primary and Embryonic Stem Cell-Derivced Pancreatic Alpha and Beta Cells, PLOS ONE, 2012, vol. 7(12), pp. 1-12.
Meulen et al., Urocortin 3 Marks Mature Human Primary and Embryonic Stem Cell-Derivced Pancreatic Alpha and Beta Cells, PLOS ONE, 2012, vol. 7(12), Abstract Only.
Jaggupilli et al., Significance of CD44 and CD24 as Cancer Stem Cell Markers: An Enduring Ambiguity, Clinical and Developmental Immunology, 2012, pp. 1-11.
Urocortin 3 as a sensitive marker for beta cell function, Network for Pancreatic Organ Donors with Diabetes, 2022.

* cited by examiner

Collagen I, IV
Laminin I (a)

(b)

B.

A.

A.

B.

PANCREATIC INSULIN-PRODUCING BETA-CELL LINES DERIVED FROM HUMAN PLURIPOTENT STEM CELLS

CROSS-REFERENCE TO OTHER APPLICATIONS

This application is a National Phase of International Application No. PCT/US2014/017823, filed Feb. 21, 2014, which designated the U.S. and that International Application was published under PCT Article 21(2) in English. This application includes a claim of priority under 35 U.S.C. §119(e) to U.S. provisional patent application No. 61/768,197, filed Feb. 22, 2013.

FIELD OF THE INVENTION

The claimed invention relates to regenerative medicine applications by providing variable approaches for cellular differ enation techniques to generate transplantable cellular materials.

BACKGROUND

As it is predicted that the number of diabetic people will increase to 440 million by 2030, there have been a myriad of efforts to obtain these cells in vitro. However, the derivation and propagation of fully-differentiated insulin-producing beta-cells from human embryonic stem cells (hESCs) or human induced pluripotent stem cells (hiPSCs) has proven to be difficult. While others have managed to produce beta-cells from stem cells in the past, the cells described in prior reports have been significantly lacking in at least one of the following properties: 1) functional properties related to insulin-production and glucose signaling response, 2) mature phenotype such as biochemical markers or cell structures, 3) efficiency in production of differentiated cells.

Apparently, complex signals present in the pancreatic niche are necessary to derive these cells in vitro. Since one of the major components of the pancreatic niche is endothelial cells, then signals from these cells may be crucial for full differentiation of insulin-producing beta-cells in vivo. Pancreatic endocrine precursors have been generated in vitro after ESCs treatment with growth factors involved in neural and endoderm differentiation. However, only small numbers of immature insulin-producing cells have been obtained in vitro. Significant obstacles for therapeutic use are further present considering unsuccessful attempts directed at establishing cell propagation techniques. In other cases, some differentiated cells display little or no response to glucose increase upon transplant. Furthermore, the signals in vivo that promote maturation of these cells after transplantation are still unknown. Therefore, there is a great need in the art for a more complex in vitro microenvironment that permits interaction with other cells, such as endothelial cells, to manipulate and exploit the signals that involved in the complete differentiation and maturation of insulin producing cells derived from pluripotent cells in culture.

Described herein is multistep differentiation protocol which substantially overcomes all of the existing limitations. Pluripotent stem cells, including induced pluripotent stem cells (iPSCs), and embryonic stem cells (ESCs) can be differentiated using an embryoid body (EB) formation step, followed by 20-day EB maturation via endothelial cells (EC) co-culturing and incubation with a bone morphogenic protein (BMP)-related growth factor cocktail. The resulting cells displayed functional properties, including insulin-production and glucose signaling response, and mature phenotype of C-peptide expression. Up to ~50, ~75%, and even ~95% of hPSCs can be converted into beta-cells with these functional, mature properties. These results have further been extended to develop a process for directly differentiating pSCs into definitive endoderm. Cells produced by these methods display proper surface marker expression, morphology, and importantly, proper functional output in relevant in vivo physiological environments.

BRIEF DESCRIPTION OF THE FIGURES

Exemplary embodiments are illustrated in referenced figures. It is intended that the embodiments and figures disclosed herein are to be considered illustrative rather than restrictive.

SUMMARY OF THE INVENTION

Figure 1A:
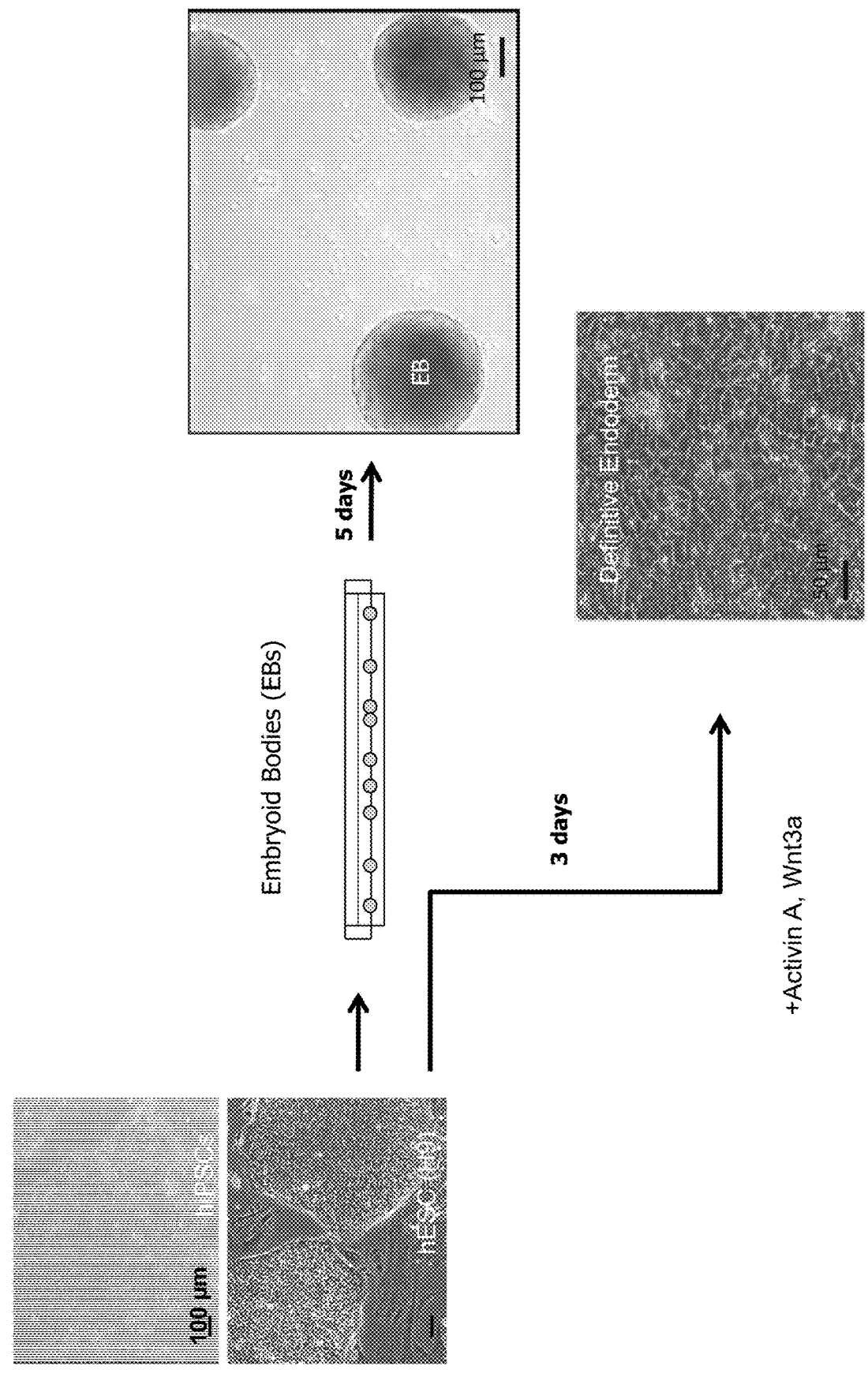
FIGS. 1A-1F. Multi-Step Differentiation Protocol. Both human induced pluripotent stem cells (hiPSCs) and human embryonic stem cells (hESCs) are pluripotent stem cells (pSCs) that can be differentiated into (1A) definitive endoderm following addition of growth factors related to the WNT and Activin pathways, or into embryoid bodies (EBs) (1B) following EB differentiation, cells can be differentiated in a growth factor cocktail with subsequent analysis performed via lentiviral-based fluorescent labeling, or other methods, further including transplant into immunodeficient animals (1C) EBs can be co-cultured in collagen-laminin gel mixtures, an example of which is shown (1D) cells growth in the apparatus of sub-figure (1C) include (1D) endothelial cells (1E) embryoid bodies and (1F) co-cultures of the two cell types.
Figure 1B:
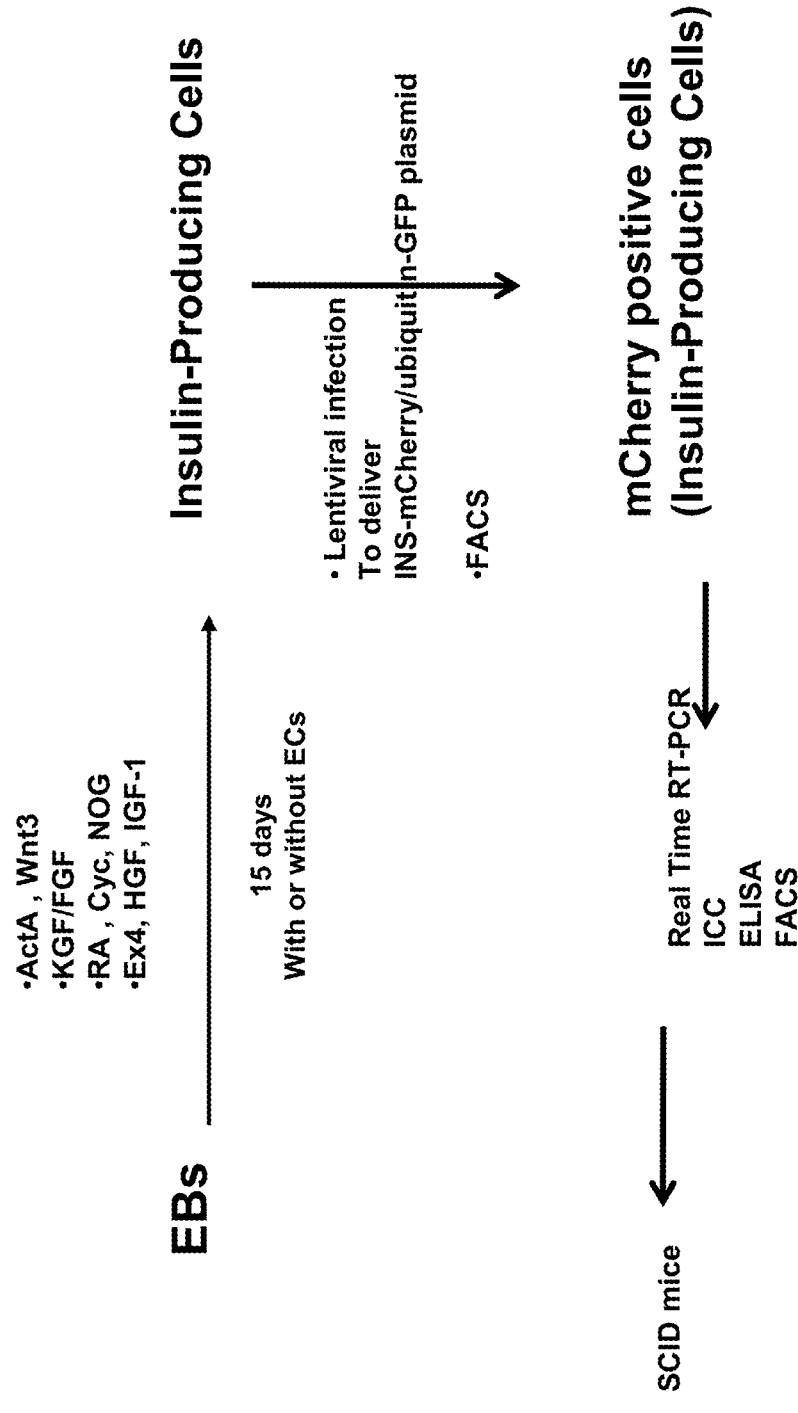
Figure 1F:
Figure 1C:
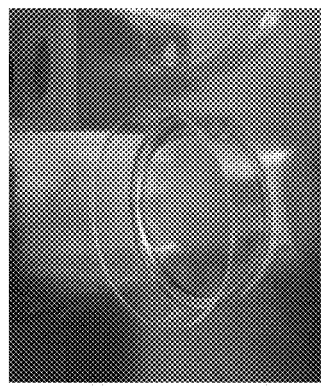
Figure 1E:
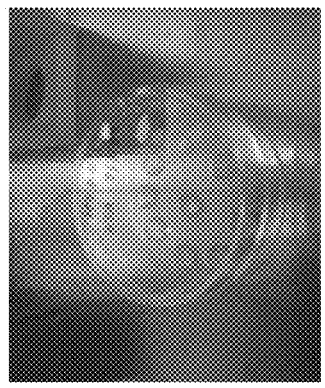
Figure 1E:
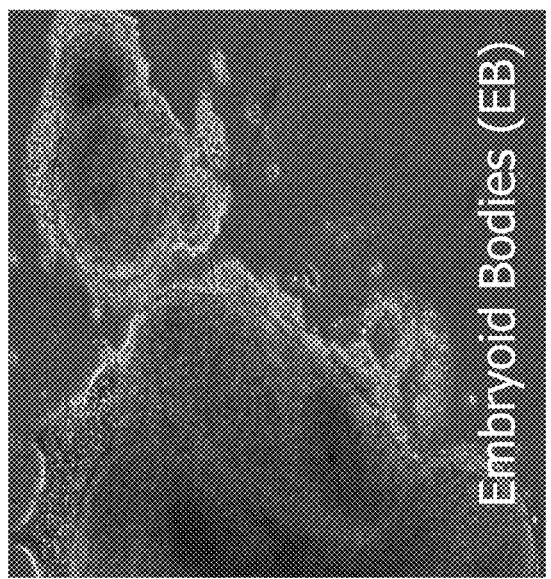
Figure 1D:
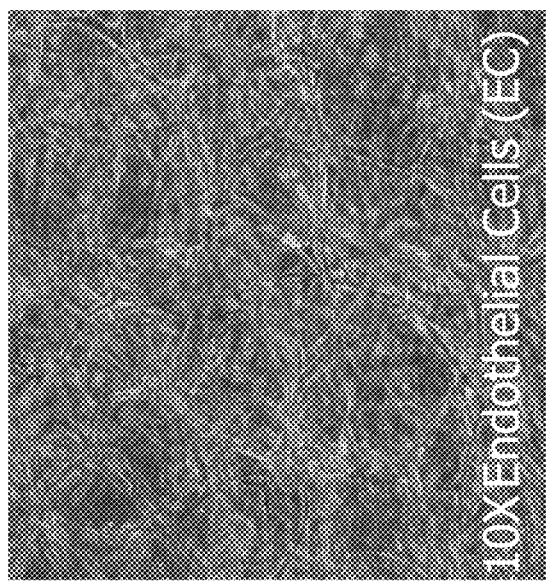

Described herein is a method of differentiating a human pluripotent stem cell into a cell capable of producing insulin including (a) providing a quantity of human pluripotent stem cells (pSCs), and (b) culturing the pSCs in the presence of at least one differentiation agent, and at least one extracellular matrix (ECM) component, wherein the at least one differentiation agent and at least one ECM component are capable of differentiating the pSCs into a cell capable of producing insulin. In other embodiments, culturing the pSCs includes inducing the formation of embryoid bodies (EBs). In other embodiments, the EBs are cultured in the presence of endothelial cells. In other embodiments, the endothelial cells are human microvascular endothelial cells (HMECs). In other embodiments, the at least one first differentiation agent in step (b) includes activin A and wingless-related MMTV integration site 3A (WNT3A). In other embodiments, the cell capable of producing insulin expresses one or more markers selected from the group including proinsulin, insulin, glucagon, somatostatin and PDX-1, and Nkx6.1. In other embodiments, the cell capable of producing insulin is responsive to glucose. In other embodiments, the cell capable of producing insulin secretes insulin C-peptide. In other embodiments, the cell capable of producing insulin can be expanded in vitro. In other embodiments, the cell capable of producing insulin is a pancreatic beta-cell. In other embodiments, the ECM component includes at least one ECM component selected from the following: a collagen, a laminin, an integrin, a fibronectin, a proteoglycan, and an elastin. In other embodiments, the ECM component includes collagen I, IV, and laminin I Also described herein is a cell capable of producing insulin, produced by the described method. Also described herein is a cell line, including one or cells produced by the described method.

Also described herein is a method of differentiating a human pluripotent stem cell into a cell capable of producing insulin including (a) providing a quantity of human pluripotent stem cells (pSCs), and (b) culturing the pSCs in the presence of at least one differentiation agent, and at least one extracellular matrix (ECM) component, wherein the at least one differentiation agent and at least one ECM component are capable of differentiating the pSCs into a cell capable of producing insulin and further including (c) culturing the pSCs in the presence of at least one second differentiation agent including all-trans retinoic acid (RA) and keratinocyte growth factor (KGF) (d) culturing of the pSCs in the presence of at least one third differentiation agent including epidermal growth factor (EGF) and (e) culturing the pSCs in the presence of at least one fourth differentiation agent including hepatocyte growth factor (HGF), insulin-like growth factor (IGF1), exendin-4 and nicotinamide. In other embodiments, the cell capable of producing insulin is a definitive endoderm (DE) cell. In other embodiments, the DE cell expresses CXCR, SOX17, or both. In other embodiments, the cell capable of producing insulin expresses one or more markers selected from the group including proinsulin, insulin, glucagon, somatostatin and PDX-1, and Nkx6.1. In other embodiments, the cell capable of producing insulin is responsive to glucose. In other embodiments, the cell capable of producing insulin secretes insulin C-peptide. In other embodiments, the cell capable of producing insulin can be expanded in vitro. In other embodiments, the cell capable of producing insulin is a pancreatic beta-cell. In other embodiments, the ECM component includes at least one ECM component selected from the following: a collagen, a laminin, an integrin, a fibronectin, a proteoglycan, and an elastin. In other embodiments, the ECM component includes collagen I, IV, and laminin I Also described herein is a cell capable of producing insulin, produced by the described method. Also described herein is a cell line, including one or cells produced by the described method.

Further described herein is a pharmaceutical composition including a pluripotent stem cell (pSC)-derived beta-cell and a pharmaceutically acceptable carrier. In other embodiments, the beta-cell is derived from a pSC according to the method including (a) providing a quantity of human pluripotent stem cells (pSCs), (b) inducing the formation of embryoid bodies (EBs) from the pSCs, (c) culturing the EBs in the presence of at least one differentiation agent including activin A and wingless-related MMTV integration site 3A (WNT3A), at least one extracellular matrix (ECM) component includes a collagen, and a laminin, and a quantity of human microvascular endothelial cells (HMECs), (d) culturing the EBs in the presence of at least one second differentiation agent including all-trans retinoic acid (RA) and keratinocyte growth factor (KGF), (e) culturing of the EBs in the presence of at least one third differentiation agent including epidermal growth factor (EGF), and (f) culturing the EBs in the presence of at least one fourth differentiation agent including hepatocyte growth factor (HGF), insulin-like growth factor (IGF1), exendin-4 and nicotinamide.

Also described herein is a method of modulating diabetic phenotype, including selecting a patient diagnosed with a diabetic phenotype, and administering a quantity of insulin-producing pluripotent stem cell (pSC)-derived cells wherein the pSC-derived cells produce insulin to modulate the diabetic phenotype.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N. Y. 2006); Smith, *March's Advanced Organic Chemistry Reactions, Mechanisms and Structure* 7$^{th}$ ed., J. Wiley & Sons (New York, N. Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N. Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i e, inhibition or suppression) of a response or the two in combination or apart.

"Pharmaceutically acceptable carriers" as used herein refer to conventional pharmaceutically acceptable carriers useful in this invention.

"Promote" and/or "promoting" as used herein refer to an augmentation in a particular behavior of a cell or organism.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

As described, generation of pancreatic beta-cell lines derived from pluripotent stem cells (pSCs) are a potential therapeutic avenue to cover the needs of a diabetic patient's dysfunctional insulin processing of carbohydrates. However, the derivation and propagation of fully-differentiated insulin-producing beta-cells from pSCs, including both human embryonic stem cells (hESCs) or human induced pluripotent stem cells (hiPSCs, has proven to be difficult.

Apparently, complex signals mirroring the processes of the pancreatic niche are necessary to derive these cells in vitro. Since one of the major components of the pancreatic niche is endothelial cells, signals from these cells are crucial for fully differentiation of insulin-producing beta-cells in vivo. Endothelial cells play a key role in the differentiation and maturation of different cell lineages is known that after induction of pancreatic buds by notochord, the cells from the buds interact with aortic endothelial cells and the dorsal vain to complete the formation of the pancreas and pancreatic endocrine cells. It has been further reported that vascular basement membrane components are essential to maintain insulin-gene expression. Thus, the differentiation of beta-cells is completed after adequate signaling from cells that compose the pancreatic niche.

Pancreatic endocrine precursors have been generated in vitro after ESCs treatment with growth factors involved in neural and endoderm differentiation. However, only a low number of immature insulin-producing cells have been obtained in vitro. This result is further compounded by unsuccessful attempts at cell propagation methods. Sometimes, the differentiated cells are unable to produce insulin after transplantation, or at best, a poor response to glucose increase is observed.

Furthermore, the signals in vivo that promote maturation of these cells after transplantation are still unknown. Therefore, a more complex in vitro microenvironment that permits interaction with other cells, such as endothelial cells, is necessary to explore the signals that might be involved in the complete differentiation and maturation of insulin producing cells derived from pluripotent cells in culture.

The inventors have removed these previously onerous barriers by establishing a multistep differentiation protocol wherein pluripotent stem cells (pSCs), including induced pluripotent stem cells (iPSCs), and embryonic stem cells (ESCs) can be differentiated using an embryoid body (EB) formation step, followed by 20-day EB maturation via endothelial cells (EC) co-culturing and incubation with a bone morphogenic protein (BMP)-related growth factor cocktail. The resulting cells displayed capability for expansion in culture, functional properties, including insulin-production and glucose signaling response, and mature phenotype of C-peptide expression. Up to ~50, ~75%, and even ~95% of hPSCs can be successfully converted into beta-cells with these functional, mature properties. Higher expression of beta cell markers (insulin, PDX-1, Nkx6.1, Kir6.2, Glut2, GKS, SUR1, PC1/3, PC2, and amilin) was found in sorted cells compared to non-sorted cells (P<0.05).

Importantly, sorted and labeled cells are also capable of being expanded up to ten passages. Quinacrine secretion and human C-peptide was detected in the culture media of sorted cells at 0 (1.14±1.3 pmol/L) or 17 mM glucose concentrations (4.6, ±2.2 pmol/L, P<0.05). The levels of C-peptide in in vivo mice blood samples at 60 days after transplantation indicated an increase in C-peptide secretion after 30 (91.2±3.9 pmol/L) and 60 (150±10 pmoL/L) minutes of the glucose challenge (basal=58.2±1.5 pmol/L). Harvested cells were positive for insulin after 60 days post-ransplantation by IHC analysis. These results indicate that beta-cells can be derived from iPSCs and expanded in vitro and that these cells maintain their functional phenotype in vivo.

Described herein is a method of differentiating a human pluripotent stem cell into a cell capable of producing insulin including (a) providing a quantity of human pluripotent stem cells (pSCs), (b) culturing the pSCs in the presence of at least one differentiation agent, and at least one extracellular matrix (ECM) component, wherein the at least one differentiation agent and at least one ECM component are capable of differentiating the pSCs into a cell capable of producing insulin.

In another embodiment, culturing the pSCs includes inducing the formation of embryoid bodies (EBs). In various embodiments, culturing the pSCs includes inducing the formation of EBs, which can be cultured up to 1, 2, 3, 4, 5, 6, 7, 1 week or more, 2 weeks or more, 3 weeks or more, to promote various states of differentiation. In certain embodiments, the EBs can be cultured in the presence of ROCK inhibitor, or in a high density plate or other apparatus to promote uniformity in shape, size, and consistency in differentiation state of the cells of the EB. In another embodiment, the EBs are cultured in the presence of endothelial cells. In various embodiments, the EBs are deposited in a gel mixture containing ECM components. In various embodiments, gel mixture containing ECM components includes at least one collagen and at least one laminin. This includes, for example, a gel mixture containing collagen I, IV, and laminin I. In another embodiment, the endothelial cells are human microvascular endothelial cells (HMECs). In other embodiments, the endothelial cells are derived from iPSCs or from the dermis of the same patient. the In various embodiments, the endothelial cells are from aorta, dermis, bladder, and coronary arteries, or endothelial cells derived from pSCs. In various embodiments, the EBs, or EBs co-culture with endothelial cells may be in a substantially two-dimensional, or substantially three-dimentional apparatus.

In another embodiment, the at least one first differentiation agent in step (b) includes activin A and wingless-related MMTV integration site 3A (WNT3A). In another embodiment, the method includes (c) culturing the pSCs in the presence of at least one second differentiation agent including all-trans retinoic acid (RA) and keratinocyte growth factor (KGF), (d) culturing of the pSCs in the presence of at least one third differentiation agent including epidermal growth factor (EGF), and (e) culturing the pSCs in the presence of at least one fourth differentiation agent including hepatocyte growth factor (HGF), insulin-like growth factor (IGF1), exendin-4 and nicotinamide. In various embodiments, the differentiation agents include molecules capable of modulating the BMP, WNT, and Activin-signaling pathways. This includes, for example, BMP-2, and BMP-4. In other embodiments, the at least one differentiation is provided via media conditioned by an endothelial cell culture.

In another embodiment, the cell capable of producing insulin is a definitive endoderm (DE) cell. In another embodiment, the DE cell expresses CXCR, SOX17, or both. In another embodiment, the cell capable of producing insulin expresses one or more markers selected from the group including: proinsulin, insulin, glucagon, and somatostatin. Other markers include, for example, PDX-1, Ngn3, GLUT2, GKS, SUR1, Nkx6.1 and Kir6.2. In another embodiment, the cell capable of producing insulin is responsive to glucose. In another embodiment, the cell capable of producing insulin secretes C-peptide. In another embodiment, the cell capable of producing insulin can be expanded in vitro. In another embodiment, the cell capable of producing insulin is a beta-cell.

In another embodiment, the ECM component includes at least one ECM component selected from the following: a collagen, a laminin, an integrin, a fibronectin, a proteoglycan, and an elastin. In another embodiment, the ECM component includes collagen I, IV, and laminin I In a different embodiment, cell capable of producing insulin, is produced by any of the methods described herein. In another embodiment, the present invention includes a cell line including cell capable of producing insulin, is produced by any of the methods described herein. In various embodiments, cells or cell lines produced by the described methods can be expanded for 1, 2, 3, 4, 5, 6, 7, 8, 9, 10, 10 or more passages without a loss of karyotype stability. In various embodiments, the methods described herein are able to convert 10, 20, 30, 40, 50, 60, 70, 80, 90, 90% or more of a quantity of pSCs into insulin-producing cells, such as beta-cells. In various embodiments, the pSCs are induced pluripotent stem cells (iPSCs) or human embryonic stem cells (hESCs).

In another embodiment, the cell capable of producing insulin is derived from a pSC according to the method by (a) providing a quantity of human pluripotent stem cells (pSCs), (b) culturing the pSCs in the presence of at least one differentiation agent, and at least one extracellular matrix (ECM) component, wherein the ECM component includes a collagen, a laminin, or both, (c) culturing the pSCs in the presence of at least one second differentiation agent, (d) culturing of the pSCs in the presence of at least one third differentiation agent, and (e) culturing the pSCs in the presence of at least one fourth differentiation agent. In other embodiments, the at least one differentiation in some or all of steps (b), (c), (d), and/or (e) is provided via media conditioned by an endothelial cell culture.

In another embodiment, the cell capable of producing insulin is derived from a pSC according to the method by (a) providing a quantity of human pluripotent stem cells (pSCs), (b) culturing the pSCs in the presence of at least one differentiation agent, and at least one extracellular matrix (ECM) component, wherein the ECM component includes a collagen, a laminin, or both, (c) culturing the pSCs in the presence of at least one second differentiation agent including all-trans retinoic acid (RA) and keratinocyte growth factor (KGF), (d) culturing of the pSCs in the presence of at least one third differentiation agent including epidermal growth factor (EGF), and (e) culturing the pSCs in the presence of at least one fourth differentiation agent including hepatocyte growth factor (HGF), insulin-like growth factor (IGF1), exendin-4 and nicotinamide.

In another embodiment, the cell capable of producing insulin is derived from a pSC according to the method by (a) providing a quantity of human pluripotent stem cells (pSCs), (b) inducing the formation of embryoid bodies (EBs) from the pSC, (c) culturing the EBs in the presence of: at least one differentiation agent comprising activin A and wingless-related MMTV integration site 3A (WNT3A), at least one extracellular matrix (ECM) component comprises a collagen, and a laminin, and a quantity of human microvascular endothelial cells (HMECs), (d) culturing the EBs in the presence of at least one second differentiation agent including all-trans retinoic acid (RA) and keratinocyte growth factor (KGF), (e) culturing of the EBs in the presence of at least one third differentiation agent including epidermal growth factor (EGF), and (f) culturing the EBs in the presence of at least one fourth differentiation agent including hepatocyte growth factor (HGF), insulin-like growth factor (IGF1), exendin-4 and nicotinamide. For example, the 6-day old EBs are treated with 100 ng/ml activin A and 25 ng/ml wingless-related MMTV integration site 3A (WNT3A) in RPMI1640 for 1 day (DAY1). On the following 2 days (up to DAY3), 100 ng/ml activin A was added, supplemented with 0.2% FBS. In step 2, the cells were cultured in DF12 supplemented with 2 µmol/l all-trans retinoic acid and 50 ng/ml keratinocyte growth factor 6 days (up to DAY9). Following this, in step 3 (DAY 10-15), cells were treated with 50 ng/ml epidermal growth factor (EGF) nd 1 mol/l SB431542 in DMEM-H. In the final step 4, the cells were incubated in DMEM with 50 ng/ml hepatocyte growth factor, 50 ng/ml IGF1, 50 ng/ml exendin-4, and 10 mmol/l nicotinamide for 7 days (DAY 16-22).

In various embodiments, differentiated cells produced by the described methods are labeled using an expression vector under the control of a specific promoter. For example, an insulin-promoter coupled with a label, such as mCherry reporter gene can allow for the isolation and/or identification of insulin-producing cells, such as beta cells. In another embodiment, the differentiated cells can contain a second label, such as constitutively expressed hrGFP-NLS reporter under the control of human ubiquitin C promoter. In various embodiments, differentiated cells containing one or more (e.g., dual reporter) labels can be used for as a screening cell line for testing the efficacy of various therapeutic agents.

Also described herein is a pharmaceutical composition including a pluripotent stem cell (pSC)-derived beta-cell, and a pharmaceutically acceptable carrier. In another embodiment, the beta-cell is derived from a pSC according to the method including (a) providing a quantity of human pluripotent stem cells (pSCs), (b) culturing the pSCs in the presence of at least one differentiation agent, and at least one extracellular matrix (ECM) component, wherein the ECM component includes a collagen, a laminin, or both, (c) culturing the pSCs in the presence of at least one second differentiation agent including all-trans retinoic acid (RA) and keratinocyte growth factor (KGF), (d) culturing of the pSCs in the presence of at least one third differentiation agent including epidermal growth factor (EGF), and (e) culturing the pSCs in the presence of at least one fourth differentiation agent including hepatocyte growth factor (HGF), insulin-like growth factor (IGF1), exendin-4 and nicotinamide.

In another embodiment, the beta-cell is derived from a pSC according to the method by (a) providing a quantity of human pluripotent stem cells (pSCs), (b) inducing the formation of embryoid bodies (EBs) from the pSC, (c) culturing the EBs in the presence of: at least one differentiation agent comprising activin A and wingless-related MMTV integration site 3A (WNT3A), at least one extracellular matrix (ECM) component comprises a collagen, and a laminin, and a quantity of human microvascular endothelial cells (HMECs), (d) culturing the EBs in the presence of at least one second differentiation agent including all-trans retinoic acid (RA) and keratinocyte growth factor (KGF), (e) culturing of the EBs in the presence of at least one third differentiation agent including epidermal growth factor (EGF), and (f) culturing the EBs in the presence of at least one fourth differentiation agent including hepatocyte growth factor (HGF), insulin-like growth factor (IGF1), exendin-4 and nicotinamide.

Also described herein is a method of modulating diabetic phenotype, including selecting a patient diagnosed with a diabetic phenotype, and administering a quantity of insulin-producing pluripotent stem cell (pSC)-derived cells wherein the pSC-derived cells produce insulin to modulate the diabetic phenotype. In another embodiment, the of insulin-producing pluripotent stem cell (pSC)-derived cell is derived by (a) providing a quantity of human pluripotent stem cells, (b) culturing the pSCs in the presence of at least one differentiation agent, and at least one extracellular matrix (ECM) component, wherein the ECM component includes a collagen, a laminin, or both, (c) culturing the pSCs in the presence of at least one second differentiation agent including all-trans retinoic acid (RA) and keratinocyte growth factor (KGF), (d) culturing of the pSCs in the presence of at least one third differentiation agent including epidermal growth factor (EGF), and (e) culturing the pSCs in the presence of at least one fourth differentiation agent including hepatocyte growth factor (HGF), insulin-like growth factor (IGF1), exendin-4 and nicotinamide.

In another embodiment, the insulin-producing pluripotent stem cell (pSC)-derived cell by (a) providing a quantity of human pluripotent stem cells (pSCs), (b) inducing the formation of embryoid bodies (EBs) from the pSC, (c) culturing the EBs in the presence of: at least one differentiation agent comprising activin A and wingless-related MMTV integration site 3A (WNT3A), at least one extracellular matrix (ECM) component comprises a collagen, and a laminin, and a quantity of human microvascular endothelial cells (HMECs), (d) culturing the EBs in the presence of at least one second differentiation agent including all-trans retinoic acid (RA) and keratinocyte growth factor (KGF), (e) culturing of the EBs in the presence of at least one third differentiation agent including epidermal growth factor (EGF), and (f) culturing the EBs in the presence of at least one fourth differentiation agent including hepatocyte growth factor (HGF), insulin-like growth factor (IGF1), exendin-4 and nicotinamide. In various embodiments, administering a quantity of insulin-producing pluripotent stem cell (pSC)-derived cells can include simultaneous administration of endothelial cells.

Example 1

General Methods

Generally, the multi-step differentiation protocol for generating of beta-cells from pSCs is shown in FIG. 1. An embryoid body (EBs) formation step (FIG. 1a) can be applied, or a direct differentiation technique involving WNT pathway growth factors can lead to formation of definitive endoderm. As demonstrated in FIG. 1b, a multi-step growth factor cocktail can be added to EBs, for differentiation of pSCs can be differentiated into insulin-producing beta-cells, without or without co-culture in the presence of endothelial cells (ECs). An example of the EB/EC co-culture apparatus in collagen-laminin gel mixture is shown in FIG. 1c, containing human microvascular endothelial cells (HMECs), EBs, and co-culture (FIG. 1d, e, f, respectively). For analysis, these beta-cells can be labeled with a red fluorescent protein under the control of insulin promoter for isolation and expansion. Beta-cell marker expression was evaluated by immunocytochemistry and qRT-PCR. Quinacrine secretion assay and ELISA were used to evaluate secretion of C-peptide in vitro after a glucose challenge. For in vivo studies, labeled cells can be sorted by FACS and transplanted under the kidney capsule of SCID mice.

Example 2

Cells and Reagents

The human pluripotent stem cell lines and human embryonic stem cell line H9 were obtained from the iPSC core at Cedars-Sinai Regenerative Medicine Institute (RMI). Derivation of the iPSC at the core is performed by using the published Yamanka method for iPSC generation from human fibroblasts (Takahashi and Yamanaka, 2006; Nakagawa and Yamanaka, 2010). Expression of pluripotent markers (Oct-4, SSEA-3, SSEA-4, TRA 1-60, and TRA 1-81) and karyotyping has been done in the core to fully characterize these cells. The iPS cell line 83iCTR-n1 was used between passages 40-50. The H9 cell line was also obtained from RMI passage 20-30. Both cell lines were maintained in a feeder free system using culture dishes pre-coated with Matrigel. Culture medium for these cells consisted of mTeSR™1 basal media supplemented mTeSR™1 5× supplements (Invitrogen, Carlsbad, Calif.), 200 µM L-alanyl-L-glutamine (ATCC), 0.1 mM β-mercaptoethanol (STEMCELL Technologies, Vancouver, Canada). Cultures of iPSC/hESCs were passaged by detaching the colonies mechanically at 1:3 split ratio every 7 days.

Example 3

EB Differentiation in the Presence of Growth Factor Cocktail

Embryoid bodies (EBs) were generated using AggreWell system (STEMCELLTechnologies, Vancouver, Canada) and according to manufacturer instructions. These EBs were maintained in AggreWell medium (STEMCELL Technologies, Vancouver, Canada) supplemented with 10 µM ROCK inhibitor (Sigma-Aldrich, St. Louis, Mo.) at 37° C. in humidified incubator at 5% CO2.

Alternatively, culturing in the presence of matrigel in high density plates can also be utilized to produce EBs of uniform size and consistency. Embryoid body formation media include IMDM is first prepared in a 15 mL falcon tube on ice (17% KO Serum Replacer, 1% MEM-NEAA, 1% L-alanyl-L-glutamine, 110 µM Beta-mercaptoethanol, 10 µM ROCK inhibitor, remainder up to 100% volume IMDM). Cells are harvested with Accutase, and placed in suspension. For example, from 2-3 confluent (70-80%) wells of a 6-well plate, these cells can make EBs in one 384-well plate. The cells can be counted to ensure that the number of cell plated is in a range of 5000 cells per well of a 384-well plate. It means that the total should be approximately $2 \times 10^6$ cells/plate. The cell suspension is transferred to a tube and spin down at 1100 RPM for 5 min. Supernatant is aspirated and re-suspend in 10 mL of IMDM differentiation media +10 µM ROCK inhibitor (stock is at 10 mM, 1000×)+cold matrigel (0.5 mg/384 well plate) in the pre-chilled tube in ice. Use 25 µL volume cell suspension to plate cells per well, which should be 10 ml/384-well plate. Seeding in the wells constitutes day 0 for EBs (EBd0). A sterile lid is placed on the plate, spun at 1,400 rpm at 4° C. for 10 min, and placed in incubator overnight at 37° C. By the fourth day (EBd4), the EBs should be transferred from the 384-well plate to Petri dishes and the same media for EB differentiation should be added. Wait for two more days for the EBs (EBd6) to grow and become visible with naked eye. The EBd6 are then to be plated in collagen gels, either alone or together with endothelial cells.

Confluent monolayers of human microvascular endothelial cells (HMECs) were grown at 37° C. under 5% $CO_2$ and maintained in MCDB131 medium (Invitrogen, Carlsbad, Calif.) supplemented with 1% L-Glutamine (Invitrogen, Carlsbad, Calif.), 10% FBS (Omega Scientific, Tarzana, Calif.), and 100 µg/ml Endothelial Cell Growth Supplement (ECGS) (Upstate, Temecula, Calif.). These cells were used at passages 20 to 25. To co-culture the cells, 100 EBs and 5×10⁵ HMECs were added to 1 mL of collagen I solution (BD Bioscience, Franklin Lakes, N.J.) that contained 1×MEM, 1 M HEPES buffer, 7.5% Bicarbonate solution (Life Technologies, Grand Island, N.Y.), 0.1 N NaOH, sterile water, 1 mg/mL laminin and 1 mg/mL collagen IV (R&D Systems, Minneapolis, Minn.) placed in ice. After mixing the cells gently in this solution, 10 drops of 100 µL were placed in Petri dishes and incubated for gel solidification at 37° C. during 10-20 min.

After this time, media with growth factors was added according to published protocols to derive insulin-producing cells (Zhu et al., 2011). EB control samples were included in the gels without as cultured without ECs and treated with the same growth factors. After 20 or 30 days, the gels were placed in 15 mL Falcon tube with 5 mL collagenase I (Worthington, Lakewood, N.J.) for 1 hour in water bath at 37° C. Then, the cell suspension was collected and replated on collagen-laminin precoated flasks.

Example 4

Growth Factor Differentiation Protocol

The differentiation protocol is described in FIG. 1a. The media used here, RPMI1640, DF12 and DMEM, were all supplemented with 2 mmol/l Glutamax, 0.1 mmol/l non-essential amino acids, 55 µmol/l betamercaptoethanol and penicillin/streptomycin. DF12 and DMEM were also supplemented with 1% B27 (all from Gibco, Carlsbad, Calif., USA).

In step 1, either undifferentiated iPSCs, or EBd6 are treated with 100 ng/ml activin A (PeproTech, Rocky Hill, N.J., USA) and 25 ng/ml wingless-related MMTV integration site 3A (WNT3A) (R&D Systems, Minneapolis, Minn., USA) in RPMI1640 for 1 day (DAY1). On the following 2 days (up to DAY3), 100 ng/ml activin A was added, supplemented with 0.2% FBS. In step 2, the cells were cultured in DF12 supplemented with 2 µmol/l all-trans retinoic acid (RA; Sigma, St Louis, Mo., USA) and 50 ng/ml keratinocyte growth factor (KGF; PeproTech) for 6 days (up to DAY9). Following this, in step 3 (DAY 10-15), cells were treated with 50 ng/ml epidermal growth factor (EGF) (PeproTech) and 1 µmol/l SB431542 (Tocris Bioscience, Ellisville, Mo., USA) in DMEM-H. In the final step 4, the cells were incubated in DMEM with 50 ng/ml hepatocyte growth factor (HGF; PeproTech), 50 ng/ml IGF1 (PeproTech), 50 ng/ml exendin-4 (Sigma) and 10 mmol/l nicotinamide (Sigma) for 7 days (DAY 16-22).

Example 5

Harvesting and Passaging of Differentiated Cells

Confluent monolayers of labeled (mCherry-positive) cells were harvested with accutase (Innovative Cell Technologies, Inc. San Diego) at passage 3 after lenti infection. A cell suspension was prepared at cell density of 1×10⁶ cells/mL. 0.5 mL of this cell suspension was analyzed by FACS. About 70% percent of the cells were mCherry-positive and they were plated in (10 µg/mL) laminin-1-collagen-IV (R&D Systems, Inc., Minneapolis, Minn.) pre-coated dishes. The plated cells were considered as passage 0 after sorting.

Example 6

Quantitative Real Time RT-PCR (qRT-PCR) Analysis

Total RNA was isolated from differentiated cells before and after sorting using RNAeasy mini kit (Qiagen, Valencia, Calif.). After cDNA synthesis, using a QuantiTect Reverse Transcription kit (Qiagen, Valencia, Calif.), quantitative real-time PCR analysis was performed using a SYBR Green RT-PCR kit (Qiagen, Valencia, Calif.) and the LightCycler instrument (AB Applied Biosystems, Foster City, Calif.). PCR cycle conditions included a first step for initial polymerase activation for 10 minutes at 95° C. and 45 cycles of denaturation at 94° C. for 30 seconds, annealing at 60° C. for 20 seconds, and elongation at 72° C. for 30 seconds. The forward and reverse primers used (all sequences are 5'-3') were those listed in Table 1:

TABLE 1

Forward and Reverse Primers for qRT-PCR

| Gene | Forward Primer<br>Reverse Primer |
|---|---|
| GAPDH | AGCCACATCGCTCAGACACC<br>[SEQ ID NO: 1]<br>GTACTCAGCGGCCAGCATCG<br>[SEQ ID NO: 2] |
| Insulin | AGCCTTTGTGAACCAACACC<br>[SEQ ID NO: 3]<br>GCTGGTAGAGGGAGCAGATG<br>[SEQ ID NO: 4] |
| PDX-1 | GGATGAAGTCTACCAAAGCTCACGC<br>[SEQ ID NO: 5]<br>CCAGATCTTGATGTGTTCTCTCGGTC<br>[SEQ ID NO: 6] |
| Ngn3 | CAATCGAATGCACAACCTCA<br>[SEQ ID NO: 7]<br>GGGAGACTGGGGAGTAGAGG<br>[SEQ ID NO: 8] |
| GLUT2 | AGGACTTCTGTGGACCTTATGTG<br>[SEQ ID NO: 9]<br>GTTCATGTCAAAAAGCAGGG<br>[SEQ ID NO: 10] |
| GKS | AAGAAGGTGATGAGACGGATGC<br>[SEQ ID NO: 11]<br>CATCTGGTGTTTGGTCTTCACG<br>[SEQ ID NO: 12] |
| SUR1 | GTGCACATCCACCACAGCACATGGCTTC<br>[SEQ ID NO: 13]<br>GTGTCTTGAAGAAGATGTATCTCCTCAC<br>[SEQ ID NO: 14] |
| Kir6.2 | CGCTGGTGGACCTCAAGTGGC<br>[SEQ ID NO: 15]<br>CCTCGGGGCTGGTGGTCTTGCG<br>[SEQ ID NO: 16] |

Negative controls were included in each analysis. In this case the RNA was not treated with reverse transcriptase (No RT). All samples were run in triplicate and PCR products were observed by gel electrophoresis on 2% agarose ethidium bromide-stained gels. Analysis was performed using 7300 Sequence Detection Software (SDS) Version 1.3

(Software Core Application, AB Applied Biosystems, Foster City, Calif.). Following real time PCR, a dissociation curve was run to detect primer dimmers, contaminating DNA, and PCR products from misannealed primers.

The inventors used a standard curve obtained by running a GAPDH plasmid with a known copy-number value based on its molecular weight. Automatic baseline and threshold feature (Ct) of the SDS software (auto Ct) was performed and the system considered Ct values established in the geometric phase of the amplification curve for each marker with minimal standard deviation. The standard curve was then used as a reference for extrapolating quantitative information for mRNA targets of unknown concentrations. In this manner, the absolute number of copies was determined for each marker. The absolute number of copies of the specific marker was then divided by the absolute number of copies of GAPDH of the same sample for normalization (mouse housekeeping gene).

Example 7

Plasmid Construction and Infection

For construction of lenti reporter plasmid, the rat insulin minimal promoter was PCR amplified using the following primer combination:

```
forward primer:
                                       [SEQ ID NO: 17]
5'-CCCTCTAGACCGGCTGAGCTAAGAATCCAG-3'
(XbaI sequence is underlined)

reverse primer:
                                       [SEQ ID NO: 18]
5'GGCGACCGGTGCGGGAGTTACTGGGTCTCCACTAG-3'
(AgeI sequence is underlined).
```

The XbaI and AgeI restriction enzyme digested PCR product was cloned into XbaI-AgeI sites upstream of mCherry reporter gene in a self-inactivating second generation lenti viral vector. This vector also contained a constitutively expressed hrGFP-NLS reporter under the control of human ubiquitin C promoter. Following the differentiation protocol, the cells were plated at $5 \times 10^4$ cells/mL in a gelatin precoated 48-well plates. At 60% confluence, transduction with the rat INS-mCherry lenti viral vector was performed. Four hours post transduction, the cells were washed with basal media and fresh maintenance media was added. This media consisted in RPMI 1640 (Cellgro, Manassas, Va.) supplemented with 10% FBS (Omega Scientific Inc., Tarzana, Calif.), 200 mM L-alanyl-L-glutamine, 200 mM MEM non-esential amino acids, 200 mM sodium pyruvate, 100 μM beta mercaptoethanol, 100 mM penicillin-streptomycin, and 10 mM HEPES (Life Technologies, Grand Island, N.Y.). The transduction efficiency was monitored by the number of cells expressing hrGFP-NLS reporter.

Example 8

FACS Sorting and Isolation of Beta-Cells Derived from iPSCs

After cell expansion, $1 \times 10^6$ labeled cells were harvested to obtain a cell suspension. The cells were harvested using accutase and washed with 1% BSA in 1×PBS. The cell pallet was resuspended in 1 mL of RPMI 1640 supplemented with 1% BSA and they were subjected to FACS sorting. After sorting, the cells were plated in a NUNC 4-well dish (VWR, Brisbane, Calif.) pre-coated with collagen-laminin.

Example 9

Quinacrine Secretion Assay

Differentiated cells were plated on 24-well plates at $1 \times 10^5$ cells/mL. Then, the cells were placed at 37° C., 5% CO2 for 24 hours. After this time, the complete medium was removed and the cells were washed with PBS before adding 500 μL of glucose free RPMI 1640 medium (Life Technologies, Grand Island, N.Y.) supplemented with 0.1% bovine serum albumin (BSA). This medium was replaced for 100 nM quinacrine dihydrochloride (Sigma-Aldrich, St. Louis, Mo.) and the cells were placed into the incubator at 37° C., 5% CO2 for 30 min. Then, the cells were washed with PBS and images were taken under a fluorescent microscope with fluorescence excitation at 360 nm and emission at 500 nm. The PBS was then replaced with RPMI 1640 supplemented with 0.1% BSA and different concentrations of glucose (0.5 mM, 1.0 mM, 2.8 mM, 5.6 mM or 16.5 mM) added to separate wells with cells that already uptake quinacrine as described above. The cells with different glucose concentrations were incubated at 37° C., 5% CO2 for one hour. After this time, the cells were washed with PBS and imaged with fluorescence excitation at 360 nm and emission at 500 nm. The fluorescence intensity was quantified using the image tools of ImageJ 1.30v software (Wayne Rasband National Institutes of Health; USA).

Example 10

Immunocytochemistry (ICC) of Differentiated Cells in Culture

The differentiated cells on coverslips were fixed with paraformaldehyde 4% (Polysciences, Inc., Warrington, Pa.) and permeabilized with 0.3% triton X-100 in PBS for 5 minutes. After rinsing with PBS, cells were blocked with PBS/5% BSA for 1 hour and exposed overnight using the following primary antibodies: anti-human Proinsulin C-peptide (Millipore, Billerica, Mass.), antiNgn3 (Lifespan Biosciences, Inc., Seattle, Wash.), anti-Nkx2.2 (Sigma-Aldrich, St. Louis, Mo.), anti-Nkx6.1 (developed by Ole D. Madsen and obtained from the Developmental Studies Hybridoma Bank developed under the auspices of the NICHD and maintained by the Univerity of Iowa, Iowa City, Iowa 52242), anti-macro H2A.2 (Barr body), anti HLA Class 1 ABC, anti-nuclear human antigen, antisomatostatin, antiglucagon, anti-PDX-1 (abcam, San Francisco, Calif.), normal mouse $IgG_1$ (negative control), normal rabbit IgG (negative control) (Santa Cruz Biotechnology, Inc., Santa Cruz, Calif.). The secondary antibodies used included Alexa Fluor 555 goat anti-rabbit IgG, Alexa Fluor 555 goat anti-mouse IgG (Molecular Probes, Eugene, Oreg.). All the secondary antibodies were diluted 1:1000 in blocking solution (BSA 5% in 1×PBS). Images were acquired with a multi-purpose zoom microscope (Nikon AZ 100, USA; http://www.nikon.com/) attached to a DS-Qil High-sensitivity CCD Camera (http://www.nikon.com/) and analyzed using an imaging software NIS-Elements AR 3.10 (Nikon Instruments, Melville, N.Y.) and the image tools of ImageJ 1.30v software (Wayne Rasband National Institutes of Health; USA).

Example 11

Karyotyping and Cell Transplantation

Cell samples of INS-eGFP expressing cells at early (passage 5) and late passages (passage 10) were sent to Cell Line Genetics (Madison, Wis.) for karyotyping analysis.

Confluent monolayers of eGFP-expressing cells were expanded and harvested at passage 5 after sorting with accutase (Innovative Cell Technologies, San Diego, Calif.) After centrifugation, all the media was removed and the cell pellet with $3 \times 10^6$ cells was transferred to a 1.5 mL eppendorf tubes placed on ice. Animal experiments were approved by The Cedars-Sinai Animal Care and Use Committee (IACUC). With the mouse under anesthesia, a 2.5 cm incision was made above the left kidney. Embryonic-derived INS-eGFP expressing cells were injected (transplanted) under the kidney capsule using a 1 mL insulin syringe with an ultrafine needle (½", 30 g). In another control group, mice were transplanted with cells derived from embryoid bodies (EBs) cultured alone and treated with the same growth factors. The skin was then closed in a subcuticular pattern. Blood samples were collected before the surgery, 30 and 60 days after transplantation. Five mice were used as controls. In these mice, no cells but PBS was injected under the kidney capsule. After 60 days, the mice were euthanized and the left kidneys harboring the transplanted cells were removed for Immunohistochemistry (IHC) analysis.

Example 12

Human C-Peptide Determination

Human C-peptide was measured by ultrasensitive ELISA (Mercodia, Winston Salem, N.C.) in mice blood samples at different time points. The detection limit for this assay is 2.5 pmol/L (0.0076 µg/L).

Example 13

Immunohistochemistry of Cell Grafts

After harvesting, the grafted and non-grafted kidneys were photographed and fixed with 1% paraformaldehyde. Small sections of the kidneys were embedded in cryogel and frozen in cold 2methylbutane (Sigma, St. Louis, Md.). Some 7-µm frozen sections were fixed with 4% neutral buffer formalin (NBF) to be stained with Hematoxylin and Eosin using manufacturer instructions (American MasterTech, Lodi, Calif.). Other samples were fixed with cold acetone and dry at room temperature for 24 hrs. These samples were stained with mouse anti-human C-peptide antibody as primary and biotin-C-anti-mouse IgG as secondary antibody. Streptavidin HRP was applied to the complex and then AEC for development. The nuclei were counterstained with Hematoxylin.

Example 14

Co-Culture System of iPSC-EBs and Endothelial Cells (ECs)

Figure 2:
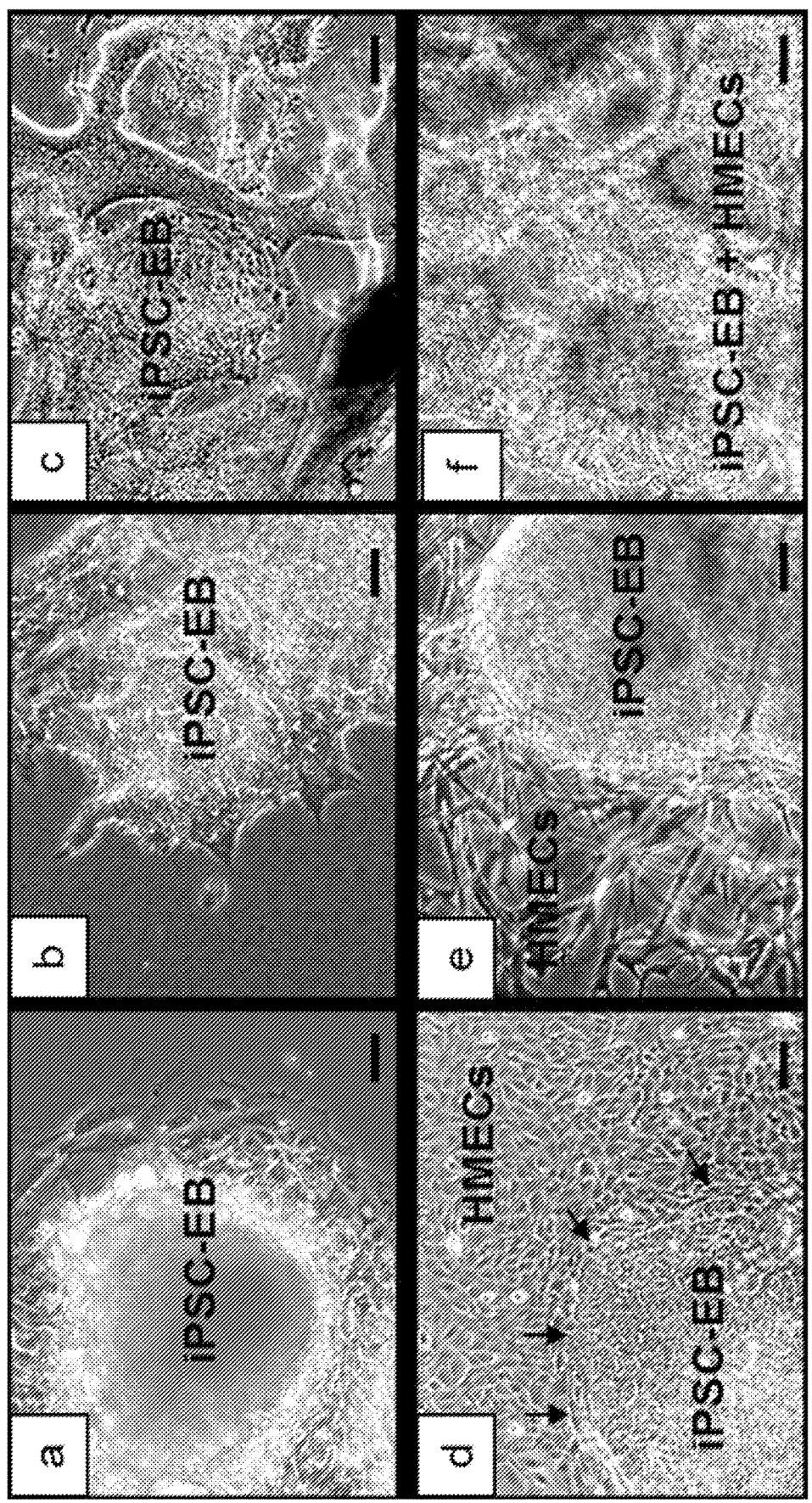
FIG. 2. Two- and Three-dimensional co-cultures between iPSC-EBs and ECs. Embryoid bodies (EBs) derived from iPSCs were cultured alone or together with human microvascular endothelial cells (ECs) in a cultured dish (two dimensional) or a collagen-laminin gel (three dimensional). (a) iPSC-derived EB cultured alone on a coverslip for one week. (b) iPSC-EB cultured alone in a gel for two weeks and (c) four weeks. iPSC-EB co-cultured with ECs in a coverslip for one week that form a cell-cell interface (black arrows). (e) iPSC-EB cultured together with ECs in a gel for two weeks and (f) four weeks. (a, b, d, and e) Bar=50 µm. (c and f) Bar=100 µm.

Using the described methods, the inventors were able to established and optimize co-culture system between iPSC-derived EBs and human microvascular endothelial cells (ECs). The EB cells proliferated normally in a two-dimensional (FIG. 2a) or three-dimensional cultures up to four weeks (FIG. 2b, c). Effective interaction took place between EBs and ECs in a two-dimensional culture in which the ECs formed a monolayer (FIG. 2d).

However, in this 2-D condition, close interaction only take place at the interface where the EB cells contact ECs (arrows in FIG. 2d). By contrast, in a three-dimensional culture, the endothelial cells were found surrounding the iPSC-EBs in organized networks of tube-like structures after two weeks in a culture (FIG. 2e). After four weeks, continue proliferation of EBs and ECs took place in three-dimensional co-culture system (FIG. 2f).

Example 15

Formation of Islet-Like Structures in EBs Co-Cultured with ECs

Figure 3:
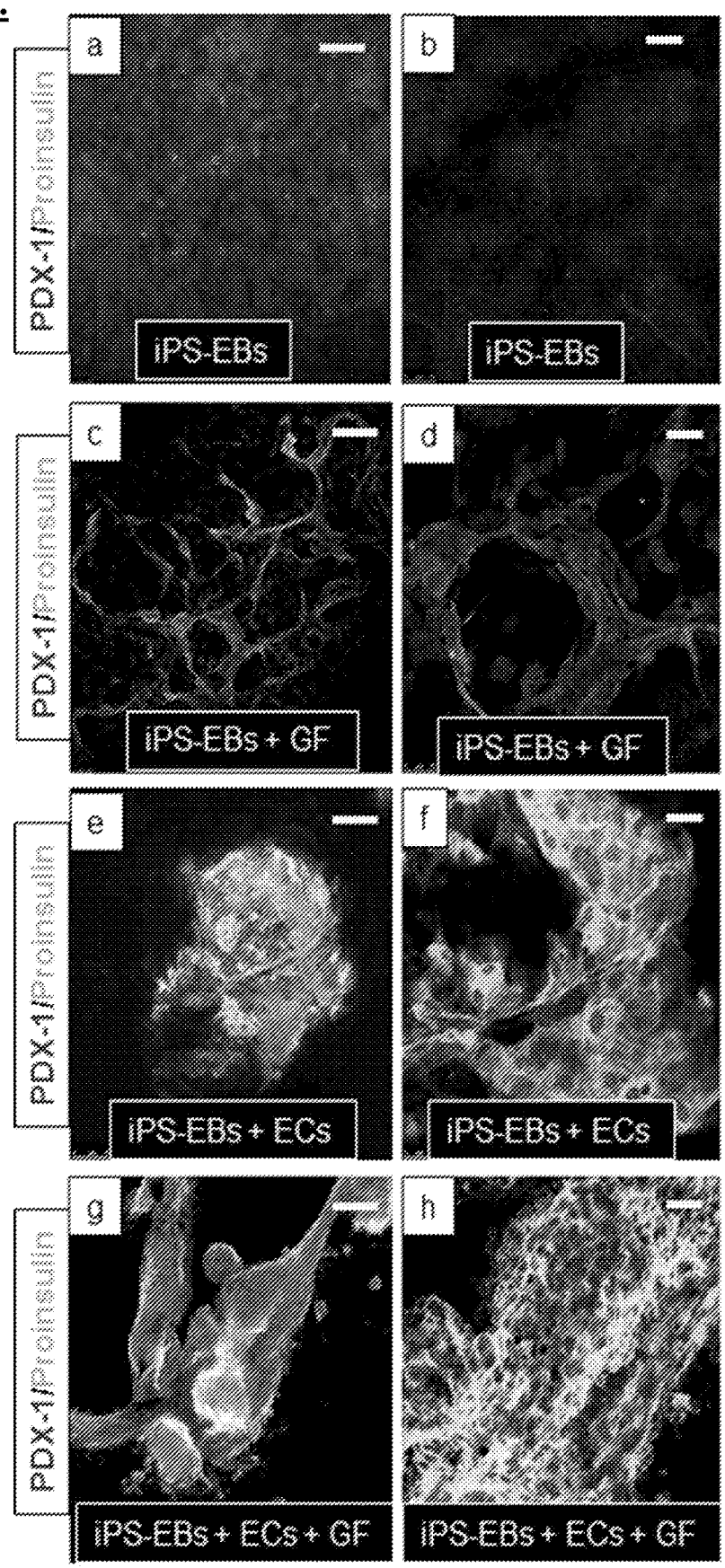
FIG. 3. Co-expression of PDX-1 and proinsulin in co-cultured iPSC-derived EBs. Lower and higher magnification respectively of (a, b) iPSC-EBs cultured alone with no growth factor treatment. (c, d) iPSC-EBs cultured alone and treated with growth factors. (e, f) iPSC-EBs co-cultured with human microvascuilar endothelial cells (ECs) not treated with growth factors and (g, h) iPSC-EBs co-cultured with ECs and treated with growth factors. (a, c, e, g) Bar=100 µm. (b, d, f, h) Bar=10 µm.

To evaluate expression of beta cell markers some iPSC-derived EB alone or with ECs were double stained to human proinsulin C-peptide and PDX-1 and other groups of these EBs were harvested for qRT-PCR analysis. EBs cultured alone not treated with growth factors did not express proinsulin or PDX-1 (FIG. 3a, b). EBs cultured alone treated with growth factors had some proinsulin expression with no PDX-1 co-expression (FIG. 3c, d).

Figure 4:
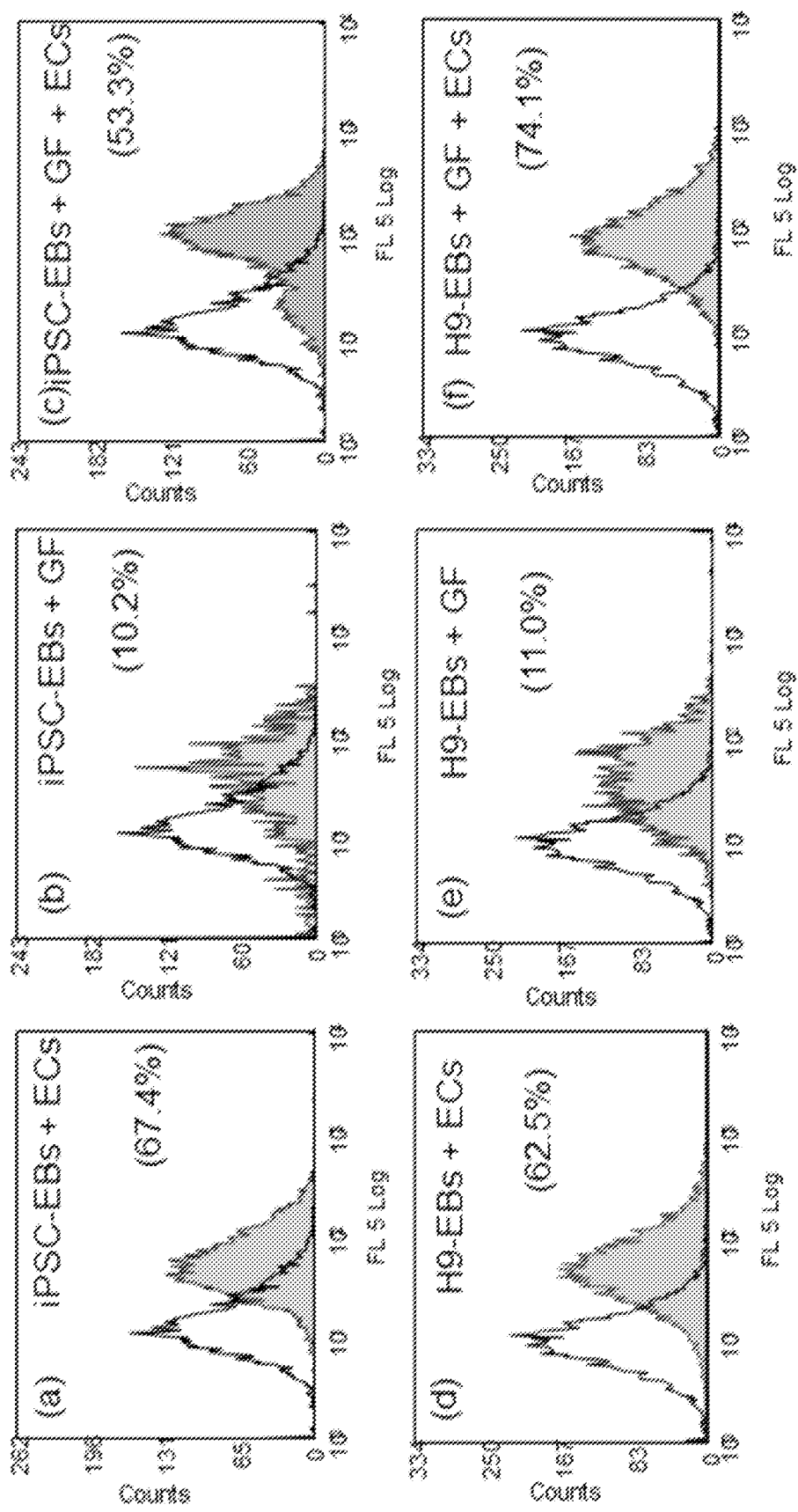
FIG. 4. Expression of proinsulin evaluated by FACS in iPSC-derived EBs. After about 20 days in co-culture with or without growth factors (see methods) either H9 or iPSCs were harvested, fixed, stained with anti-human proinsulin and Alexa 488 as secondary antibody. These cells were then analyzed by FACS. (a) iPSC-EBs co-cultured with ECs. (b) iPSC-EBs not co-cultured but treated with growth factors. (c) iPSC-EBs co-cultured with EC and treated with growth factors. (d) H9-EBs co-cultured with ECs. (e) H9-EBs treated with growth factors. (f) H9-EBs co-cultured with ECs and treated with growth factors.

By contrast, those EBs co-cultured with ECs untreated with growth factors developed cell clusters positive for proinsulin that co-expressed PDX-1 (FIG. 3e, f). Enhancement in the number of proinsulin and PDX-1 positive clusters was observed in co-cultured EBs treated with growth factors. Then, these cells were harvested and fixed to evaluate expression of proinsulin by FACS. Approximately 50-70% of the cells from co-cultured EBs treated with growth factors, either from iPSC or hESCs (H9), expressed proinsulin (FIG. 4c, f). Similar level of expression was found in EBs co-cultured with ECs but not treated with growth factors (FIG. 4a, d). Only 10% of the cells from control EBs (treated with growth factors but not co-cultured with ECs) were positive for proinsulin. These data suggest that ECs enhance the differentiation of pluripotent stem cells to insulin-producing beta-cells.

Example 16

Figure 5:
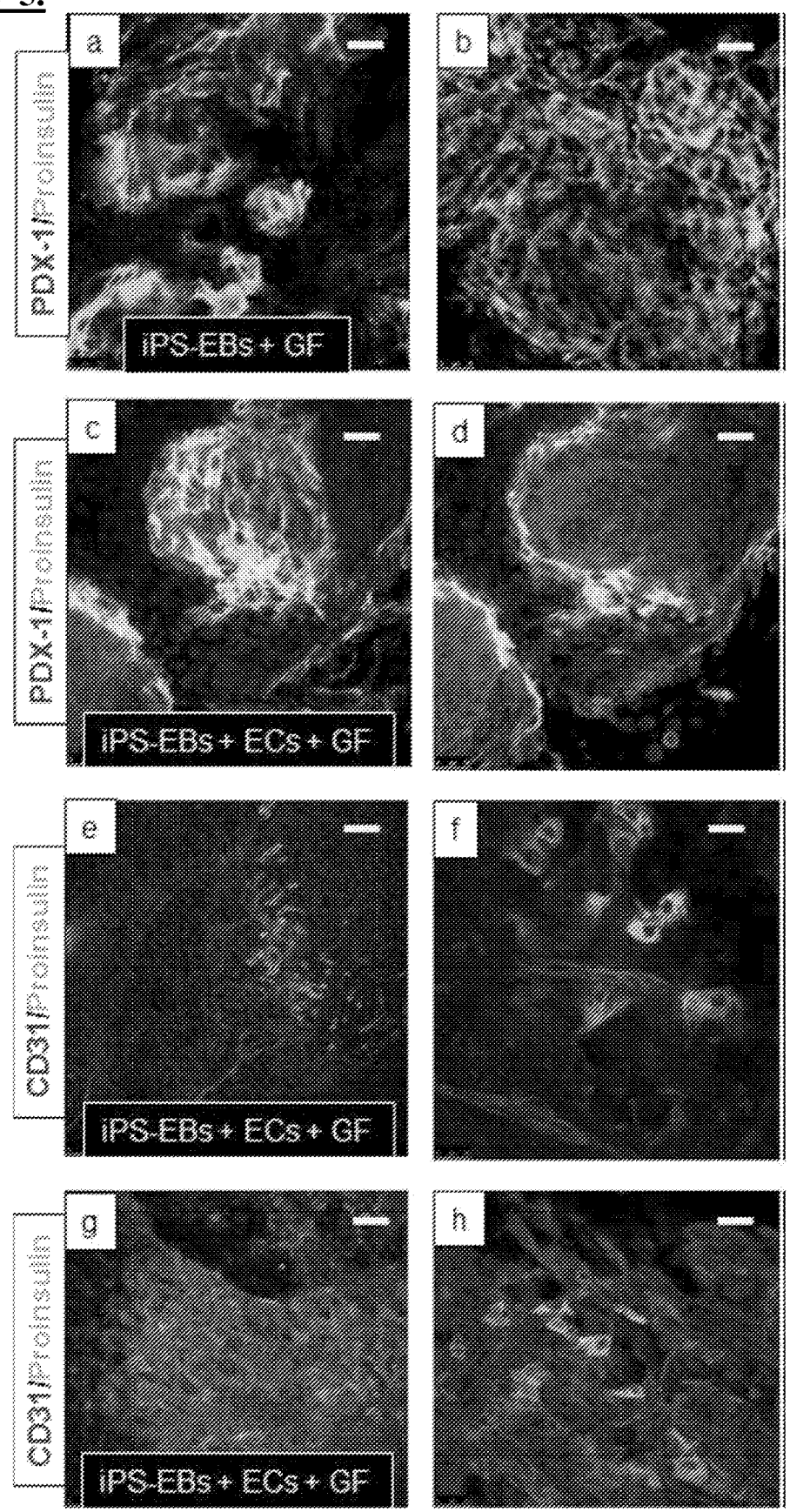
FIG. 5. Co-expression of proinsulin and PDX-1 positive cells derived from co-cultures that develop close to embryonic blood vessels. (a) iPSC-EBs treated with growth factors satained to proinsulin (green) and PDX-1 (red). (b) Same field as in "a" in a different plane. (c) iPSCderived EBs co-cultured with ECs and treated with growth factors stained to proinsulin (green) and PDX-1 (red). (d) Same field as in "b" in a different plane. (e) iPSC-derived EBs co-cultured with ECs and treated with growth factors stained to proinsulin (green) and CD31 (red). (f) Higher magnification of the image presented in "e". (g) iPSC-derived EBs co-cultured with ECs and treated with growth factors from a different experiment showing proinsulin staining (green) and CD31 staining (red). (h) Higher magnification of the image presented in "g".
Figure 18:
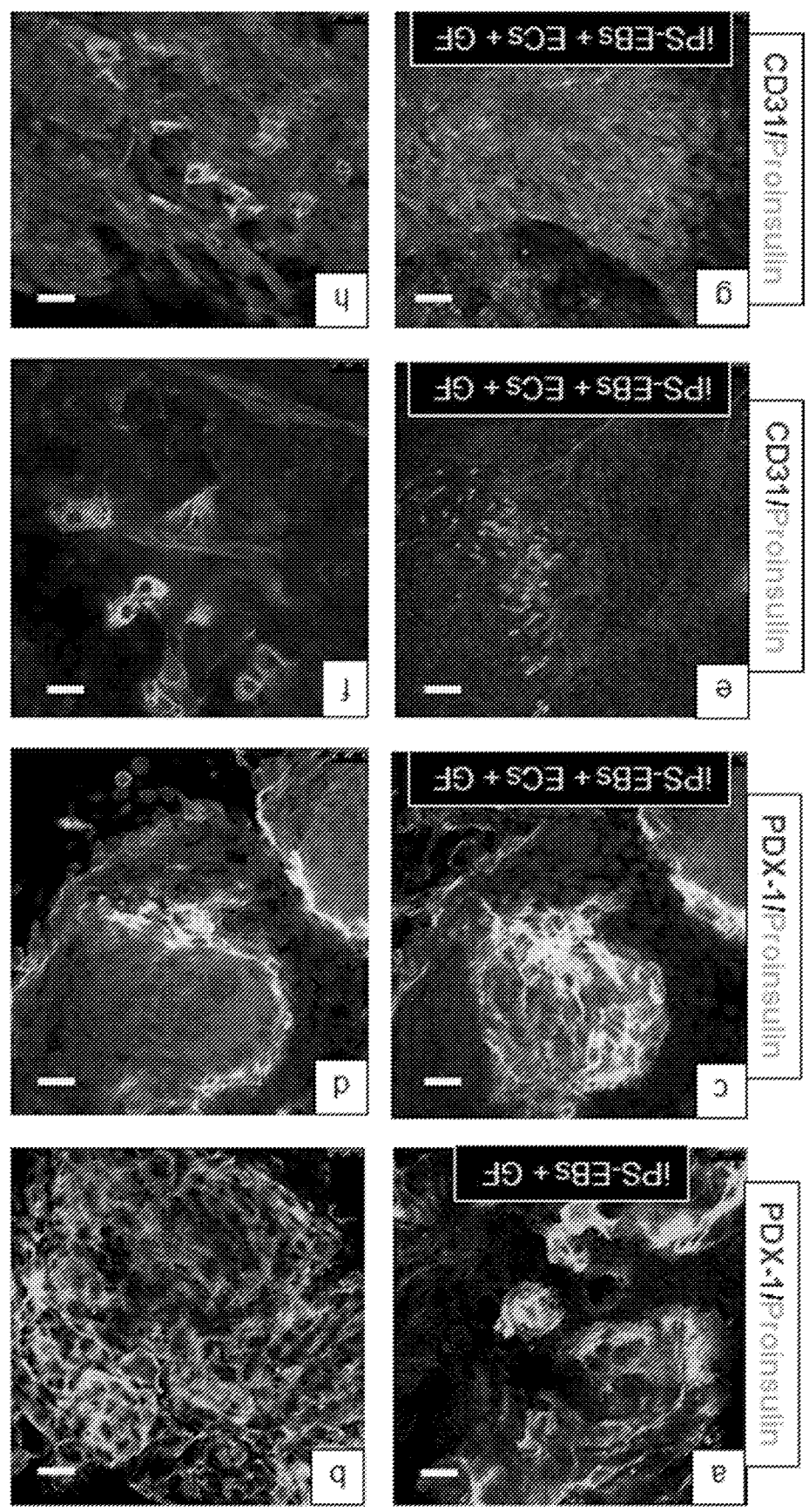
FIG. 18. Co-expression of PDX-1 and proinsulin in cells from embryoid bodies (EB) in close proximity to blood vessels. Optical sections obtained by confocal microscopy in cell clusters co-stained for proinsulin (green) and PDX-1 (red) in EBs cultured alone (a and b) or co-cultured with ECs (c and d). Lower (e) and higher (f) magnification of proinsulin positive cells in close proximity to formed blood vessels. Lower (g) and higher (h) magnification o proinsulin positive cells mixed with CD31 positive cells. (a, b, c, d, f, h) Bar=25 µm. (e, g) Bar=150 µm.

Cell Cluster Formation of Proinsulin and PDX-1 Double Positive Cells is a Dominant Structure in Co-Cultured iPSC-EBs and Starts Close to Internal Blood Vessels However, in vitro formation of islet structures using embryonic stem cells remains a stiff challenge. We observed that the proinsulin and PDX-1 double positive cells within iPSC-EB co-cultured with HMECs tended to form islet-like structures. Confocal images at different focal planes revealed the shape of these structures formed in either EBs cultured alone (FIG. 5a, b) or co-cultured with HMECs (FIG. 5c, d). All of these EBs were treated with growth factors. Remarkably, only EBs co-cultured with ECs co-expressed proinsulin and PDX-1 (FIG. 5c, d). By contrast, EBs cultured alone did not express PDX-1 (FIG. 5a, b). In addition, proinulin and PDX-1 double positive cells started developing close to blood vessels (FIG. 5e, f). In some clusters proinsulin positive cells were intermixed with CD31+ cells (FIG. 5g, h). These data suggest that islet-like structures, that express proinsulin and PDX-1, are developing in co-cultured EBs and that external and internal ECs promotes this islet formation. Additional results confirming these findings are shown in FIG. 18.

Example 17

Figure 6:
FIG. 6. Gene expression profile of iPSC-derived EB cultured alone or with ECs cells before and after cell sorting. (a) iPSC-derived EBs co-cultured with endothelial cells and treated with growth factors (blue bars) or cells not co-cultured (black bars). (b) iPSC-derived EBs co-cultured with ECs and treated with growth factors (blue bars) or cells not co-cultured with ECs (black bars). $P<0.05$ Bar=100 µm.
Figure 6:
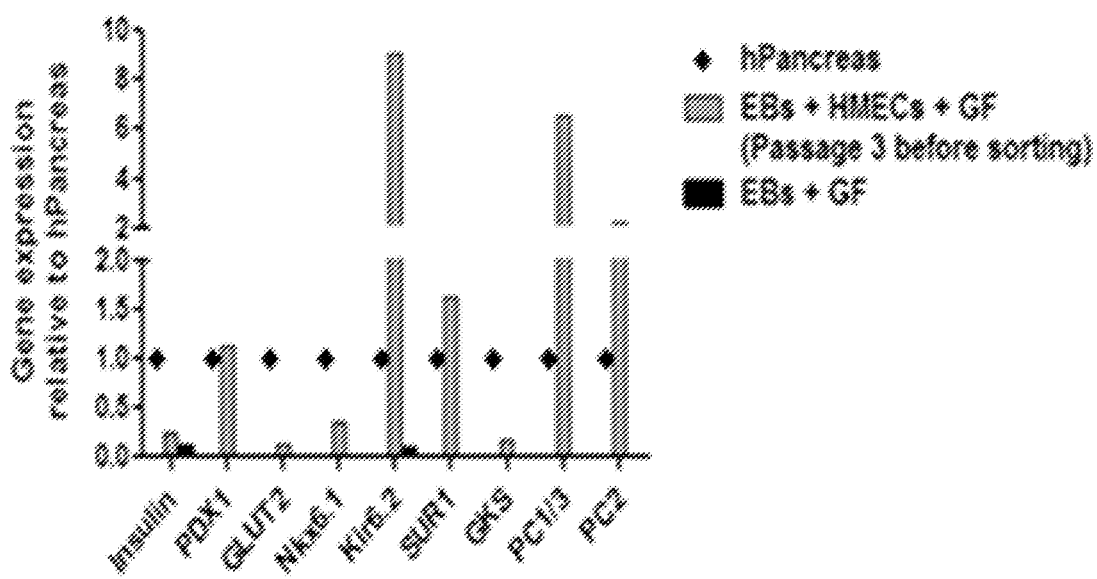
Figure 6:
Figure 6:
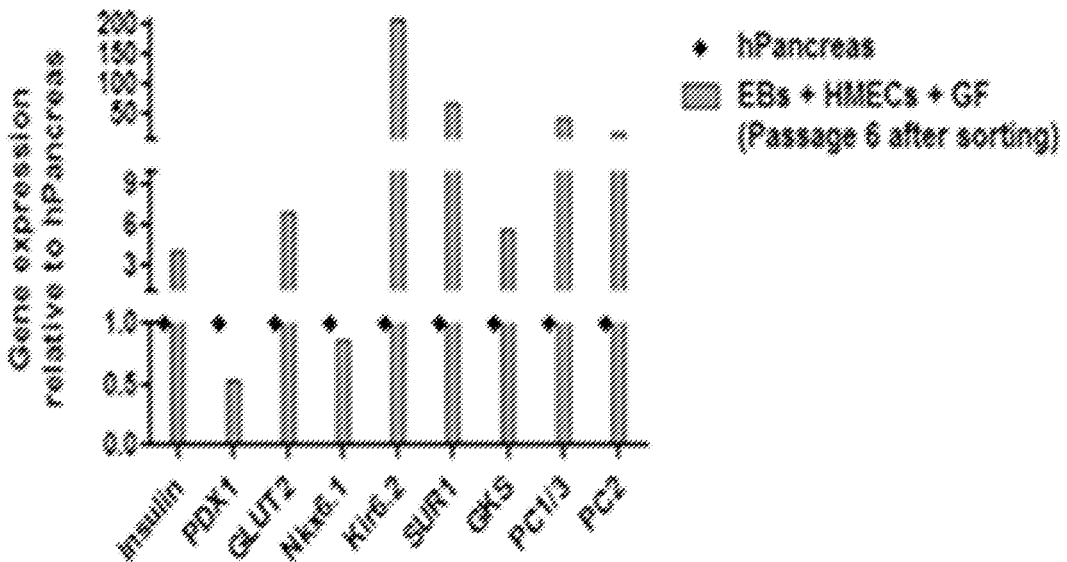

Gene Expression of Pancreatic Markers in Cells Derived from iPSCs Co-Cultured with HMECs To corroborate the ICC and FACS observations, we analyze the cells by qRT-PCR. Upregulation of beta-cell markers was observed in both unsorted and sorted cells (FIG. 6a, b). However, higher expression of beta-cell markers was found in sorted cells (except for PDX-1). Human pancreas was used as control to test pancreatic marker expression (FIG. 6a, b). Evaluation of pancreatic progenitor and islet markers was also carried out.

Figure 7:
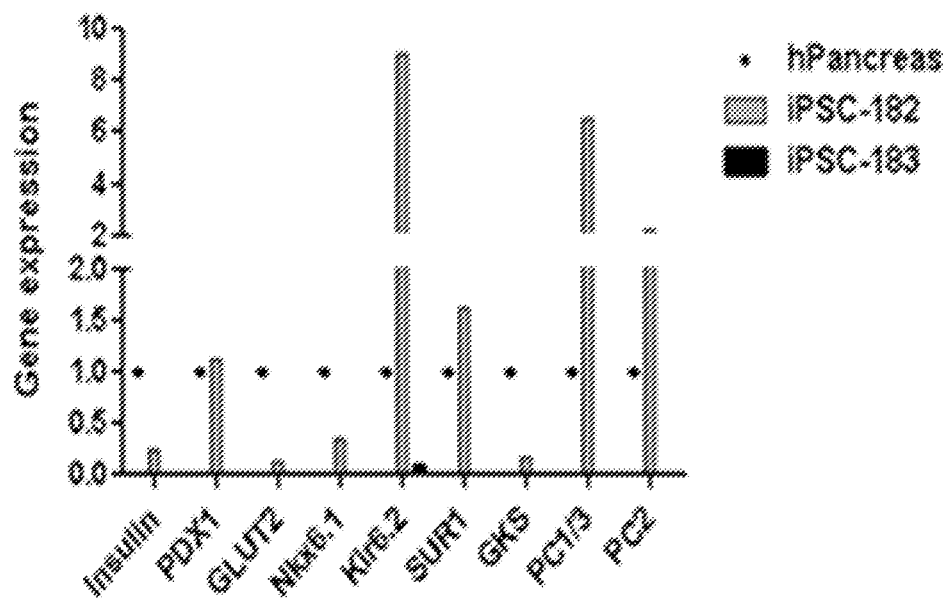
FIG. 7. Gene expression profile of iPSC-derived EB cultured alone or with ECs cells. Cells cultured in the presence of endothelial cells (iPSC-182) or without (iPSC-183) were compared to human pancreas tissue (hPancreas) and displayed (a) elevated expression of markers associated with beta-cells (b) enhanced levels of key markers associated with islet cell function (c) elevated levels of markers associated with pancreatic progenitors and (d) enhanced expression of BMP-related markers. $P<0.05$.
Figure 7:
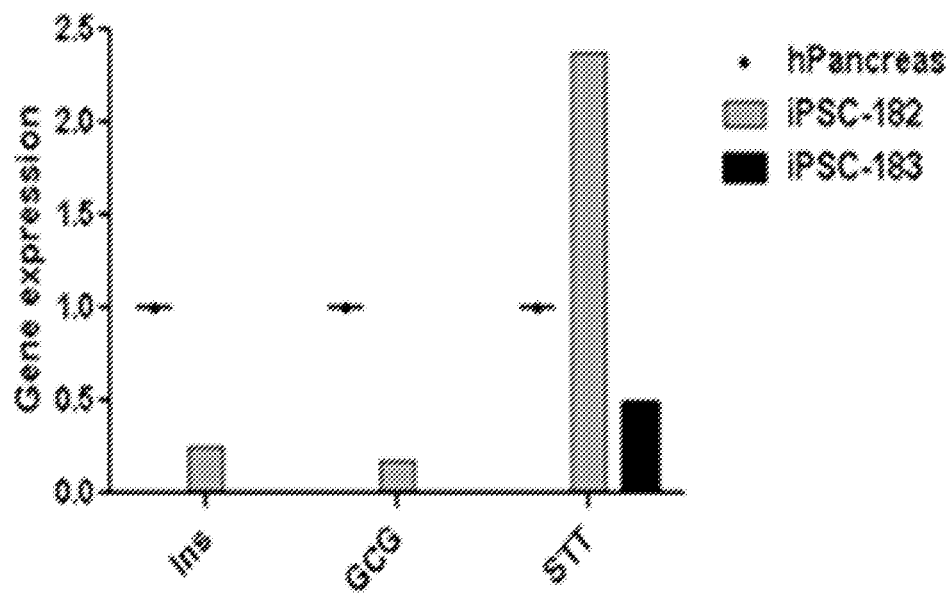
Figure 7:
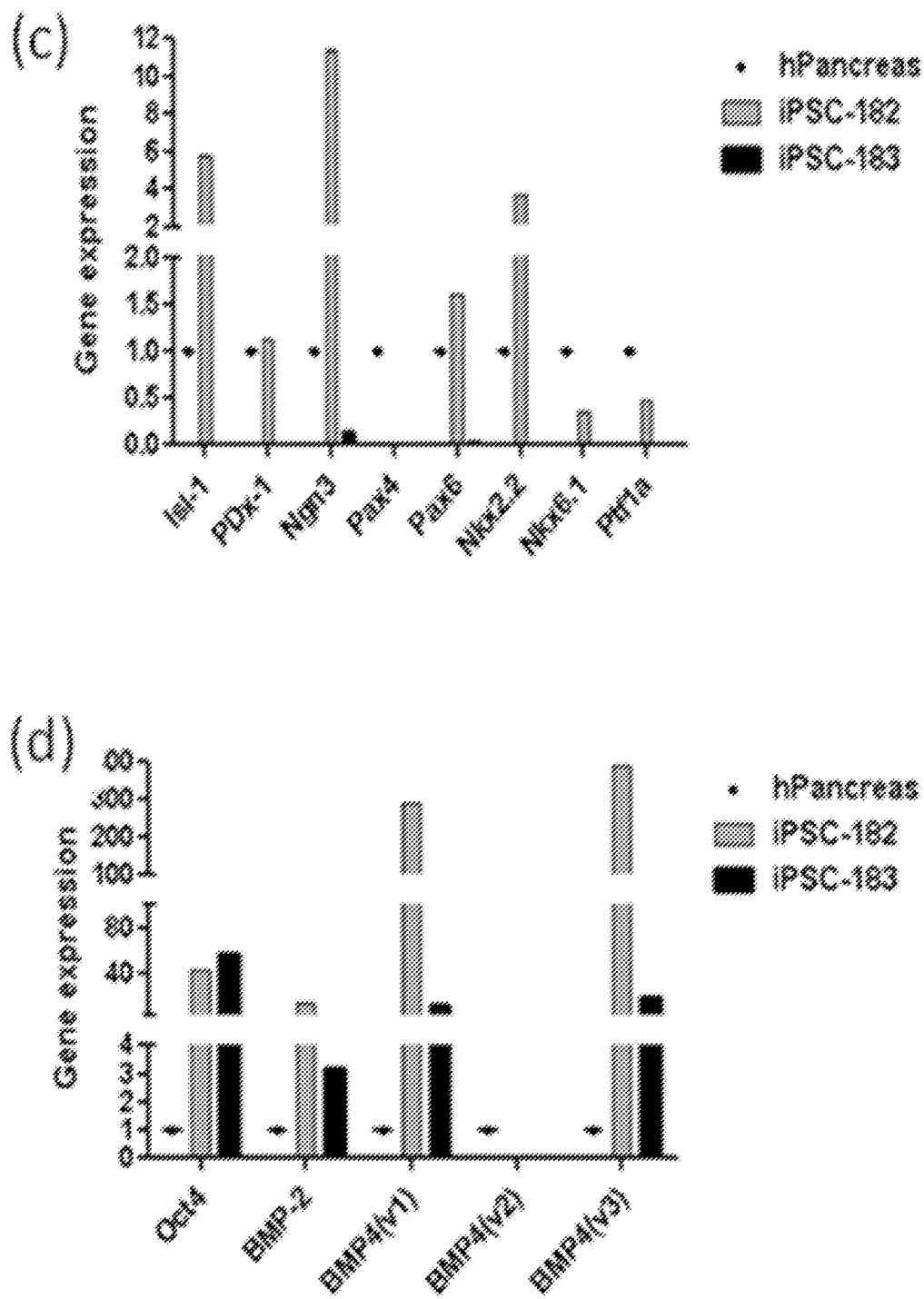

For example, additional experiments extended these results by measuring beta-cell markers, pancreatic progenitors, BMP-related markers, and functional markers, together demonstrating wide consistency of the differentiated cell lineage. Cells cultured in the presence, or without ECs were compared to human pancreas tissue and displayed (FIG. 7a) elevated expression of markers associated with beta-cells (FIG. 7b) enhanced levels of key markers associated with islet cell function, such as insulin and glucagon (GCG), somatostatin (STT), (FIG. 7c) elevated levels of markers associated with pancreatic progenitor cells and (FIG. 7d) enhanced expression of BMP-related markers. These data clearly demonstrate that HMECs enhance the differentiation of iPSCs toward pancreatic lineage, as well as BMP-related proteins.

Example 18

Isolation, Expansion, and In Vitro Function of Insulin-Producing Cells Derived from iPSCs Co-Cultured with HMECs For isolation and characterization of beta-cells from the co-cultures, the inventors relied upon the fluorescent dual-reporter system described above. Cells were infected with lentivirus carrying a mCherry-encoding plasmid driven by rat insulin promoter and GFP driven by ubiquitin, the plasmid organization is shown in FIG. 19k. After sorting, a weak expression of mCherry was observed in beta-cells (FIG. 8a, b, c, d).

Figure 8:
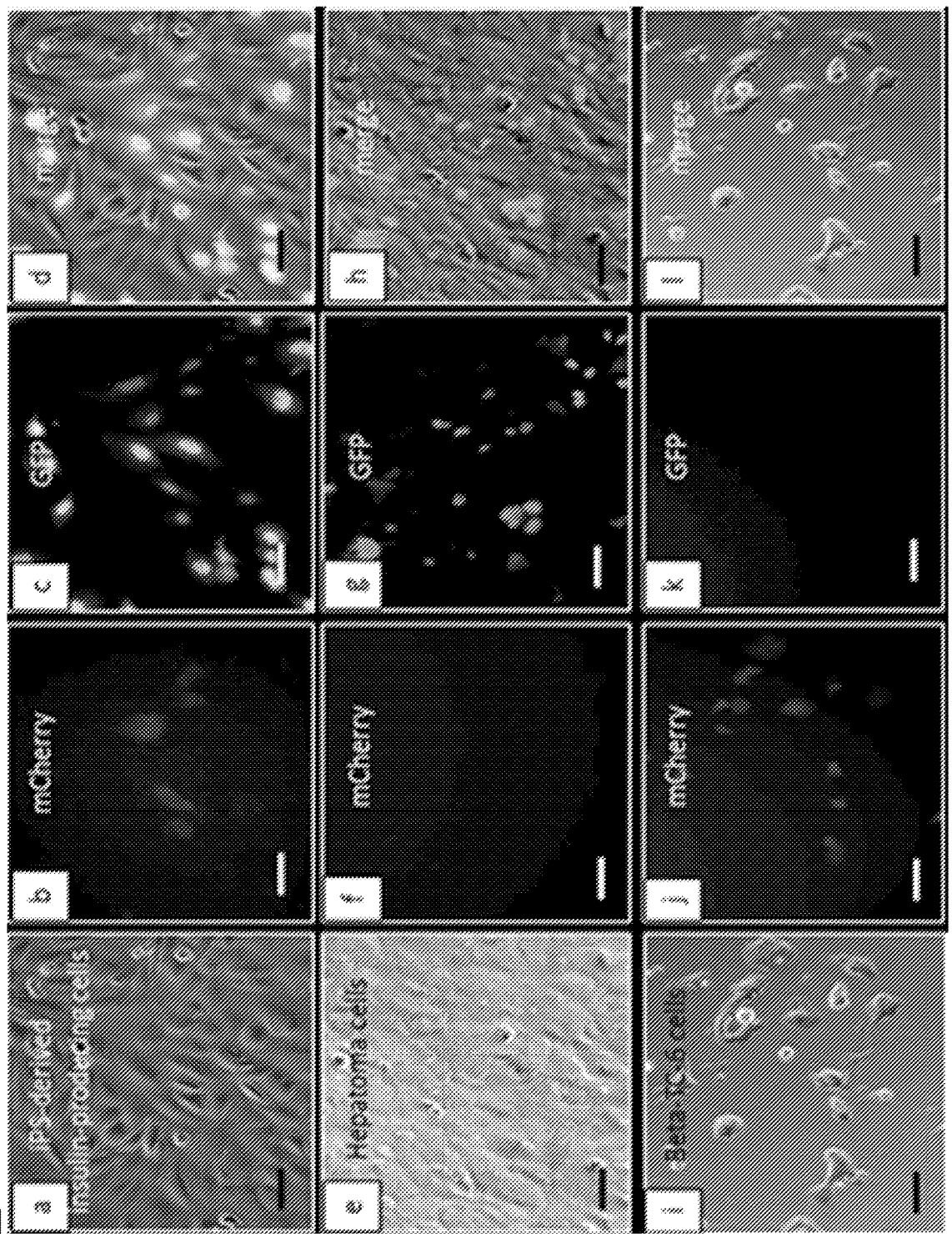
FIG. 8. Expression of a plasmid that carries mCherry (red) driven by insulin promoter and GFP (green) driven by ubiquitin promoter in iPSC-derived EBs after differentiation and labeling. (a) Cells derived from iPSC-EBs co-cultured with ECs (bright field). (b) The same cells expressing (b) mCherry, and (c) GFP. (d) Merged image. (e) Human hepatoma cells that do not express (f) mCherry but they do express (g) GFP. (h) Merged image. (i) Beta-TC-6 (mouse insulinoma cell line) that do express (j) mCherry but do not express (k) GFP. (l) Merge image.
Figure 9:
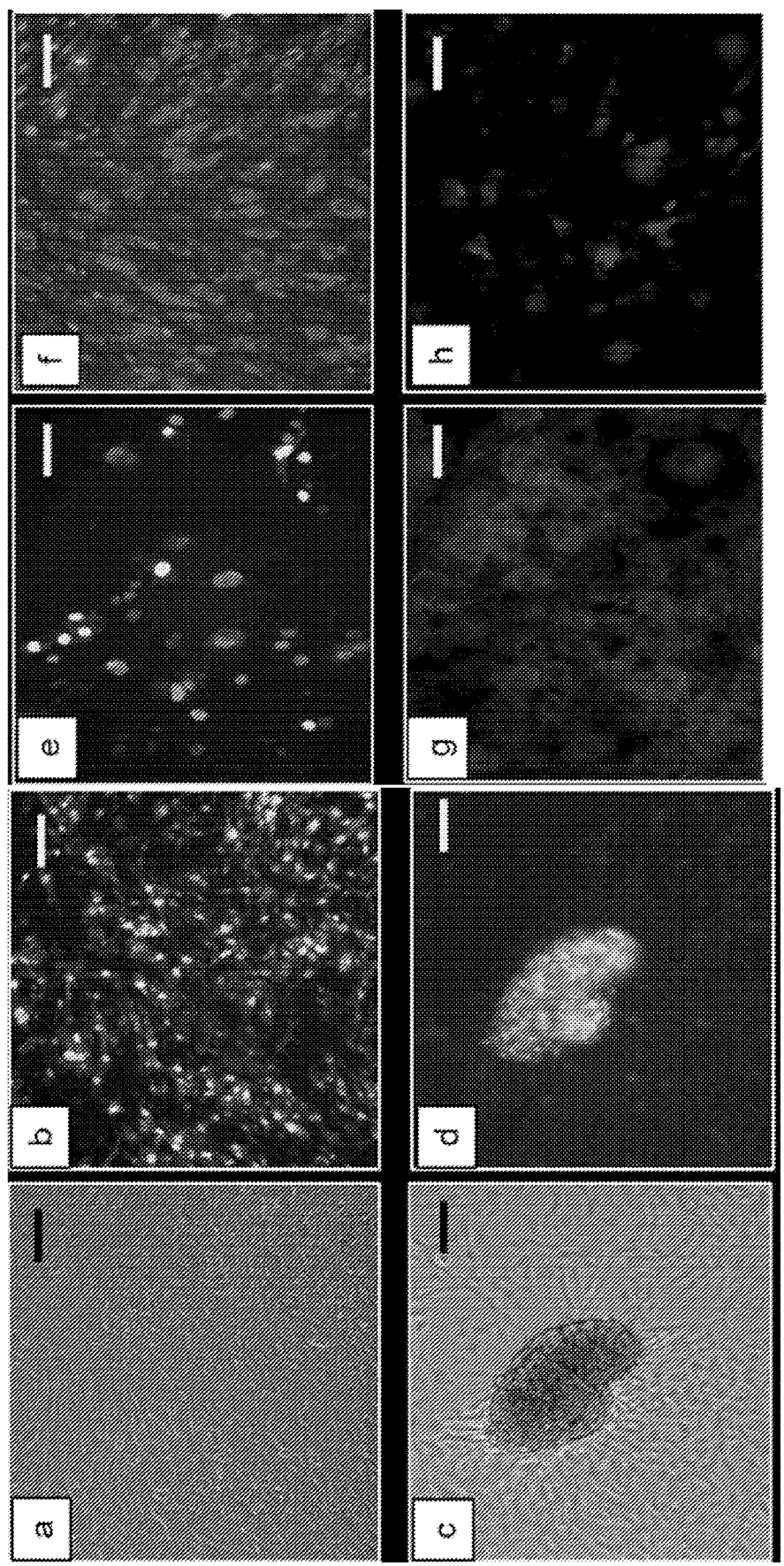
FIG. 9. In vitro expansion of mCherry positive cells. (a) iPSC-derived EB cells from cocultured were harvested and plated. They reached confluence after 7 to 10 days. (a) Bright field of the cells forming a monolayer. (b) Cells positive for insulin (red) and/or GFP (green) at passage 1. (c) Clusters composed of cells that co-expressed (d) insulin and ubiquitin at passages 3. (e) Cells that co-expressed both markers. (f) Confluent monolayer of cells positive for mCherry (red). (g) Cells that expressed human proinsulin C-peptide. (h) Cells that expressed urocortin 3.
Figure 19:
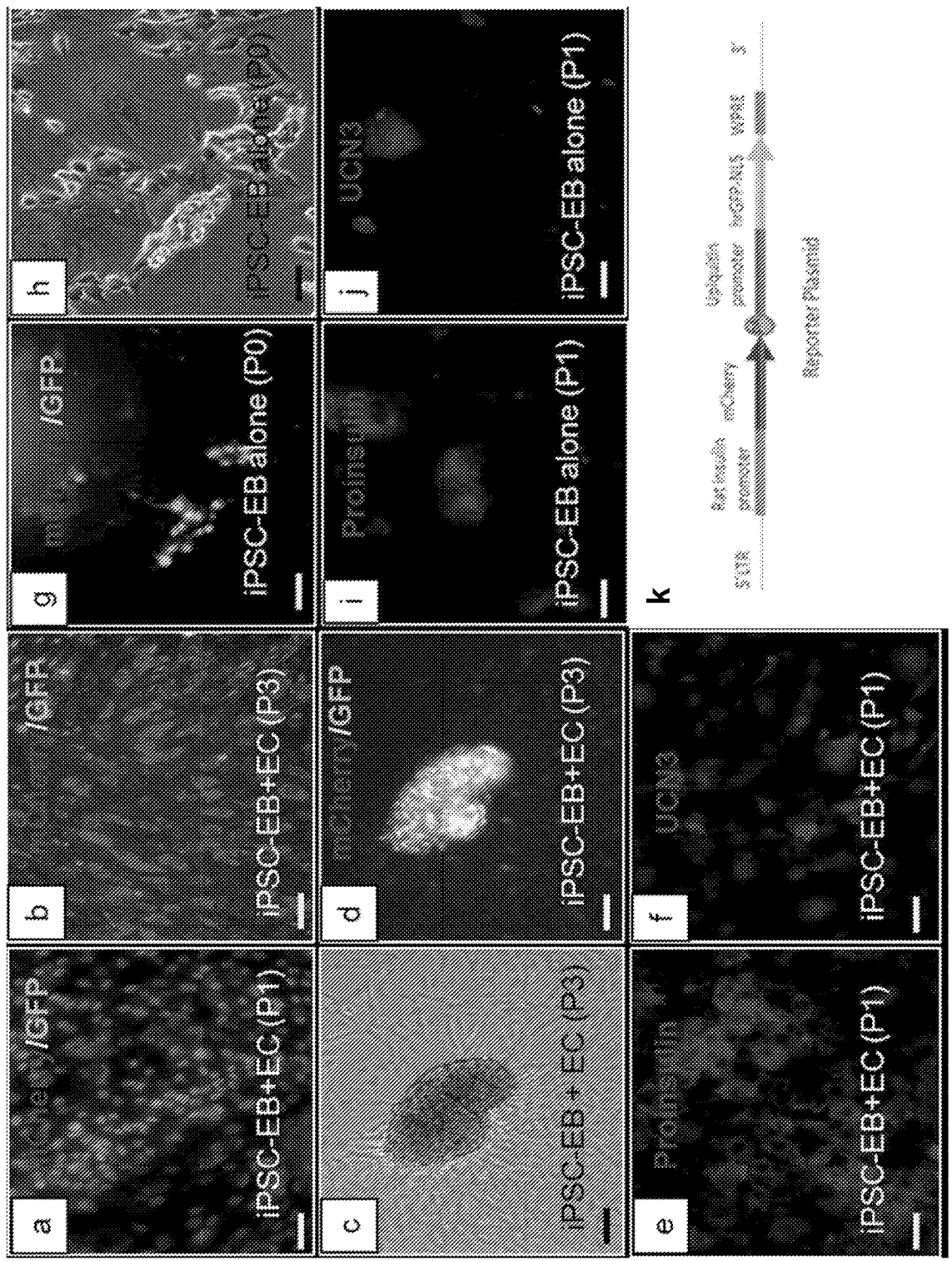
FIG. 19. Islet-like formation and urocortin 3 expression in isolated iPSC-beta cells. EB cells derived from co-cultures or EB alone were plated and transferred up to five passages. (a) Confluent cells derived from iPSC-EBs co-cultured with ECs. (b) Same cells sub-confluent or (c) confluent seen under fluorescent microscope. (d) Fluorescent islet-like cluster also seen in (e) bright field. (f) UCN3 or (g) proinsulin expression in EB cells derived from co-cultures. (h) Not co-cultured EB cells that did not survive for more than one passage. (i) mCherry, (j) proinsulin, or (k) UCN3 expression in cells derived from EBs cultured alone. (l) UCN3 expression in Beta-TC-6 as positive control. These cells also co-expressed proinsulin (not shown). (a, d, e, j, k, l) Bar=100 µm. (b) Bar=25 µm. (c, f, g, h, i) Bar=50 µm.
Figure 24:
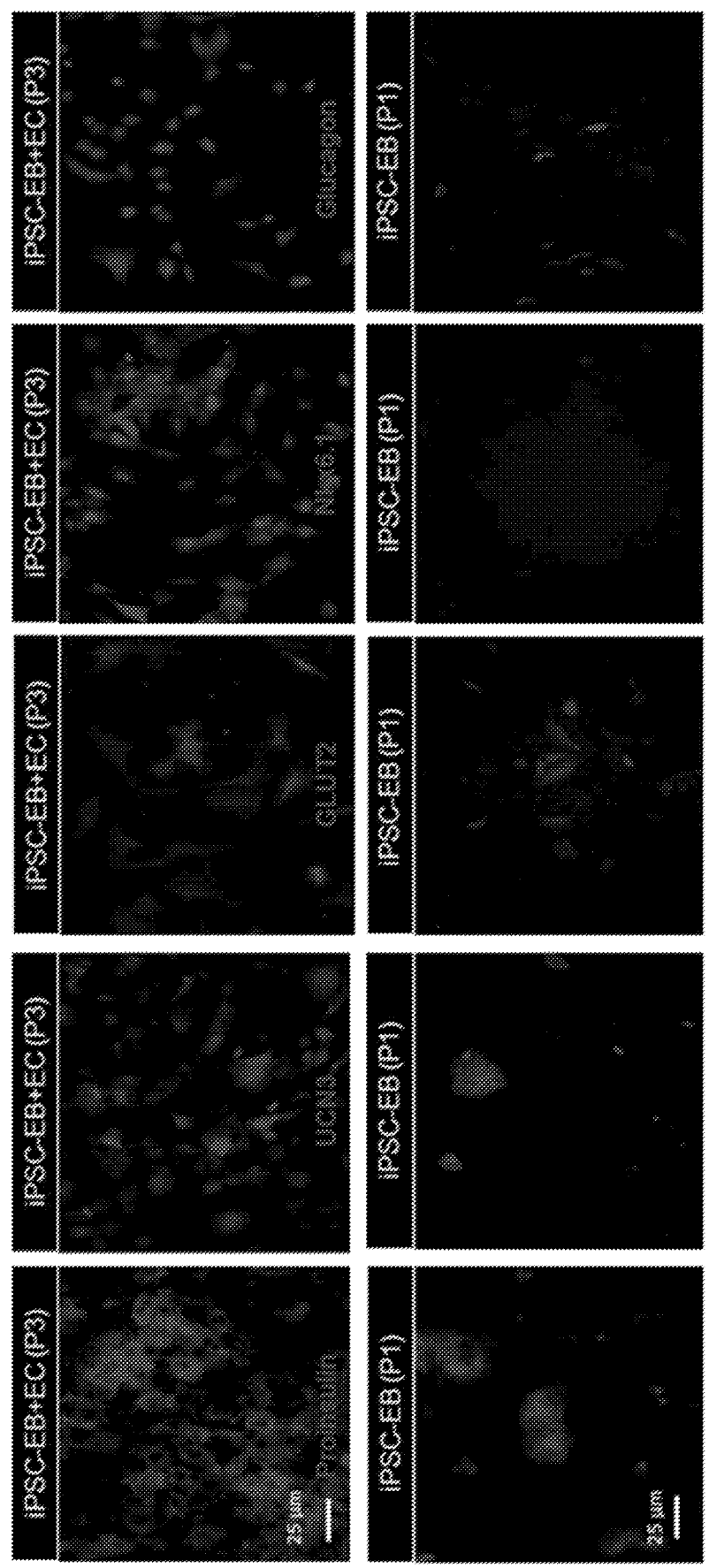
FIG. 24. Marker expression in differentiated cells. This includes (a) proinsulin, (b) urocortin-3 (UCN3), (c) GLUT2, and (d) Nkx6.1 in cells derived from EBs co-cultured with ECs. (e) Glucagon (expressed mainly in cells derived from DE co-cultured with ECs. Expression of (f) proinsulin, (g) UCN3, (h) GLUT2, and (i) Nkx6.1 in cells derived from EBs cultured alone. (j) Glucagon (in cells derived from DE cultured alone). Cells stained with Alexa 555 as secondary antibody. Scale bar=25 μm.
Figure 25:
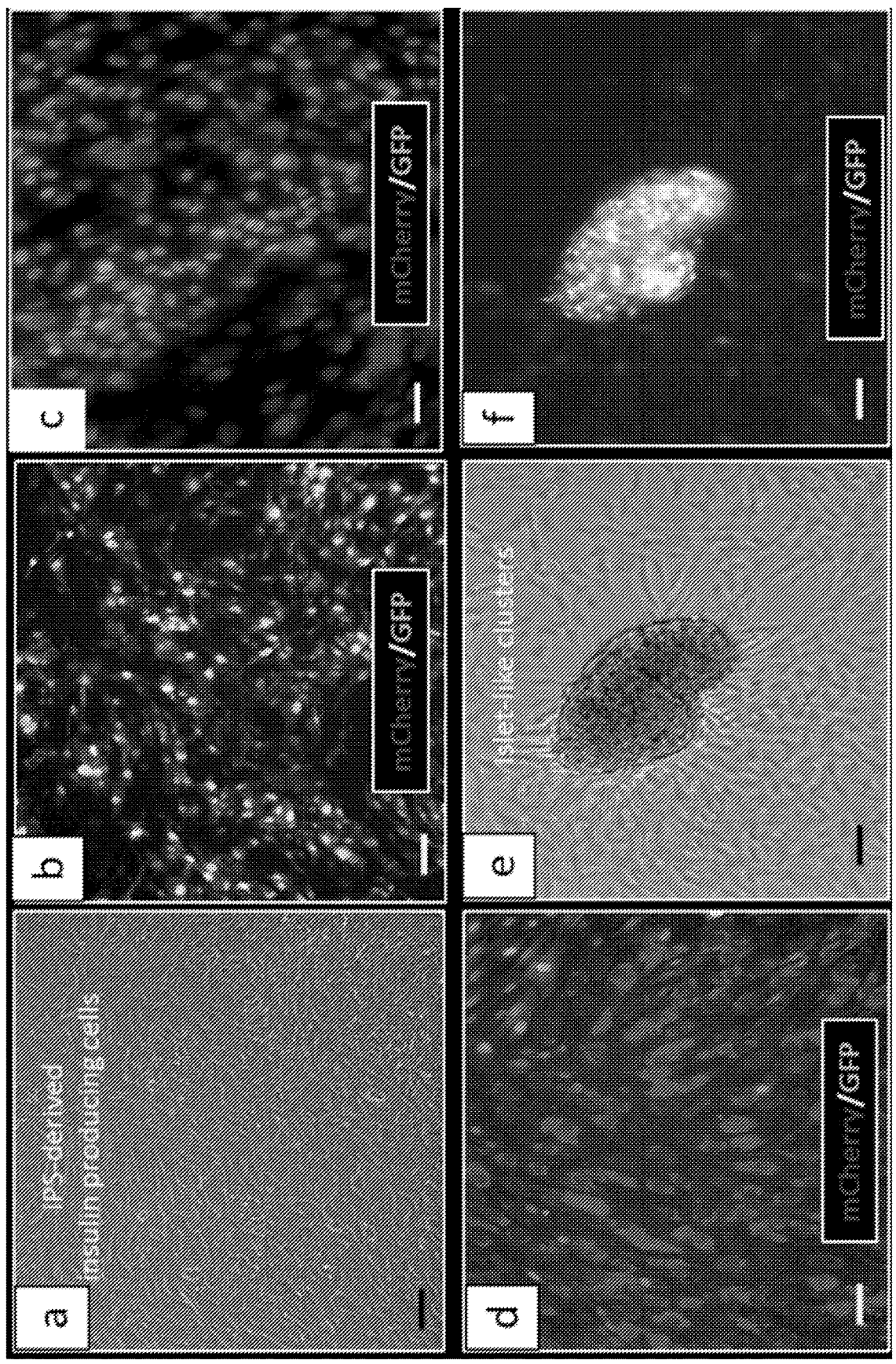
FIG. 25. Expansion of beta cells (mCherry positive) derived from hiPSCs. After sorting, the mCherry positive cells were cultured in one well of a 24 well plate pre-coated with collagen-laminin with EC-conditioned media. (a) iPSC-derived beta cells at passage 1 after sorting in a phase contrast field. (b) Same field using a fluorescent microscope. (c) Higher magnification of these cells. (d) Same cells observed in 'c' after 10 days in culture. (e, f) At passage 3, some of these cells tended to form islet-like clusters spontaneously. (a, b, e, f) Scale bar=100 μm, (c) Scale bar=25, (d) Scale bar=50 μm.
Figure 26:
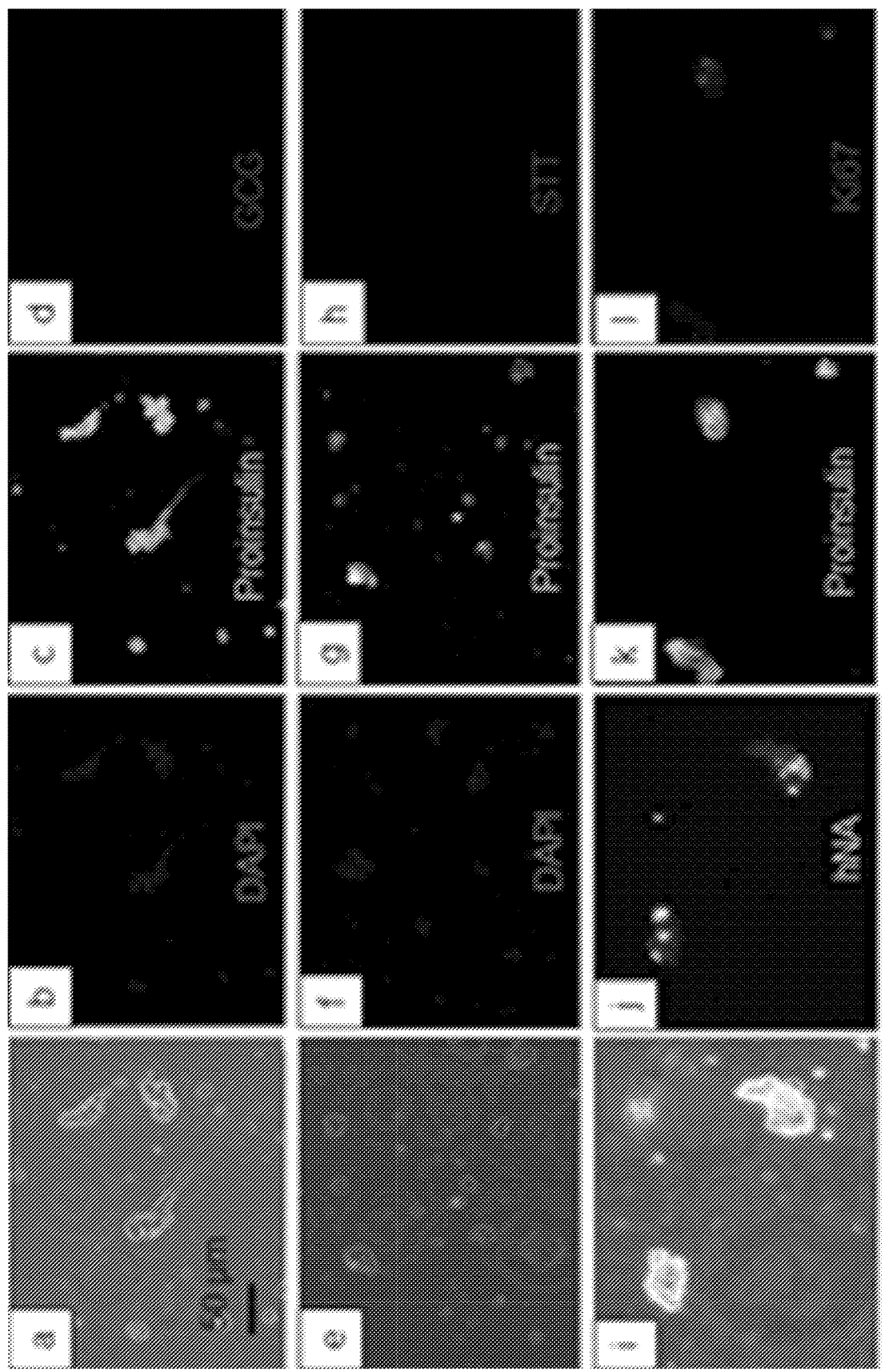
FIG. 26. Morphology of differentiated cell and reporter gene expression. (Left) Islet-like clusters at passage 3-5 plated on flasks pre-coated with collagen-laminin. (a, e, i) Beta-cell clusters observed with phase contrast. (b, 0 Cells stained to DAPI. (c, g, k) Cells stained to proinsulin. (d) Same cells in 'c' stained to glucagon (GCG). (h) Same cells in 'g' stained to somatostatin (STT). (j) Cells stained to human nuclear antigen. (l) Cells stained to Ki FIG. 27. Co-expression of proinsulin, and PDX-1 in definitive endoderm (DE) cells. DE cells (CXCR4+) treated with BMPs and evaluated by FACS (a) control. (b) Cells treated with pancreatic differentiation factors (GF). (c) Cells treated with EC-conditioned medium (EC-CM). (d) Cells treated with combination of BMP-2 and -4.67.

As expected, liver cells (hepatoma cell line) did not express mCherry but they expressed GFP (FIG. 8e, f, g, h). Beta-TC-6 cells expressed mCherry (FIG. 8i, j, k, l). These facts confirm that the plasmid is expressing mCherry driven by insulin promoter. Expression of mCherry and GFP became stronger in sorted cells as soon as they were transferred (FIG. 9a, b). At passage three, some islet-like clusters were observed in culture (FIG. 9c, d). mCherry positive cells also expressed GFP at early passages (FIG. 9e). However, lower GFP expression was observed along with higher mCherry expression in sorted cells (FIG. 9f). These cells also co-expressed proinsulin (FIG. 9g) and urocortin 3 (FIG. 9h). Additional results confirming these findings are shown in FIG. 19. Further characterization of these cells is shown in FIGS. 24-26, as described.

Figure 10:
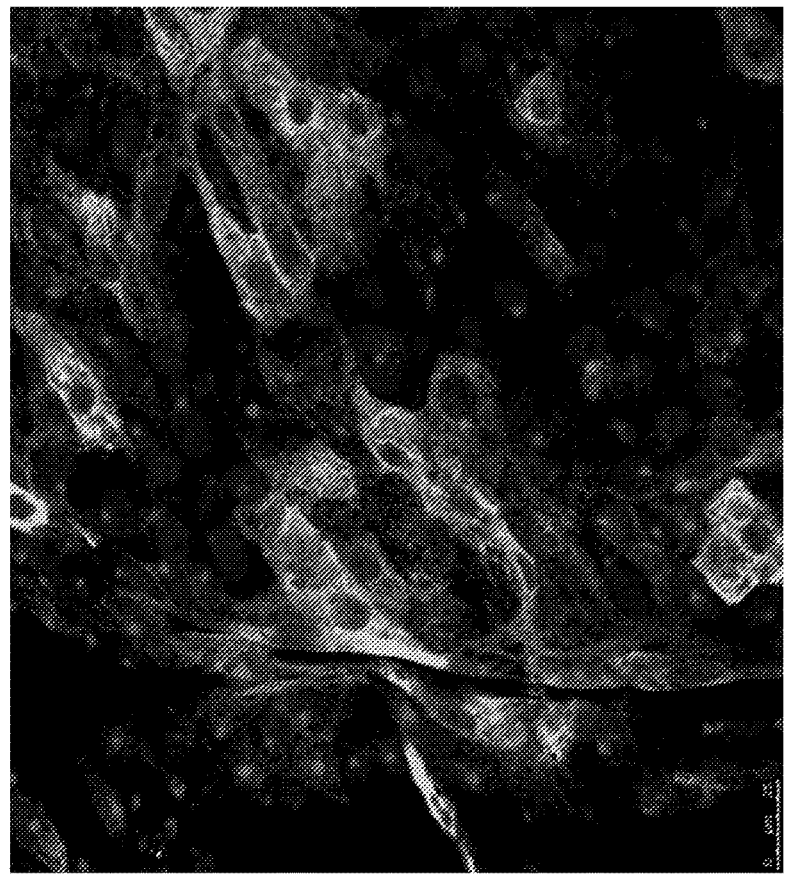
FIG. 10. Co-expression of pSMAD1/5/8 and Proinsulin in iPSC-EBs co-cultured with HMECs. Using the dual-reporter system described herein, 20-day old iPSCs differentiation via EB formation and co-culture with ECs resulted in visible pSMAD1/5/8 (red) and proinsulin (green) co-expression (a) lower magnification of intact cluster and (b) high magnification demonstrating clear co-expression within individual cells.
Figure 10:
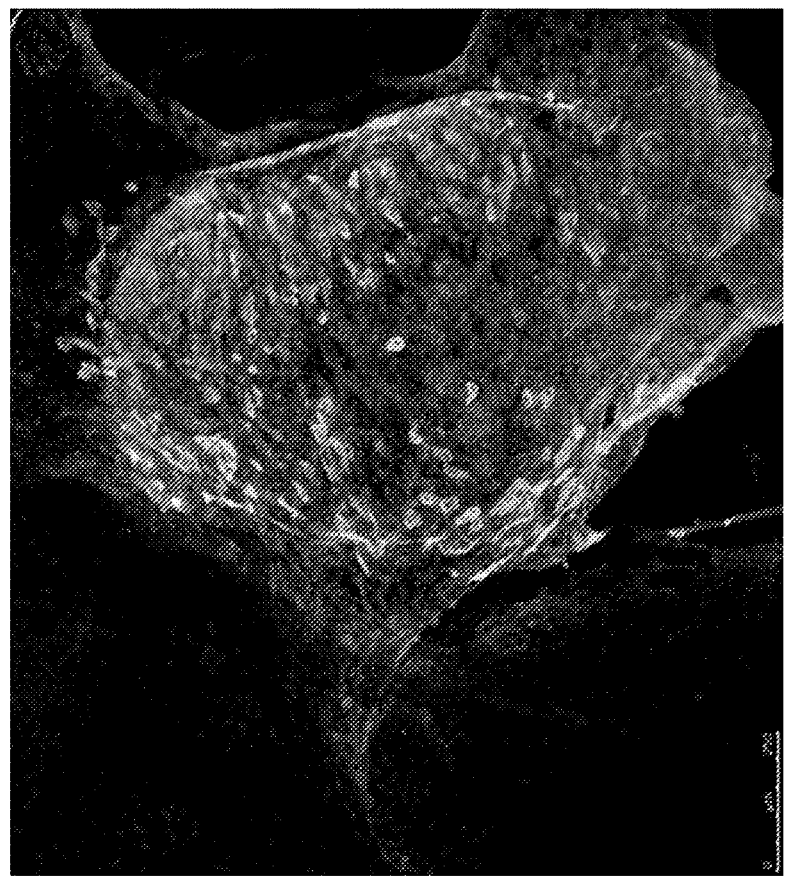

Confirming the role of BMP, WNT, and Activin-signaling pathways, was an observation of SMAD co-expression with pro-insulin. Using the dual-reporter system described herein, 20-day old iPSCs differentiation via EB formation and co-culture with ECs resulted in visible pSMAD1/5/8 (red) and proinsulin (green) co-expression (FIG. 10 a and b).

Figure 11:
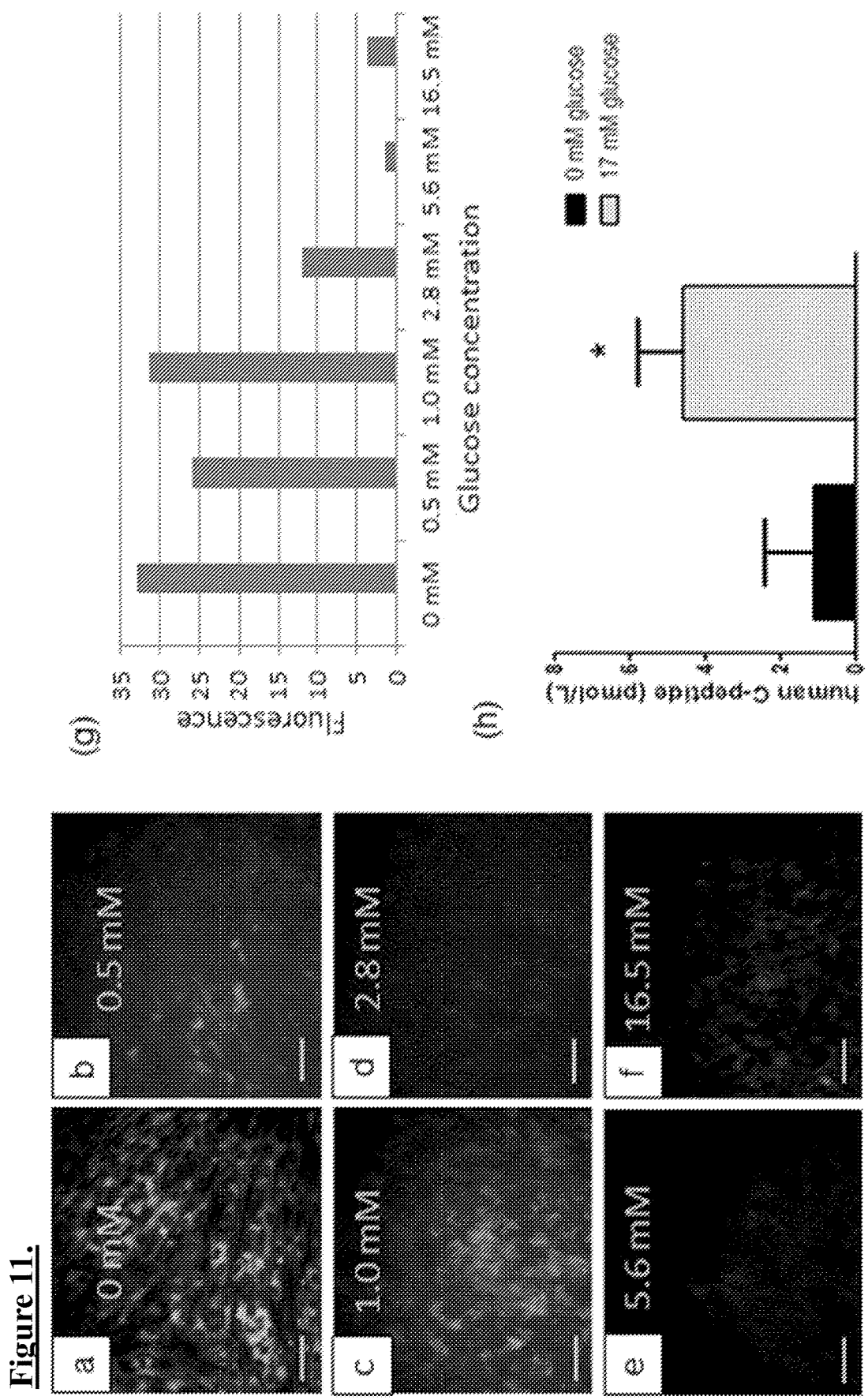
FIG. 11. Quinacrine secretion assay and in vitro measurement of human C-peptide in cells derived from co-cultures. (a) Quinacrine load for 30 min. Addition of (b) 0.5 mM, (c) 1.0 mM, (d) 2.8 mM, (e) 5.6 mM, and (f) 16.5 mM of glucose to these cells. (g) Relative fluorescence of the previous images quantified with the images tools of ImageJ software (see methods). (h) Quantification of human C-peptide in the culture medium of cells after a glucose challenge. (*) $P<0.05$.

Importantly, this data indicates that insulin-producing beta-cells derived from iPSCs can be expanded in vitro. To test the secretory capacity of these cells and the release of C-peptide in vitro, the cells were treated with quinacrine and quantification of human C-peptide was carried out by ELISA. Quinacrine accumulates in cell insulin granules after 30 min. At this point, maximum fluorescence was detected (FIGS. 11a and g). The fluorescence decreased as the glucose concentrations increased in the media (FIG. 11b-g).

Analysis by ELISA further indicated increase of human C-peptide in the media after a glucose challenge (FIG. 11h). These data indicates that sorted cells are able to secrete human C-peptide in vitro in response to different glucose concentrations.

Example 19

In Vivo Evaluation of the Functional Capacity of Insulin-Producing Cells Derived from iPSCs Co-Cultured with HMECs Sorted cells that exhibited the capacity to respond to glucose in vitro were expanded up to 10 passages. The karyotype of these cells was normal even after several passages. Then, these cells were transplanted under the kidney capsule of SCID mice.

For isolation of cells for use in transplantation, a digestive solution was prepared from 4% collagenase I and 4% BSA in PBS, with gels to added to a 15 mL Falcon tube that containing 5 mL of digestive solution, incubated in water bath at 37° C. for one hour, agitatig the tubes every 15 min. After one hour, tubes are centrifuged tubes at 1200 RPM for 5 min, followed by removal of supernatant and re-suspension of the pellet in a maintenance media (RPMI 1640 supplemented with 10% FBS, 200 mM L-alanyl-L-glutamine, 200 mM MEM non-esential amino acids, 200 mM sodium pyruvate, 100 μM beta mercaptoethanol, 100 mM penicillin-streptomycin, and 10 mM HEPES). The cell suspension (mix of EC, insulin-producing cells and other cells types) can be transplanted with about $3\text{-}5\times10^6$ cells per recipient.

Figure 12:
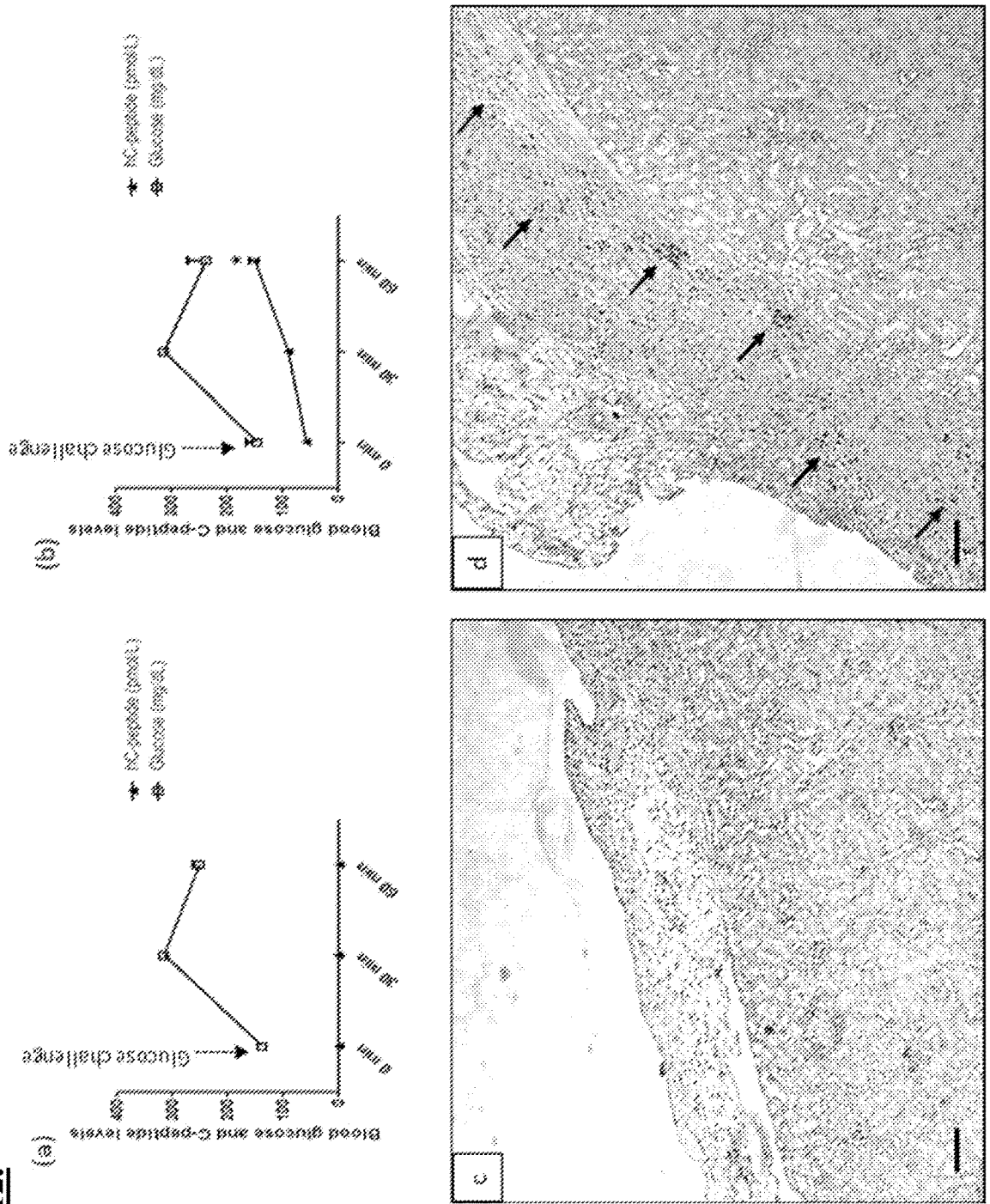
FIG. 12. Glucose tolerance test (GTT) and immunohistochemistry in mice grafted with beta-cells derived from co-cultures between iPSC-derived EBs and ECs. (a) Non-grafted mouse. (b) Grafted mouse. (c) Kidney and kidney capsule of a non-grafted mouse. (d) Kidney and kidney capsule of a grafted mice. (*) $P<0.05$, Bar=100

One hundred days after transplantation, a glucose tolerance test was performed and blood samples were obtained. After a glucose challenge control mice had a glucose increase from about 140 to 300 mg/dL with very low detection of human C-peptide (FIG. 12a). In contrast, grafted mice had about 60 pmol/L of human C-peptide at the time of glucose challenge and the C-peptide levels increased to about 150 and 90 pmol/L at 30 and 60 minutes respectively after the challenge (FIG. 12b). The kidneys were then harvested for IHC analysis. Normal kidneys had no evidence of insulin expression under the kidney capsule (FIG. 12c).

By contrast, abundant cells that expressed insulin were detected within a thicker kidney capsule of grafted mice (FIG. 12d). Other hormones such as glucagon and somatostatin were also detected in grafted mice (not shown). These data indicates that the insulin-producing cells maintain their functional phenotype in vivo and respond to glucose.

Example 20

Direct Differentiation into Definitive Endoderm

As described in FIG. 1a, an alternative approach to EB formation is direct differentiation of pSCs into definitive endoderm using combinations of growth factor cocktails, such as those targeting the BMP, WNT, and Activin signaling. This form of direct differentiation may be enhanced and improved using insights provided by the EB/EC co-culture studies. For example, demonstration of the important of extracellular matrix (ECM) proteins and three-dimensional "niche-like" structures.

Figure 13:
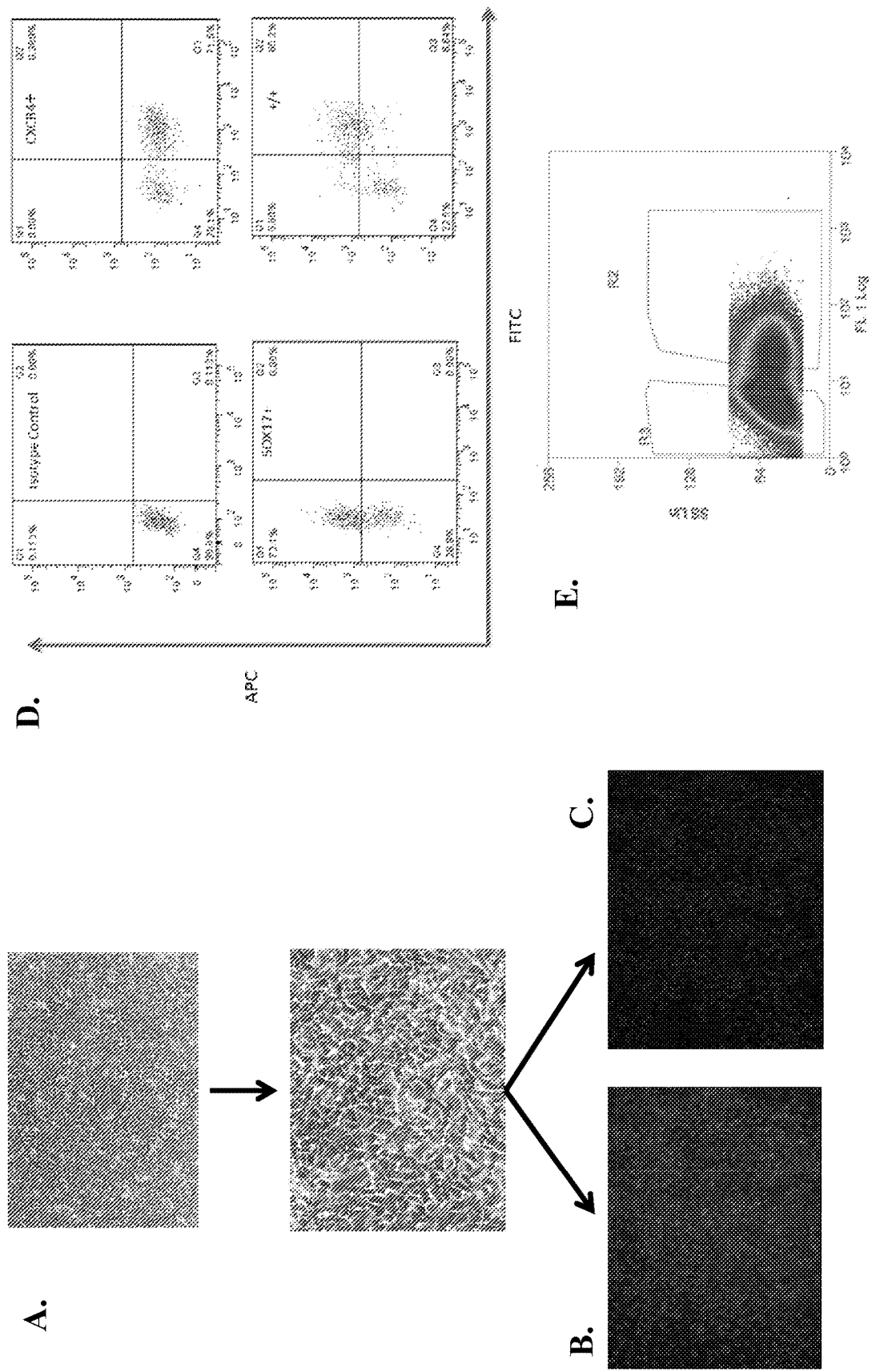
FIG. 13. Definitive endoderm derivation from iPSC and CXCR4 positive cell sorting. (a) definitive endoderm derived according to the described methods express both (b) CXCR4 and (c) SOX17 as can be seen under fluorescent microscopy (d) flow cytometry sorting of definitive endoderm via CXCR4 (FITC) or SOX17 (APC) expression (e) gating of cell populations shown in sub-figure (d).
Figure 14:
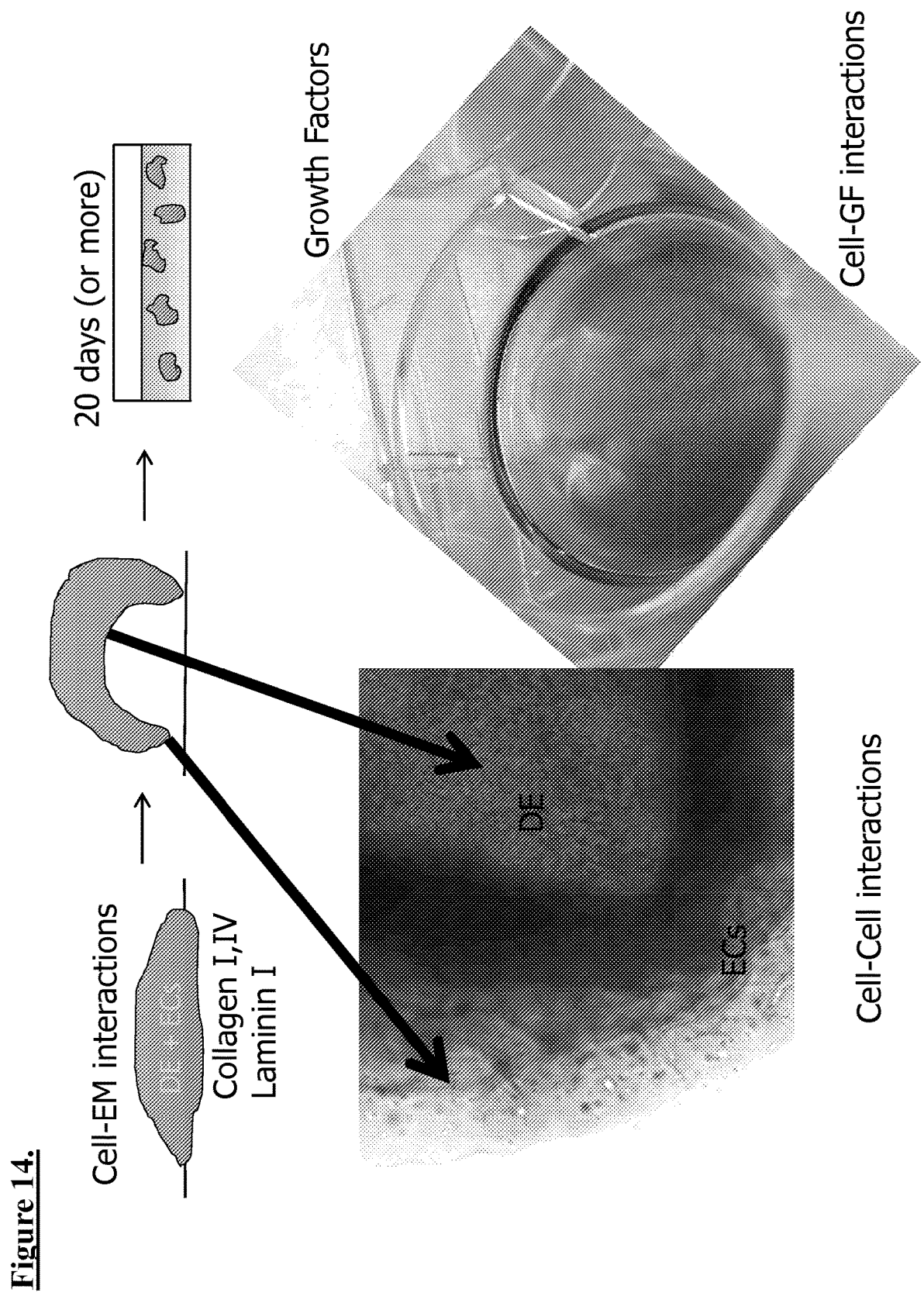
FIG. 14. Co-culture of DE+EC in collagen-laminin gels. In various embodiments, definitive endoderm can interact with extracellular matrix (EM) components such as collagen I, IV, and laminin I These cells can also be cultured in the presence of growth factors.

As a preliminary study, culturing of iPSCs in the presence of Activin A and Wnt3a allows formation of definitive endoderm from iPSCs. Cells differentiated in this manner (FIG. 13a) expressed definitive endoderm markers, CXCR4 (FIG. 13b) and SOX17 (FIG. 13c). Interestingly, dual selection for both markers indavated up to 65% of cells were dual positive for these markers using flow cytometry sorting (FIGS. 13d and e). Rather than relying on an EB formation step, definitive endoderm is then co-cultured with ECs to form a "niche-like" structure composed of definitive endoderm and endothelial cells, wherein such interactions between the two cell types are promoted by the described collagen I, IV, and Laminin I gel mixtures (FIG. 14). These cells can also be cultured in the presence of growth factors for maturation and functionalization, such as the multi-step cocktail growth factor approach described.

Example 21

Similarity to Human Islet Cells in Culture

Figure 15:
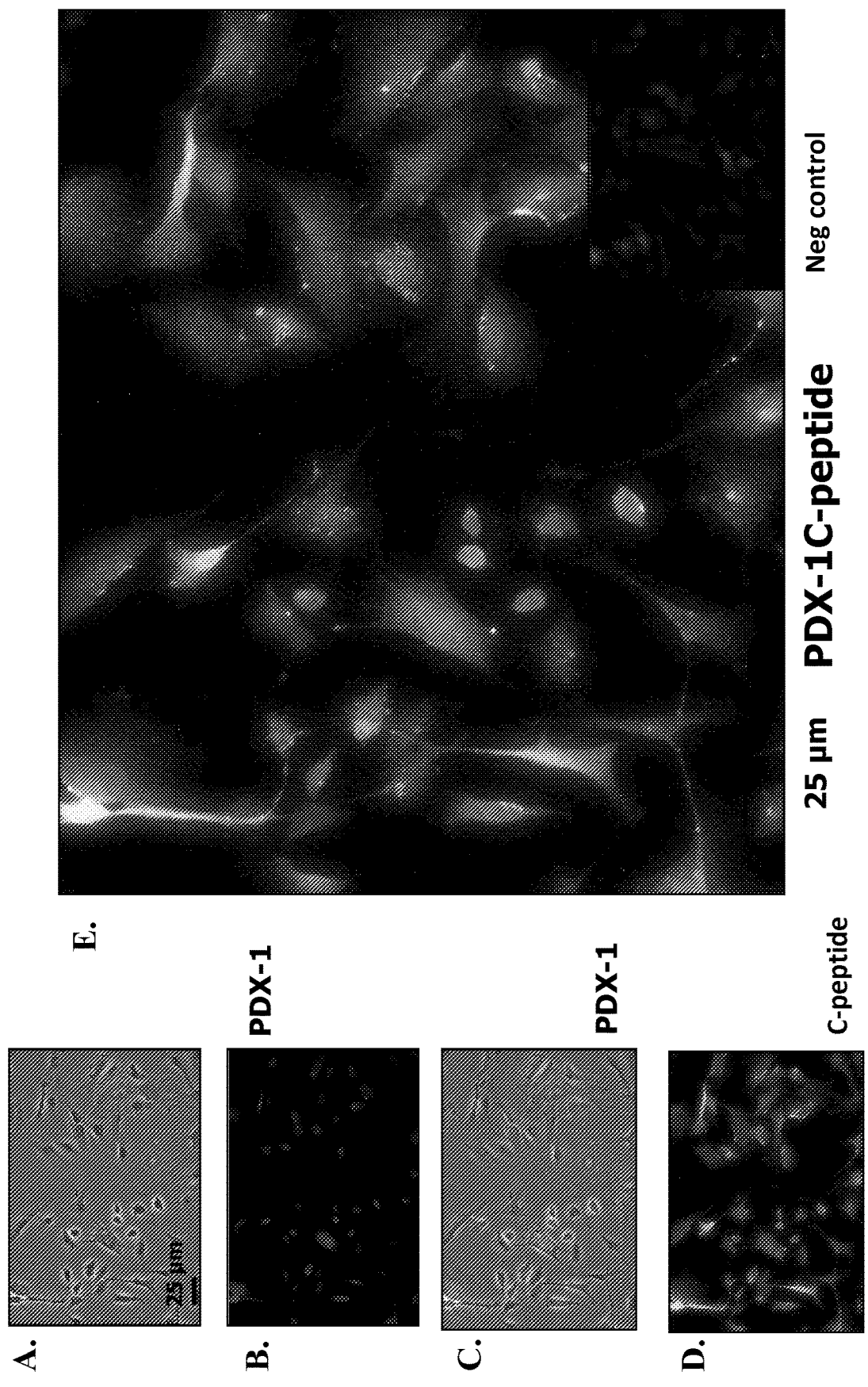
FIG. 15. Co-expression of C-peptide and PDX-1 in cells derived from sorted CXCR4+ definitive endoderm cells. CXCR4+ definitive endoderm (DE), expressing both C-peptide and PDX-1, can be sorted from differentiated iPSCs and visualized under (a) bright field magnification (b) PDX-1 marker expression (c) combination of bright field and PDX-1 (d) c-peptide detection (e) overlay of PDX-1/C-peptide expression in DE cells.
Figure 16:
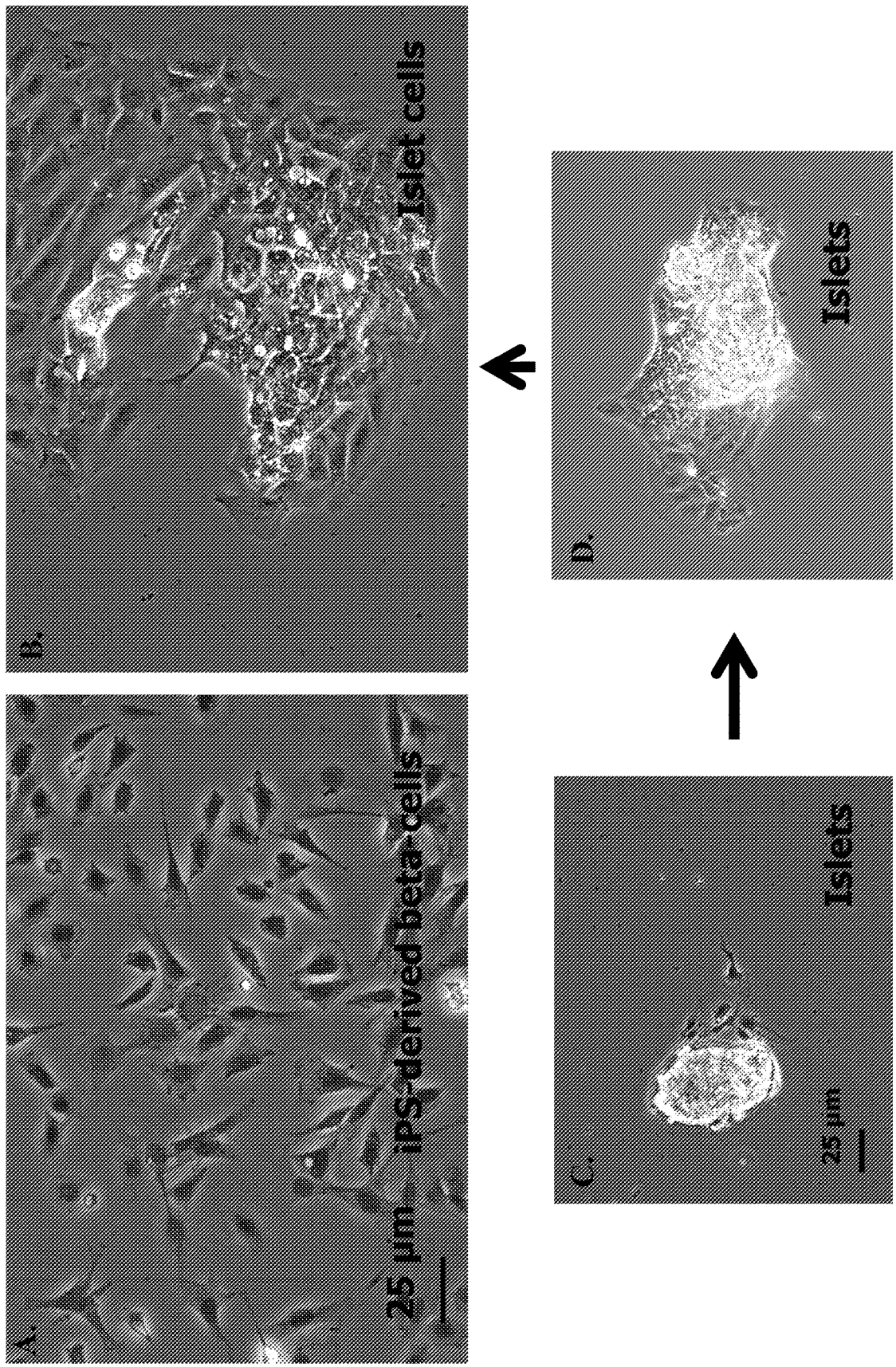
FIG. 16. Morphology of derived beta-cells from sorted CXCR4 compared to human islet cells. (a) iPSC-derived beta-cells, sorted via CXCR4 expression growth as a monolayer in culture similar to (b) human islet cells in culture (c) intact islets eventually (d) spread out and adopted the monolayer-like morphology shown in (b).

Cells derived via the direct differentiation method (FIG. 15a), expressed both PDX-1 (FIGS. 15b and c) and (FIG. 15d) C-peptide, with clear co-expression PDX-1/C-peptide expression in DE cells (FIG. 15e). Remarkably cells derived via direct differentiation possess a high degree of morphological similarity to human islet cells in culture. Following sorting of CXCR4+ cells, iPSC-derived beta-cells formed monolayers in culture (FIG. 16a), similar to (FIG. 16b) human islet cells in culture. Intact islet cells (FIG. 16c) eventually (FIG. 16d) spread out and adopted the monolayer-like porphology shown in (FIG. 16b).

Example 22

Alternative Sources of Endothelial Cells

In addition to the successful results described herein using HMECs, the methods can be extended to rely on endothelial cells isolated from different organs, such as endothelial cells from aorta, dermis, bladder, and coronary arteries. In an alternative approach, pluripotent stem cells themselves can be directed to differentiate into endothelial cells. In some applications, an autologous transplant system with patient-specific beta-cells could be established establishing using embryoid bodies with endothelial cells derived from pluripotent stem cells.

Example 23

Microarray Analysis of Isolation of Beta-Cells to Identify Unique Surface Marker Expression While the dual-reporter system described herein is useful for research applications for isolation and characterization of cells, therapeutic approaches would seek to avoid exposure to viral genetic material. In this regard, the dual-reporter system for the isolated cells can be subjected to analysis via microarrays to identify one or more surface marker proteins for cell isolation and purification. Identification of such a panel would allow isolation of a pure population of pancreatic beta-cells that can be used in human with type 1 diabetes mellitus (T1DM). Another alternative is the use of definitive endoderm cells that can be isolated based on the expression of CXCR4 surface antigen. In this case, viral infection is not necessary. This procedure will be more safe for future therapeutic uses.

Example 24

Study of the Influence of Endothelial Cells in the Proliferation and Survival of Pancreatic Beta-Cells Derived from Pluripotent Stem Cells after Transplantation Additional experiments can be performed in animals to evaluate the effects of endothelial cells in vivo after pancreatic beta cell (derived from iPSCs) transplantation. Since it has been reported that human islets survive better when they are transplanted with endothelial cells (Pan et al., 2011). In these experiments, the beta-cells derived from PSCs will be transplanted with different percentages of endothelial cells as shown in the next table.

TABLE 2

Percentages of transplanted cells including a combination of pancreatic beta-cells and endothelial cells (ECs)
Proportion of Transplanted Cells

| 0% ECs | 25% ECs | 50% ECs | 75% ECs | 100% ECs |
|---|---|---|---|---|
| 100% Beta-cells | 75% Beta-cells | 50% Beta-cells | 25% Beta-cells | 0% Beta-cells |
| 8 SCID mice | 8 SCID mice | 8 SCID mice | 8 SCID mice | 8 SCID mice |

At about 60-70 days post-transplantation the SCID mice will be treated with streptozotocin (SZT) for beta cell destruction. Ten mice will be used as controls in which the transplanted cells can be human islets.

Example 25

Purification of Definitive Endoderm Cells, Co-Culture with Endothelial Cells

In a modified application of the described techniques, definitive endoderm cells, from which pancreatic cells are generated, were purified using the below described protocol and subsequently co-cultured with endothelial cells in collagen gels for 20 days.

For this study, human pluripotent stem cell line (83iCTR-n) obtained from Cedars-Sinai Medical Center iPSC core were treated with factors to obtain definitive endoderm cells. While general procedures for obtain these cells has been reported before, a modified protocol was applied to obtain definitive endoderm cells as follows:
1. iPSCs are grown in NUNC 6-well plates. Once these cells re 80-90% confluent, they are harvested with Versene (Gibco by Life Technologies, Cat#15040-066) and washed with advance DMEM/F12 (CORNING, Cellgro, Cat#10-090-CV).
2. The clumps of iPSC re plated in collagen-laminin gels and treated for definitive endoderm differentiation using endoderm differentiation media during 5 days.
3. Day 1. RPMI 1640 (Gibco, Cat#11875-093)+Activin A (100 ng/mL) (Preprotech, Cat#120-14E)+Wnt3A (25 ng/ml)+L-ananyl-L-glutamine (final concentration 2 mM) (ATCC Cat #30-2115).

4. Day 2. RPMI 1640 (Gibco, Cat#11875-093)+Activin A (100 ng/mL) (Preprotech, Cat#120-14E)+2% FBS (Omega Scientific, Cat # FB-02).
5. Day 3. RPMI 1640 (Gibco, Cat#11875-093)+Activin A (100 ng/mL) (Preprotech, Cat#120-14E)+2% FBS (Omega Scientific, Cat # FB-02). 6. Day 4. The cells are harvested with 0.4% collagenase I (Worthington, Cat # S8B10327-210 u/mg) and a pure population of definitive endoderm cells re obtained using a surface marker CXCR.
7. Endothelial co-culture is then by plating the isolated definitive endoderm cells with human microvascular endothelial cells (HMEC) in a collagen-laminin gel for 20 days with or without growth factors.

Figure 17:
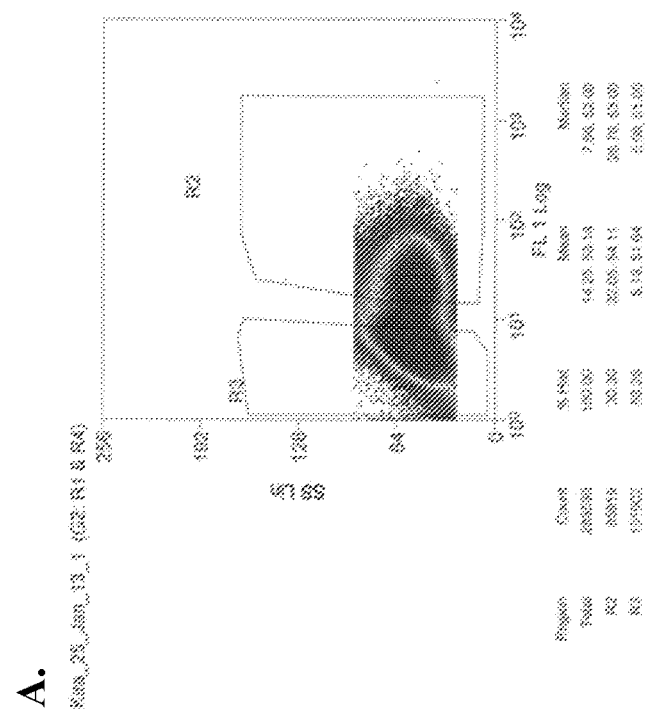
FIG. 17. Co-expression of C-peptide and PDX-1 in iPSC-derived definitive endoderm (DE) cells co-cultured with ECs. (a) FACS sorting of DE cells based on expression of CXCR4. (b) Co-expression of proinsulin (green) and PDX-1 (red) in beta cells derived from DE cells co-cultured with ECs in collagen-laminin gels and treated with pancreas differentiation factors. The inset shows DE cells no co-cultured with ECs treated with the same differentiation factors.
Figure 17:
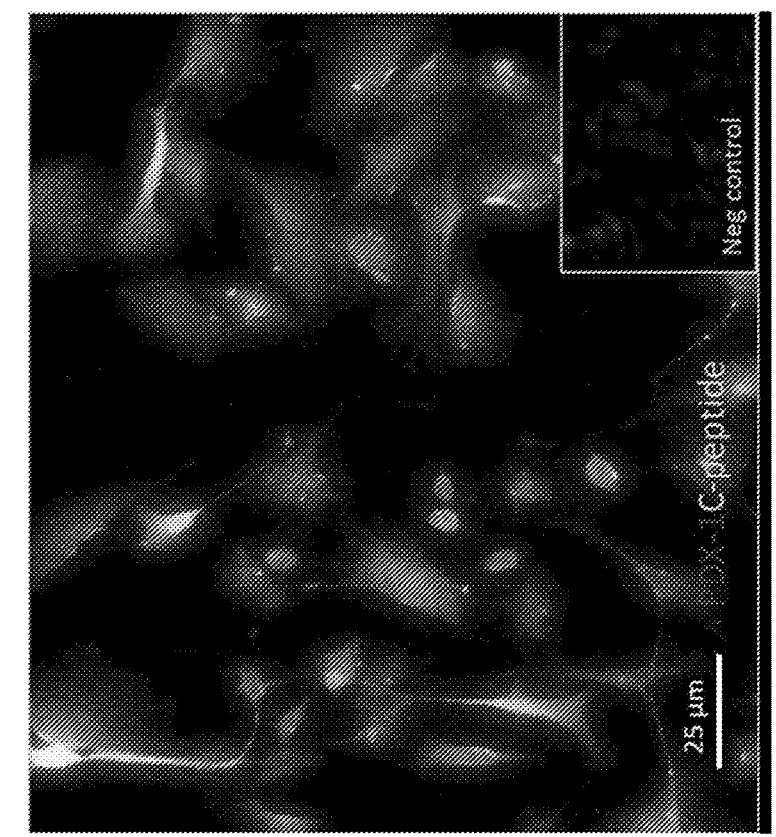

Via FACS sorting, approximately 30% of cells expressed definitive endoderm cell surface marker, CXCR4, as shown in FIG. 17(a). As shown in FIG. 17(b), the resulting cells co-express C-peptide and PDX-1, both important markers of beta cells. This highly purified population of cells and the population is more pure. Importantly, this approach demonstrates that the endothelial co-culture system provides consistent results for beta-cell differentiation, not constrained to the aforementioned EB-formation approach, but instead, extendible for cells obtained by other means, such as the definitive endoderm cell purification techniques described above. An additional advantage of this approach is removing the need for use of a virus to isolate cells.

Example 26

Bone Morphogenetic Protein (BMP) Pathway Activation in Pancreatic Beta Cells Differentiated from EBs Co-Cultured with Endothelial Cells Our previous studies indicated that enhancement of bone morphogenetic protein (BMP) pathway activation occurs at early stages during the co-culture system in mouse ESCs and that upregulation of BMPs in mouse EBs leads to enhancement of differentiation of cells derived from the three germ layers. Therefore, the Inventors assessed whether ECs co-cultured with human iPSCs had similar effects.

Figure 21:
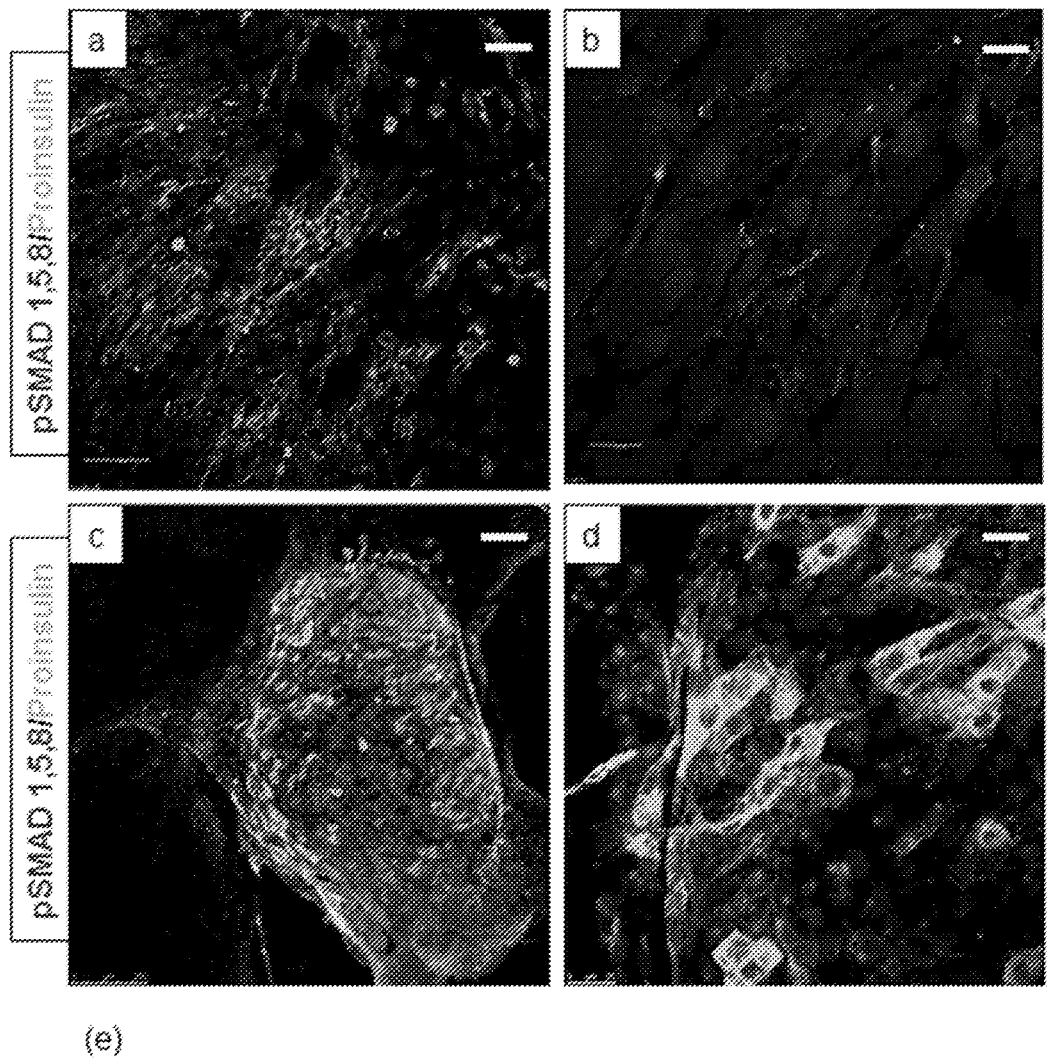
FIG. 21. Co-expression of proinsulin and phosphoS-MAD1/5/8 in beta cells derived from iPSCs. EB cells not co-cultured with ECs at (a) lower and (b) higher magnification. EB cells co-cultured with endothelial cells at (c) lower and (d) higher magnification. (e) Gene expression of OCT4, BMP-2, and BMP4 in EBs cultured alone or not co-cultured with ECs (HMECs).
Figure 21:
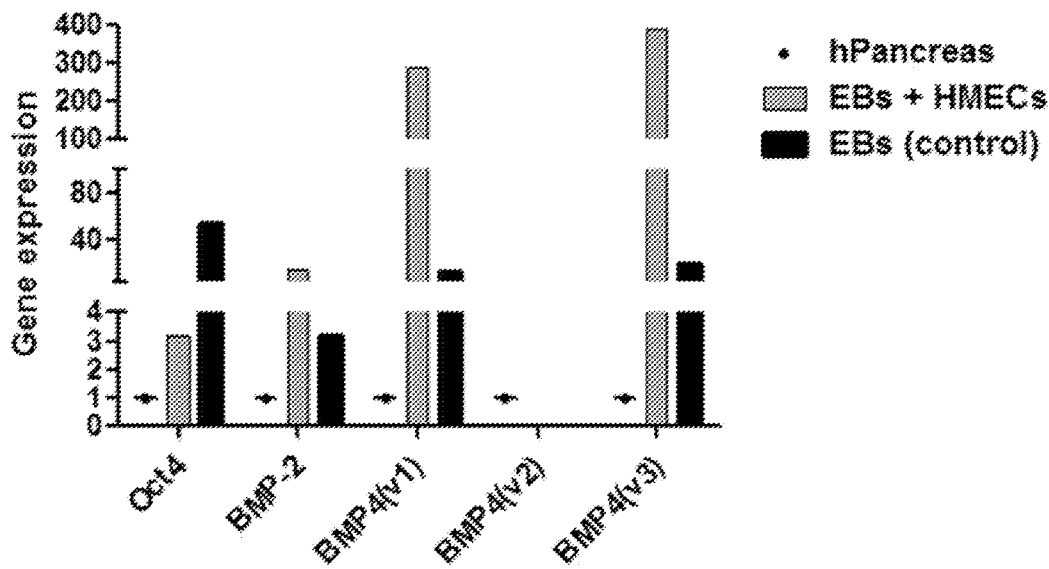

EBs not co-cultured with endothelial cells had expression of proinsulin with no co-expression of pSMAD 1, 5, 8 (FIG. 21a,b). In contrast, EBs co-cultured with ECs show expression of this phosphorylated protein localized in the nuclei of cells where islet-like clusters are forming (FIG. 21c, d).

Upregulation of BMP-2/-4 was corroborated by qRT-PCR. Higher expression of BMP-2 and BMP-4 was found in those EBs co-cultured with endothelial cells for 20 days in comparison to those EBs cultured alone (FIG. 21e). In addition, co-cultured EBs expressed lower amount of the undifferentiated marker Oct4 compared to controls (FIG. 21e). Taken together these data indicate that BMP pathway activation during early stages of EBs induced by ECs is essential for islet neogenesis and beta cell differentiation in vitro. Additionally, expression of undifferentiated markers such as OCT4 tend to decrease in co-cultured cells.

Example 27

Perifusion Assay

Perifusion of Beta-TC-6 (positive control) and beta cells derived from hiPSCs was be performed as described, with some modification. Briefly, hiPSCs derived embryo bodies cultured alone or together with ECs were disassociated with accutase (Innovative Cell Technologies, Inc. San Diego). Pre-coated 15-mm glass coverslips with 0.1% gelatin (Sigma-Aldrich, St. Louis, Mo.) were loaded with dispersed beta cells. Cells were allowed for 5 min to attach to coverslips before media was completed in a 3-cm petri dish (final density: about 500 cells/cm2), and then were cultured at 37° C. with 5% CO2 for 24 h prior to perifusion experiments.

After this time, coverslips containing attached cells were washed with warmed KRBH containing 3 mmol/L glucose and placed in a perifusion micro-chamber RC-20H (Warner Instruments, Hamden, Conn.), and cells were perifused at 100 μL/min with KRBH containing 3 mmol/L glucose. After a 60-min equilibrium period (~60 to 0), cells were stimulated with 15 mmol/L glucose for 40 min, then perifusion solution was switched to 3 mmol/L glucose. One-minute samples were collected from minute −5 to 10. Thereafter, two-minute samples were collected from minute 12 to 40. Finally 5-minute sampling was collected from minute 45 to 65. Beta-cell function was expressed as pmol/L and as percentage increase of insulin release relative to baseline.

Example 28

Figure 22:
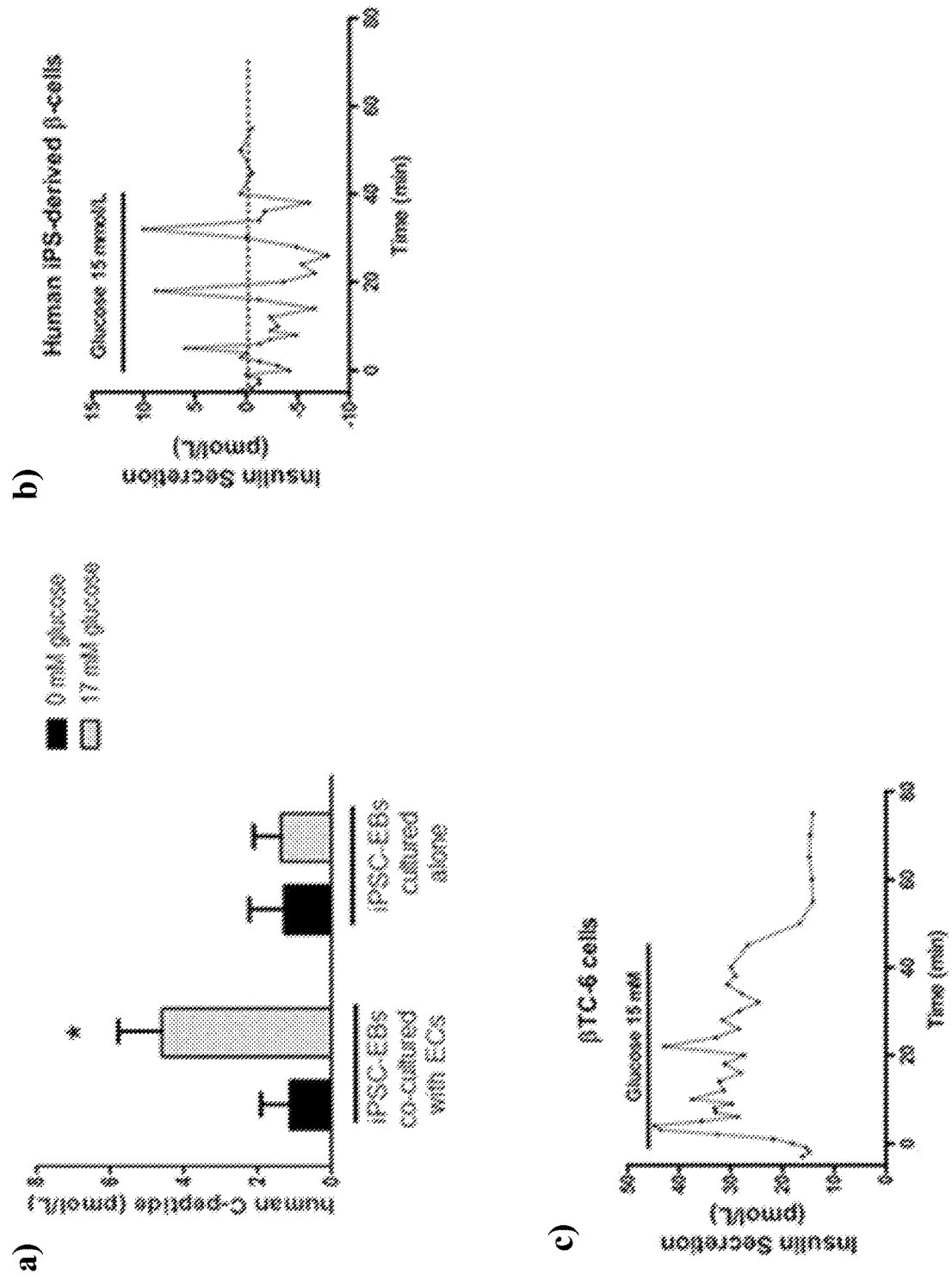
FIG. 22. Perifusiion assay for in vitro measurement of human C-peptide or insulin release from beta cells derived from EBs cultured alone or with ECs. (a) Quantification of human C-peptide in the culture medium of cells after a glucose challenge. (b) Kinetics of insulin secretion in hiPSC-derived beta cells (Note the oscillatory response to high glucose concentrations with progressive increase in the magnitude of pulsatile insulin release). (c) Kinetics of insulin secretion in Beta-TC-6 cells used as controls. (*) $P<0.05$.

Pancreatic Beta Cells Derived from EC Co-Cultures Respond More Efficiently to Glucose Challenges In Vitro To test the secretory capacity of iPSC-derived beta cells and the release of C-peptide or insulin in vitro, the cells were treated with quinacrine and a perifusion assay was performed. Quantification of human C-peptide or insulin was carried out by ELISA. Quinacrine accumulates in cell insulin granules after 30 min. At this point, maximum fluorescence was detected. In contrast, no fluorescence was detected in cells derived from EBs cultured alone. The fluorescence decreased as the glucose concentrations increased in the media. This fluorescence was quantified using the image tools of ImageJ. Significant decrease in fluorescence was observed between 1 mM and 16.5 mM of glucose. Analysis by ELISA shows a threefold increase in human C-peptide after a glucose challenge in the media from beta cells derived from EBs co-culture with ECs (FIG. 22a). In contrast, no C-peptide detection was observed in those cells derived from EBs cultured alone (FIG. 22a). The kinetics of insulin secretion was quantified using perifusion assay. Beta cells derived from hIPSCs responded to glucose with increasing amplitude in oscillations that occurred with a frequency of one oscillation every 12-14 minutes (FIG. 22b). In Beta-TC-6 used as controls, we also observed oscillations and one acute response followed by a slower response (FIG. 22c). These data indicate that sorted cells are able to secrete human C-peptide and insulin in vitro in response to glucose.

Example 29

Pancreatic Beta Cells Derived from EC Co-Cultures Respond to Glucose Levels and Efficiently Reverse Hyperglycemia in Animal Models of Diabetes Sorted cells that exhibited the capacity to respond to glucose in vitro were demonstrated as capable of expansion up to seven passages (P7). After P3, the mCherry fluorescence tended to decrease. Three to five million cells were transplanted at P3 under the kidney capsule of SCID mice.

Ninety days after transplantation, a glucose tolerance test was performed and blood samples were obtained.

Figure 23:
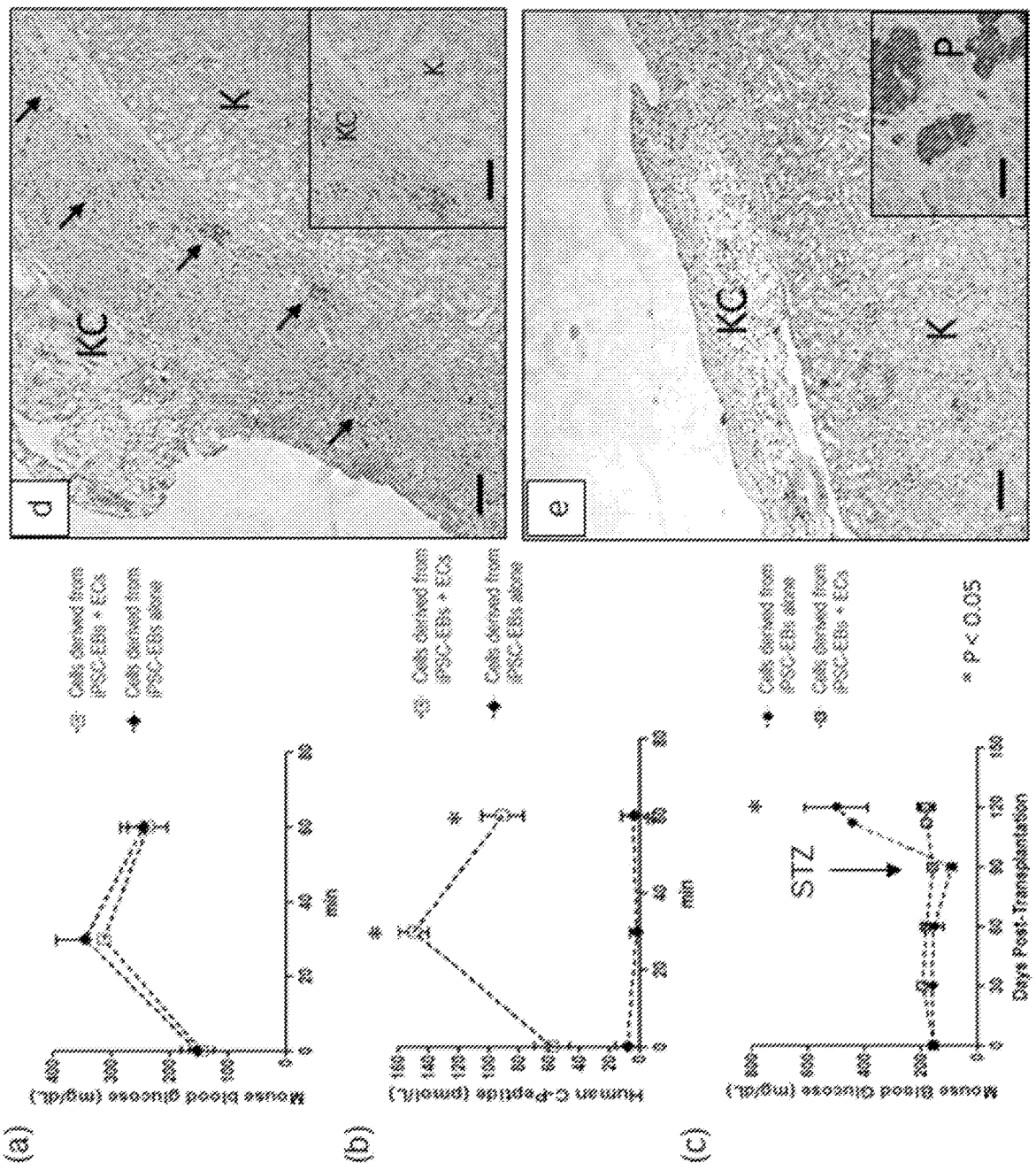
FIG. 23. Glucose tolerance test (GTT) and immunohistochemistry in mice grafted with beta cells derived from EBs cultured alone or co-cultured with endothelial cells. (a) Mouse blood glucose in mouse transplanted with cells from EBs cultured alone (black dots) or cells derived from EBs co-cultured with endothelial cells (white dots). (b) Human C-peptide levels detected in mouse blood samples in the same groups of mice describe above. (c) Mouse glucose levels before and after streptozzotocin (STZ) treatment in the groups of mice grafted with the cells described above. (d) Kidney (K) and kidney capsule (KC) of a mouse grafted with beta cells derived from EBs co-cultured with endothelial cells that express insulin (black arrows signals insulin positive cell clusters in brown). The inset shows the cells at higher magnification. (e) Kidney and kidney capsule of control mice grafted with EBs cultured alone. Normal pancreas (P) show in inset. (*) $P<0.05$. Bar=100 μm. Inset bar in 'd'=50 μm. Inset bar in 'e'=25 μm.

After a glucose challenge, control mice had a glucose increase from about 140 to 300 mg/dL with very low detection of human C-peptide (FIG. 23a, b). Concurrently, grafted mice had almost the same glucose level variation with evident increase of human C-peptide levels from 60 pmol/L to 150 and 90 pmol/L at 0, 30 and 60 minutes respectively (FIG. 23a, b).

At this time, the mice were treated with streptozotocin (STZ) and glucose levels were measured ten days after STZ treatment (FIG. 23c). The blood glucose levels were significantly higher in mice grafted with cells derived from EBs cultured alone in comparison to those mice that received differentiated cells from co-cultures. At 18 weeks post-transplantation, the kidneys were removed for IHC analysis. Abundant cells that expressed insulin were detected within a thicker kidney capsule of grafted mice (FIG. 23d) whereas no evidence of insulin expression was found in control mouse grafted with cells derived from no co-cultured EBs (FIG. 23e). These data indicates that the insulin-producing cells derived from EBs co-cultured with ECs maintain their functional phenotype in vivo.

Example 30

Derivation of Mature Beta Cells from hiPSCs Plated in a Complex Microenvironment with Endothelial Cells and Vascular Basement Membrane Components Effective interaction between hiPSC-derived EBs and ECs in presence of vascular basement components (collagen-V and laminin-I) and pancreatic differentiation factors optimize the conditions for cell survival and differentiation of hiPSC to mature insulin-producing beta cells. The in vitro interaction between EBs or definitive endoderm (DE, also derived from hiPSCs) and ECs, in particular of microvascular origin or derived from hiPSCs, is a new and unique in vitro approach to increase survival and enhance differentiation and maturation of pancreatic beta cells.

Dermal microvascular endothelium from human dermis has been chosen among other endothelial cells based on our observation that these cells promote differentiation of pluripotent cells toward pancreatic lineage and that they express bone morphogenetic proteins (BMPs). In this proposal, endothelial cells from hiPSCs will be also tested. In addition, these culture conditions will allow for cell expansion of insulin-producing beta cells in vitro.

Example 31

Summary of Approach for Analyzing iPSCs can be generated via published methods for iPSC generation from human fibroblasts. Pluripotent markers (Oct-4, SSEA-3, SSEA-4, TRA 1-60, TRA 1-81) of cells to verify iPSC stemness are measured. Generation and maintenance of EBs will be done with aggreWell protocols (STEMCELL Technologies, Vancouver, Calif.). EBs can be cultured in suspension for 7 days. After this time, these EBs will be plated alone (controls) or together with ECs in collagen-IV-laminin-I gels (Trevigen Inc. Gaithersburg, Md.).

For endothelial cells, human microvascular EC line (HMECs) can be obtained from sources such as ATCC (Manassas, Va., EUA). Human endothelial cells derived from iPSC can be derived as follows. EBs from iPSC will be treated with leptin (angiogenic hormone) and ECs will be isolated by magnetic sorting (Miltenyi Biotec, Inc.) after ten days in culture. A chief motivation for testing multiple EC cell types, such as both dermal ECs and iPSC-derived ECs is based on existing reports that demonstrate possible differential endothelial-derived factor expression between several EC lines. Establishing reproducibility of the described techniques across multiple EC cell lines establishes the described features as a robust feature not constrained to a particular co-culture cell type.

EBs are co-cultured with ECs and treated with growth factors (activin A, Wnt3a, RA, KGF [FGF-7], EGF, SB431542, EX4, Nico, HGF, and IFG1) for twenty days according to the earlier described protocols. After twenty days in three-dimensional cultures, iPSC-derived beta cells will be analyzed by ICC (after cell harvesting and re-plating), and qRT-PCR looking for undifferentiated markers (Oct-4, SSEA-3, SSEA-4, TRA-1-60, TRA-1-81), beta-cell markers (insulin, C-peptide, PDX-1, amylin, Nkx6.1, Nkx2.2, MafA, GLUT-2, Kir6.2, SUR1, GKS, PC2, PC3/PC1), pancreatic-progenitor markers (Ngn3, FoxA2, Hnf4a, Gata6, Hlxb9, Pax4, Pax6, Isl1, NeuroD, MafB), and islet-cell markers (GCG, SST, PPY, GHRL). Genetic microarrays of beta cells will be essential for the comparison with human beta cells from islets of Langerhans.

Example 32

Electrophysiological Characterization of Beta-Cell

To explore the electrophysiological properties of iPSC-derived beta cells, expression of connexins (such as Cx36) will be evaluated by ICC and WB. Furthermore, intercellular coupling will be evaluated by Lucifer yellow (LY) microinyection through a patch pipette (4% in 100 mM LiCl, Ph 7.16) into one cell of the clump of 5-8 cells and dye transfer evaluated after 5 min. After this time, the number of positive LY-stained cells will be evaluated by conventional fluorescent microcopy. In addition, intracellular calcium as well as calcium and potassium currents will be evaluated using patch clamp in whole-cell modality. Briefly, cells can be cultured in chamber and observed with an inverted microscope equipped with Hoffman optics. Recording will be made through a Dagan amplifier (Minneapolis, Minn.) using micropipettes pulled from borosilicate glass prepared in a micropipette puller. Micropipettes will have a resistance of at least 5 GΩ. Sealing and recording will be monitored with a Tektronix 2212 oscilloscope. Whole-cell currents will be recorded through Ag—AgCl electrodes and filtered at 1 kHz. Signals will be digitalized and stimulation and analysis will be made by a Clampex/Clampan program.

Example 33

Isolation and Expansion of Mature Beta Cells Derived from hiPSCs and Study of the Kinetics of Insulin Secretion Labeling hiPSC-derived beta cells with a reporter gene is a useful approach for cell isolation, expansion, and further characterization. Derived cells will be infected with lentivirus that carries mCherry (red fluorescent protein) under the control of insulin promoter and GFP (green fluorescent protein) under the control of ubiquitin C promoter. The cells will be sorted by FACS after some passages and expanded in vitro for the first time. Complete characterization of these cells will be done by ICC, genetic microarrays, and karyotyping. Kinetics of insulin secretion will be evaluated in vitro by perifusion assay.

Example 34

Experimental Approach for Further Characterization

After twenty days of differentiation in gels, the EBs are harvested using collagenase I (Worthington, Lakewood, N.J.). These cells can plated on gelatin pre-coated dishes for expansion. The culture medium for maintenance will consist of RPMI 1640 (Cellgro 10-040-CV) with supplements (NEAA, sodium pyruvate, beta-mercaptoethanol, glutamine, PS, HEPES, and FBS [Omega Sci., FB-02]). This media contains low glucose and it has been used for the growth of rat islets of Langerhans. After about 2-3 passages, the cells will be replated at $5 \times 10^4$ cells/mL in a 48-well plate.

With the cells at 60% confluence, transduction with the Rat INS-mCherry lenti viral vector will be performed. Four hours post transduction, the cells will be washed with basal media and fresh maintenance media will be added. The transduction efficiency will be monitored by the number of cells expressing hrGFP-NLS reporter. After 24 hours, the cells will be monitored under fluorescent microscope. mCherry positive cells will be sorted by FACS after few passages. Further expansion of the cells will be done to obtain a suitable cell number for transplantation (usually 3 to 5 more passages). Genetic microarrays will be performed in our Cedars-Sinai genomic core. In collaboration with Dr. Kandeel at Beckman Research Institute at City of Hope, we will compare marker expression between our hiPSC-derived beta cells and beta cells from human islets also subjected to ICC, WB, and genetic microarrays.

Perifusion of beta cells derived from hiPSCs will be performed as previously described with some modifications. Briefly, derived beta cells will be harvested and transfer to gelatin pre-coated 15-mm glass coverslips. The cells will be fed with RPMI 1640 (Cellgro 10-040-CV) with supplements (NEAA, sodium pyruvate, beta-mercaptoethanol, glutamine, PS, HEPES, and FBS [Omega Sci., FB-02]). After 24 hours at 37° C. with 5% CO2, coverslips containing attached cells will be washed with warmed KRBH containing 3 mmol/L glucose and placed in a perifusion micro-chamber RC-20H (Warner Instruments, Hamden, Conn.). Beta cells will be perifused at 100 µL/min with KRBH containing 3 mmol/L glucose. After a 60-min equilibrium period (−60 to 0), cells will be stimulated with 15 mmol/L glucose for 40 min, then perifusion solution will be switched to 3 mmol/L glucose. One-minute samples will be collected from minute −5 to 10. Thereafter, two-minute samples will be collected from minute 12 to 40. Finally 5-minute sampling will be collected from minute 45 to 65. Insulin secretion will be expressed will be expressed as pmol/L and as percentage increase of insulin release relative to baseline.

A potential obstacle in the described is the persistent presence of ECs even after sorting. One adjustment could include inactivation of ECs using mitomycin C for the sake of impairing cellular mitosis and removing the presence of these cells. In addition, the application of EC-conditioned medium allows reduced risk EC contamination for generation of pure populations of beta cells for analysis and transplantation. Another strategy is the use of inserts to avoid cell-cell contact between ECs and beta cells. Finally, a potential problem regarding beta-cell transferring is the presence of cytogenetic abnormalities of the iPSC-derived beta cells after several passages. In this regard, one can monitor the cells by karyotyping and, if necessary, spectral karyotyping (SK) and the related multiplex fluorescence in situ hybridization (M-FISH).

Example 35

Expansion of iPSC-Derived Beta Cells

The hiPSC-derived beta cells (mCherry positive) can be plated in culture dishes pre-coated with gelatin. After ten days in culture, may form monolayers (FIG. 25a). The number of mCherry positive cells will increase as function of time (FIG. 25b-d). At passage 3, some beta cells tended to form islet-like clusters (FIG. 25e,f). These cells can be transferred at time points up to passage 3-5 in collagen-laminin gels before transplantation. No further sorting was performed. In flasks pre-coated with collagen-laminin, beta cells formed clusters (FIG. 26a, e, i) that expressed proinsulin (FIG. 26c, g, k), human nuclear antigen Example 36

Study of Bone Morphogenetic Pathway Activation Induced by Endothelial Cells in Beta-Cell Maturation In Vitro Endothelial cells stimulate upregulation of bone morphogenetic proteins (BMPs) and their receptor (BMPR1A) in cultured embryoid bodies. This increase induce phosphorylation of proteins such SMADs (phosphoSMADs or pSMADs) as part of bone morphogenetic pathway activation. This pathway activation may be crucial for beta cell survival, differentiation, and maturation. The role of pSMADs in bet-cell maturation in vitro has not been completely characterized.

It has been reported that bone morphogenetic protein-4 (BMP-4) as well as BMPR1A are essential for adequate beta-cell response to glucose but the genes and pathways activated by BMP-4 are unknown. Recently, the Inventors reported the crucial role of combinatorial effects of BMP-2 and BMP-4 in the enhancement of insulin-producing cells and pancreatic and duodenal homeobox 1 (PDX-1) expressing cells. PDX-1 is an essential transcription factor for beta cell differentiation and maturation. Therefore, of interest is characterizing expression of novel elements associated with BMP pathway activation induced by ECs linked to beta cell maturation. Towards this end, recombinant BMPs can be deployed to mimic EC effects and BMP antagonists or shRNAs to inhibit such effects. Genetic microarrays will be crucial to identify novel genes and pathways activated by BMPs that are upregulated by ECs.

Example 37

Genetic Profile of iPSC-Derived Beta Cells

Figure 20:
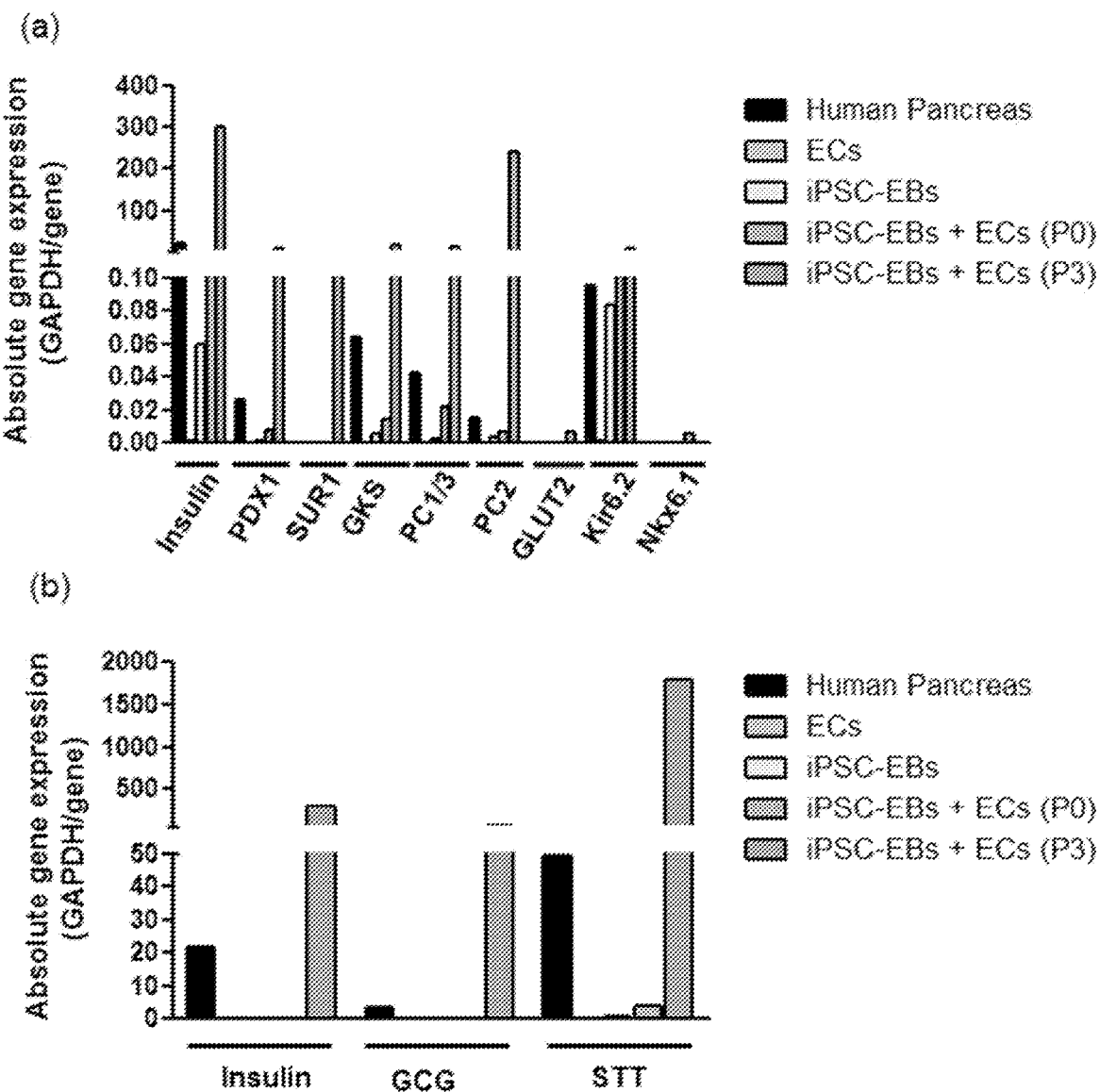
FIG. 20. Gene expression profile of iPSC-derived EB cultured alone or with ECs cells before and after cell sorting. (a) Beta-cell markers in human pancreas, endothelial cells, iPSC-derived EBs cultured alone or with endothelial cells at P0 and P3. (b) Islet markers in the same groups of cells mentioned above.

Beta-cell marker expression was evaluated EBs cultured alone or together with ECs before and after sorting. Higher expression of mature beta cell markers and islet markers was found in sorted cells at passage 0 and 3 in cells derived from EBs co-cultured with ECs in contrast with controls (FIG. 20a). In addition, higher expression of islet markers was also found in these cells after sorting (FIG. 20b).

Example 38

Study of Bone Morphogenetic Pathway Activation

SMAD Activation

Embryoid bodies derived from hiPSCs cam be cultured alone or with ECs. These EBs will be cultured in collagen IV,I-laminin I gels and treated with the following differentiation factors and steps:
- (Step 1) Activin A and Wnt3a
- (Step 2) Retinoic Acid (RA) and Fibroblast Growth Factor-7 (FGF-7)
- (Step 3) Epidermal growth factor (EGF) and SB431542
- (Step 4) Hepatocyte growth factor (HGF), insulin-like growth factor 1 (IGF-1), exendin-4 (EX4), and Nicotinamide (Nic)

After each step of the differentiation process, some cells will be fixed to be analyzed by ICC and some will be harvested to be analyzed by WB, qRT-PCR, and genetic microarrays. For ICC, fixed cells can be stained for BMP-2, BMP-4, BMPR1a, and phosphoSAMD1,5,8. Through these experiments, we will identify expression of BMP pathway elements that will be corroborated by WB. Expanded protocols details are presented in Tables 3 and 4.

TABLE 3

Concentrations and Components Used in Differentiation Protocol

| Step 1 (optional combo a) | Reagents | Final conc. | Units |
|---|---|---|---|
| D1 | RPMI** | | |
| | Activin A | 100 | ng/ml |
| | Wnt3a | 25 | ng/ml |

| Step 1 (optional combo b) | Reagents | Final conc. | Units |
|---|---|---|---|
| | RPMI** | | |
| D2 | Activin A | 100 | ng/ml |
| D3 | FBS | 0.2 | % |

| Step 2 | Reagents | Final conc. | Units |
|---|---|---|---|
| D4 | | | |
| D5 | | | |
| D6 | DMEM/F12** | | |
| D7 | RA* | 2 | μM |
| D8 | KGF | 50 | ng/ml |
| D9 | | | |

| Step 3 | Reagents | Final conc. | Units |
|---|---|---|---|
| D10 | | | |
| D11 | DMEM-H** | | |
| D12 | EGF | 50 | ng/ml |
| D13 | SB431542 | 0.42 | μg/ml |
| D14 | | | Final Volume (μl)> |

| Step 4 | Reagents | Final conc. | Units |
|---|---|---|---|
| D15 | | | |
| D16 | DMEM-H | | |
| D17 | HGF | 50 | ng/ml |
| D18 | IGF-I | 50 | ng/ml |
| D19 | Exendin-4 | 50 | ng/ml |
| D20 | Nic | 10 | mmol/L |
| D21 | | | |

| Media | Supplem | Final conc. | Units |
|---|---|---|---|
| RPMI** | Glutamax | 2 | mmol/l |
| | beta-Merca | 100 | umol/l |
| | NEAA | 1 | mmol/l |
| DF12** | Glutamax | 2 | mmol/l |
| | beta-Merca | 100 | umol/l |
| | NEAA | 1 | mmol/l |
| DMEM-H** | Glutamax | 2 | mmol/l |
| | beta-Merca | 100 | umol/l |
| | NEAA | 1 | mmol/l |

**This medium should be added to HMECs and used as conditioned media (EC-CM) after 48 hrs.
**The EC-CM should be added together with growth factors.

TABLE 4

Schedule for Differentiation

| Procedure | Days |
|---|---|
| Prepare 6-well plates with Matrigel | 1 |
| Thaw and plate human iPSCs | 1 |
| Transfer human iPSCs | 7 |
| Form EBs | 6 |
| Plate EBs in collagen with ECs | 1 |
| Differentiation stage 1 | 1 |
| Differentiation stage 2 (1b) | 1 |
| Differentiation stage 3 | 6 |
| Differentiation stage 4 | 5 |
| Differentiation stage 5 | 7 |
| Beta-cell harvesting and transfering | 1 |
| Beta-cells passage 1 | 7 |
| Beta-cells passage 2 | 7 |
| Beta-cells passage 3 | 7 |
| Time to derive beta cells suitable for tranplantation (days) | 58 |
| Time to derive beta cells suitable for tranplantation (months) | 2 |
| Days with grafted beta cells | 120 |
| Months with grafted beta cells | 4 |
| Total (days) | 178 |
| Total (months) | 6 |

Example 39

Gene Expression Profile of Differentiated Cells

For qRT-PCR, total RNA will be extracted from EBs cultured alone or together with ECs using RNAeasy mini kit (Qiagen, Valencia, Calif.). After cDNA synthesis, using a QuantiTect Reverse Transcription kit (Qiagen, Valencia, Calif.), quantitative real-time PCR analysis will be performed using a SYBR Green RT-PCR kit (Qiagen, Valencia, Calif.) and the LightCycler instrument for measurement of related genes such as BMP-2, BMP-4, BMPR1A, BMP1B, and BMPII.

For microarrays, RNA will be assessed for quantity and quality using NanoDrop 8000 Spectrophotometer and Agilent 2100 Bioanalyzer respectively. All samples scored 10 (highest score) for RNA integrity by the Bioanalyzer software. Each sample will be prepared according to manufacturer's instructions for The Ambion® WT Expression Kit For Affymetrix® GeneChip®. Whole Transcript (WT) Expression Arrays and Affymetrix GeneChip® WT Terminal Labeling Kit to synthesize sense strand cDNA from total RNA and fragment and label samples respectively. Each sample will be hybridized to an Affymetrix® GeneChip Mouse Gene 1.0 ST Array. Arrays will be scanned using the Affymetrix® GeneChip® Scanner 3000. Raw data will be imported to Affymetrix® Expression Console software and it will be PLIER summarized, GC composition-based background corrected (PM-GCBG), and sketch-quantile normalized.

Pathways will be generated to assess potential functional relationships based on curated interactome and pathway knowledge basis using the tools of Ingenuity Pathway Analysis (IPA) bioinformatics software (v. 14197757, Redwood City, Calif.). Novel pathways or genes linked to BMP pathway activation toward beta-cell maturation will be investigated. In addition to the genetic analysis, agonists (recombinant BMPs) and antagonists (Noggin, Chordin) for BMP-2/-4 bioactivities will be used to corroborate BMPs effects and to mimic or inhibit ECs effects in beta-cell maturation. These agonists or inhibitors will be used during the whole differentiation process or in each step of differentiation to analyze the point in which the role of BMPs is crucial for beta-cell differentiation and maturation.

As a potential problem in the described approach is the contamination of RNA from ECs in co-cultures, one of ordinary skill can perform the above experiments endothelial-cell conditioned medium to minimize the presence of contaminating EC RNA. Alternatively, endothelial cells can be inactivated with Mitomycin C, followed by transfer of beta cells for some passages before extracting the RNA, thereby reducing the level of potential contaminating EC RNA. A final adjustment could be provided by co-culture without cell-cell contact using ECs plated on Millipore inserts.

Example 40

Figure 27:
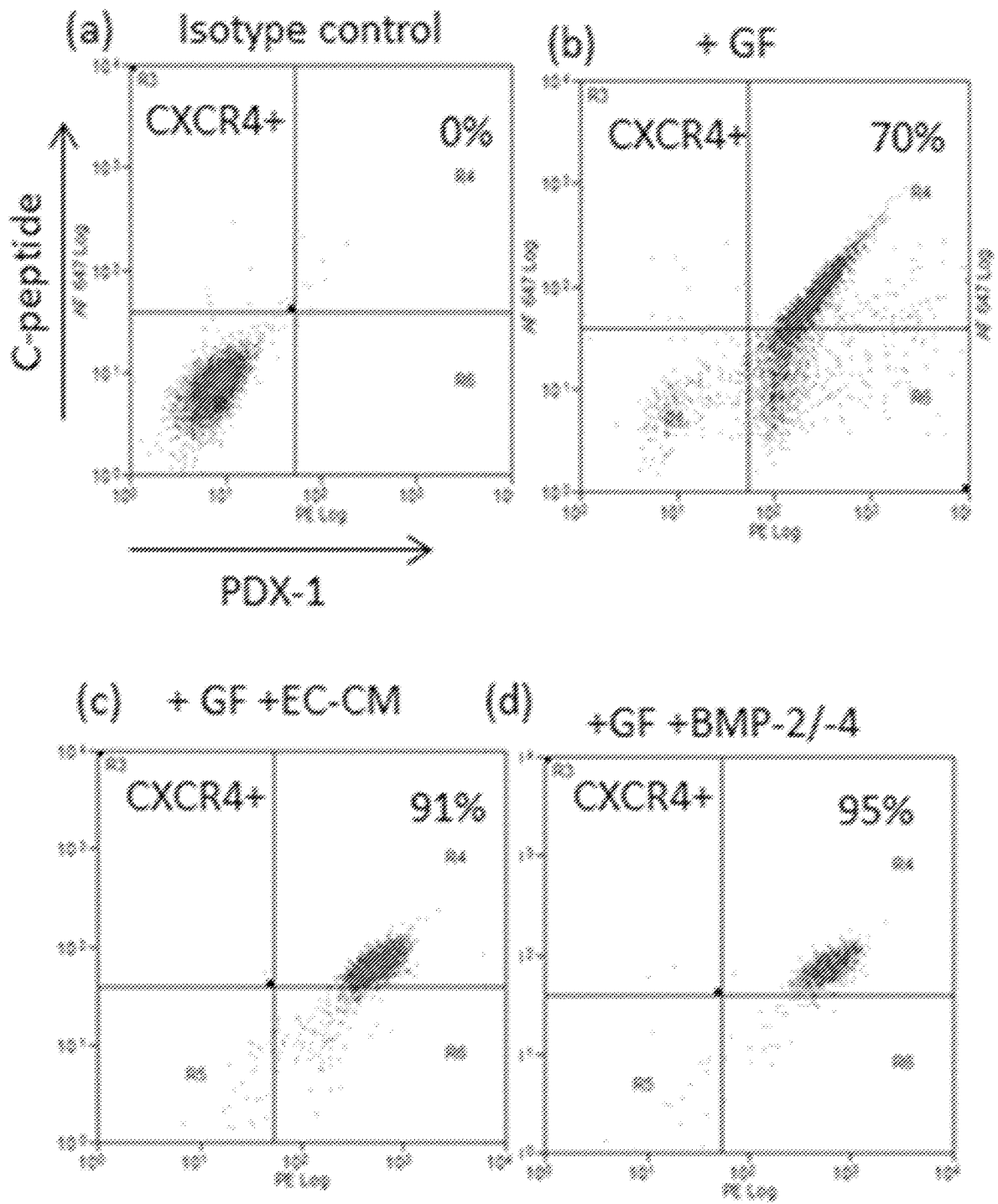

Role of Bone Morphogenetic Pathway Activation Induced by Endothelial Cells in Beta-Cell Maturation In Vitro To test the combinatorial effects of BMP-2/-4, one can add these factors to definitive endoderm (DE) cells that express CXCR4. Preliminary results by the inventors indicated that negative and isotype controls did not co-express these markers (FIG. 27a). DE cells treated with pancreatic differentiation factors (GF) co-expressed up to 70% of proinsulin and PDX-1.

However, higher expression was found in cells treated also with EC-conditioned medium (FIG. 27c). Importantly, these effects could be mimicked by a combination of GF and BMP-2 and -4 during the whole differentiation process (FIG. 27d). As described, after 20 days of differentiation, EBs cultured alone did express some insulin but did not co-express phospoSMAD1,5,8 (FIG. 21a,b). In contrast, more islet-like clusters found within EBs co-cultured with were composed of beta cells that co-expressed phosphoSMAD1, 5,8 (FIG. 21c, d). Quantification of BMP-2/-4 indicated higher expression of BMP-2 and BMP-4 in co-cultured EBs compared to controls (FIG. 21e).

Example 41

In Vivo Functional Evaluation of Beta Cells Derived from hiPSCs

After sorting, functional secretory capacity of beta cells derived from hiPSCs will be evaluated in vivo after implantation into the kidney capsule of severe combined immunodeficient (SCID) mice. Blood samples will be collected before and after transplantation to measure human C-peptide levels. At different time points after transplantation, glucose tolerance tests will be performed. About one hundred days after transplantation, mice beta cells will be destroyed by streptozotocin (STZ) and the capacity of human beta cells to maintain normal blood glucose levels will be evaluated. Adjustment in the amount of beta cells necessary to maintain normal glucose levels will be done. Grafted kidneys will be harvested and analyzed by immunohistochemistry and tumor formation will be also evaluated.

A confluent monolayer of beta cells can be expanded up to five passages, harvested, treated with accutase and centrifuged to a pellet of $3\times10^6$ cells. Forty male mice of 6-8 weeks old (25-35 grams) with severe combined immunodeficiency (Prkdc) will be necessary to evaluate statistically significant differences in the response of the cells transplanted. Mice will be subjected to anesthesia with isoflurane in a vaporizer machine. An incision will be made in the left flank. Three million hiPSC-derived beta cells obtained from EBs co-cultured with ECs will be transplanted under the kidney capsule using an insulin syringe with an ultra-fine needle. The kidney subcapsule is considered the standard site for murine islet transplantation studies.

Control animals will have cells derived from EBs cultured alone injected under the kidney capsule. Blood samples will be collected before transplantation and 30, 60, 105, 112, and 120 days after transplantation and analyzed for human insulin and C-peptide using an ultrasensitive ELISA assay (detection limit 0.42 pmol/L). STZ is injected to destroy native murine beta cells at day 105 after cell transplantation. Human beta cells are not sensitive at these concentrations. Blood collection will be performed by submandibular method. Glucose tolerance tests will be performed at 120 days after transplantation. Mice will be euthanized after anesthesia at 126 days after transplantation by exsanguination and the left kidney harboring the transplanted cells will be removed for immunohistochemical (IHC) study of pancreatic endocrine cells (alpha, beta, delta and PP) and their associated hormones by qRT-PCR and Western Blot. For IHC, paraffin sections will be obtained from grafted and control kidneys and commercially available primary antibodies will be used in microwave heat-induced epitope retrieval, and the automated detection systems such as Leica BOND-MAX (Leica Microsystems Inc, Buffalo Grove, Ill.) or DAKO autostainer (Dako North America Inc., Carpinteria, Calif.).

Example 42

Transplantation of Beta Cells Derived from hiPSC Cells and Cell Function Evaluation In Vivo To evaluate function of hiPSC-derived insulin-producing cells in vivo, the Inventors transplanted these cells under the kidney capsule of SCID mice. $3\times10^6$ cells were transplanted and blood glucose samples were collected at different time points. The following preliminary results were generated in in five control and five transplanted mice. The glucose tolerance test (GTT) indicates blood glucose increase at 30 min post glucose challenge and decrease at 60 min (FIG. 23a).

The Inventors found correlation with human C-peptide secretion increase (FIG. 23b). Mice treated with STZ were hyperglycemic about two weeks after treatment while mice grafted with beta cells derived from co-cultures were normoglycemic (FIG. 23c). Grafted beta cells from co-cultures expressed insulin at 60 to 100 days post-transplantation (FIG. 23d). Controls transplanted with EBs cultured alone were negative for insulin (FIG. 23e). Taken together, these data suggest that endothelial cell signals are essential for pancreatic beta cells maturation in vitro. At present, we continue to follow these mice with transplanted hiPSC-derived beta cells and wait for longer periods to perform glucose-tolerance tests.

In order to evaluate the functionality of pancreatic beta-cells derived from induced pluripotent stem cells (iPSCs) we have optimized two bioassays.

Example 43

Quail Chorioallantoic Membranes (CAMS) as Bioassay

The CAM model offers many advantages over other models, including easy access to the blood vessel network, function in low or absence of immunocompetence, shorter time frame for study completion, and no concern because of animal sacrifices. Additionally, this assay is relatively simple and inexpensive, and is suitable for large scale screening.

Quail eggs are incubated for three days, after this period the eggs are open (embryos at 3 days of age) and the each embryo is placed in one well of a six-well plate and incubated without humidity and CO2 in an incubator at 37° C. After four more days (embryos at 7 days of age) the chorioallantoic membranes developed by the embryos are suitable to receive any implant such as cells within a scaffold.

Example 44

Preparation of iPSCs-Derived Beta Cells for Implantation into the CAM

About $1\times10^6$ iPSC-derived beta cells obtained with our method will be plated together with different amounts of endothelial cells (ECs) derived either from iPSCs (iECs) or endothelial cell (EC) lines from human dermis (human dermal microvascular endothelial cells) before implantation (Table 1). These cells will be plated together in 1 mL collagen-I, collagen-IV, and laminin-I or Matrigel scaffolds. Then drops of 100 µL (total 10 drops) will be placed on Petri dishes for solidification. The cells will be maintained for 24 hours with the media for iPSC-derived beta cell consisted in CMRL 1066, supplemented CIT modification (Mediatech, Inc., University of Miami, Cat#98-304-CV). After this time, the scaffolds will be implanted into the CAMs as follows:

+iPSC-derived Beta Cells+iECs in
gels-----→CAMs-----→Insulin secretion

At 6-7 days after implantation, blood samples as well as quail embryos will be harvested and the grafts will be fixed with paraformaldehyde to be analyzed by histology. The blood samples will be analyzed by ultrasensitive ELISA to quantified human hormones such as human proinsulin (C-peptide), glucagon, or somatostatin.

The percentage of iPSC-derived beta cells and ECs will be analyzed to optimize the function of iPSC-derived beta cells according to the following Table 5:

TABLE 5

Proportion of iPSC-derived beta cells and induced ECs implanted on CAMs.
Proportion of Implanted Cells into the CAM

| 0% iBeta Cells | 25% iBeta Cells | 50% iBeta Cells | 75% iBeta Cells | 100% iBeta Cells |
|---|---|---|---|---|
| 100% iECs | 75% iECs | 50% iECs | 25% iECs | 0% iECs |
| 20 CAMs | 20 CAMs | 20 CAMs | 20 CAMs | 20 CAMs |

Figure 28:
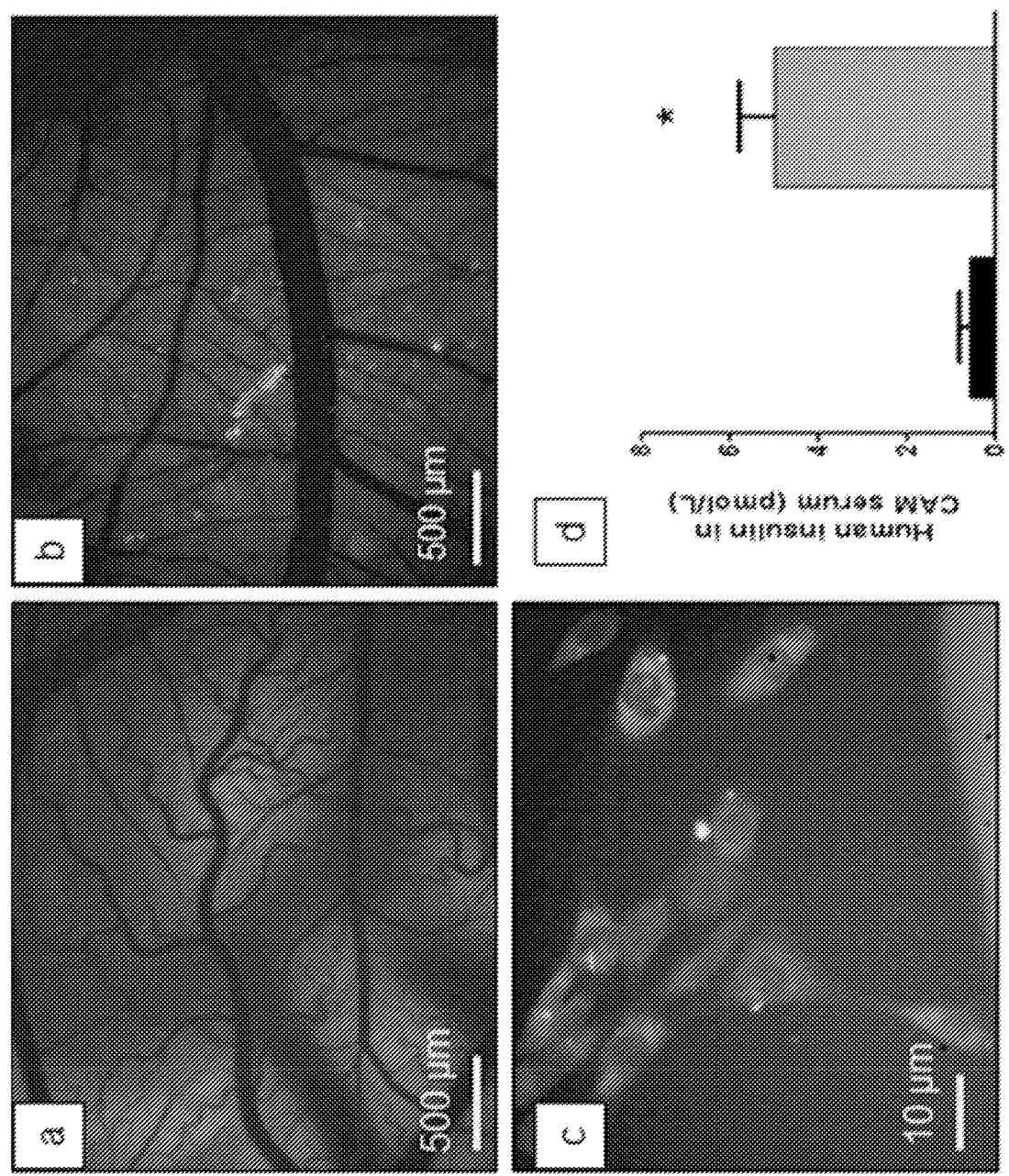
FIG. 28. Insulin producing cells implanted on CAMs. (a) CAM control without cells. (b) CAM with insulin-producing cells (green fluorescent positive). (c) Higher magnification of the cells in 'b'. (d) Detection of human insulin in quail blood samples. * $P<0.05$.

Preliminary results from this approach indicate that Insulin-producing cells derived from mouse fibroblasts were implanted on CAMs as controls to evaluate insulin secretion. Preliminary results indicated cells, when transfected with a plasmid that expressed green fluorescent protein (GFP) driven by rat insulin promoter, were capable of expressing the reporter protein (FIG. 28).

Example 45

Beta Cells Transplantation in Severe Combined Immunodeficient (SCID) Mice

Preparation of iPSCs-derived beta cells for implantation into the kidney capsule of SCID mice included use of about $1\times10^6$ iPSC-derived beta cells obtained with via the described method, plated together with different amounts of endothelial cells (ECs) derived either from iPSCs or endothelial cell (EC) lines from human dermis (human dermal microvascular endothelial cells) before implantation (Table 6). These cells will be plated together in 1 mL collagen-I, collagen-IV, and laminin-I or Matrigel scaffolds. Then drops of 100 µL (total 10 drops) will be placed on Petri dishes for solidification. The cells will be maintained for 24 hours with the media for iPSC-derived beta cell consisted in CMRL 1066, supplemented CIT modification (Mediatech, Inc., University of Miami, Cat#98-304-CV). After this time, the scaffolds will be implanted into the CAMs.

Figure 29:
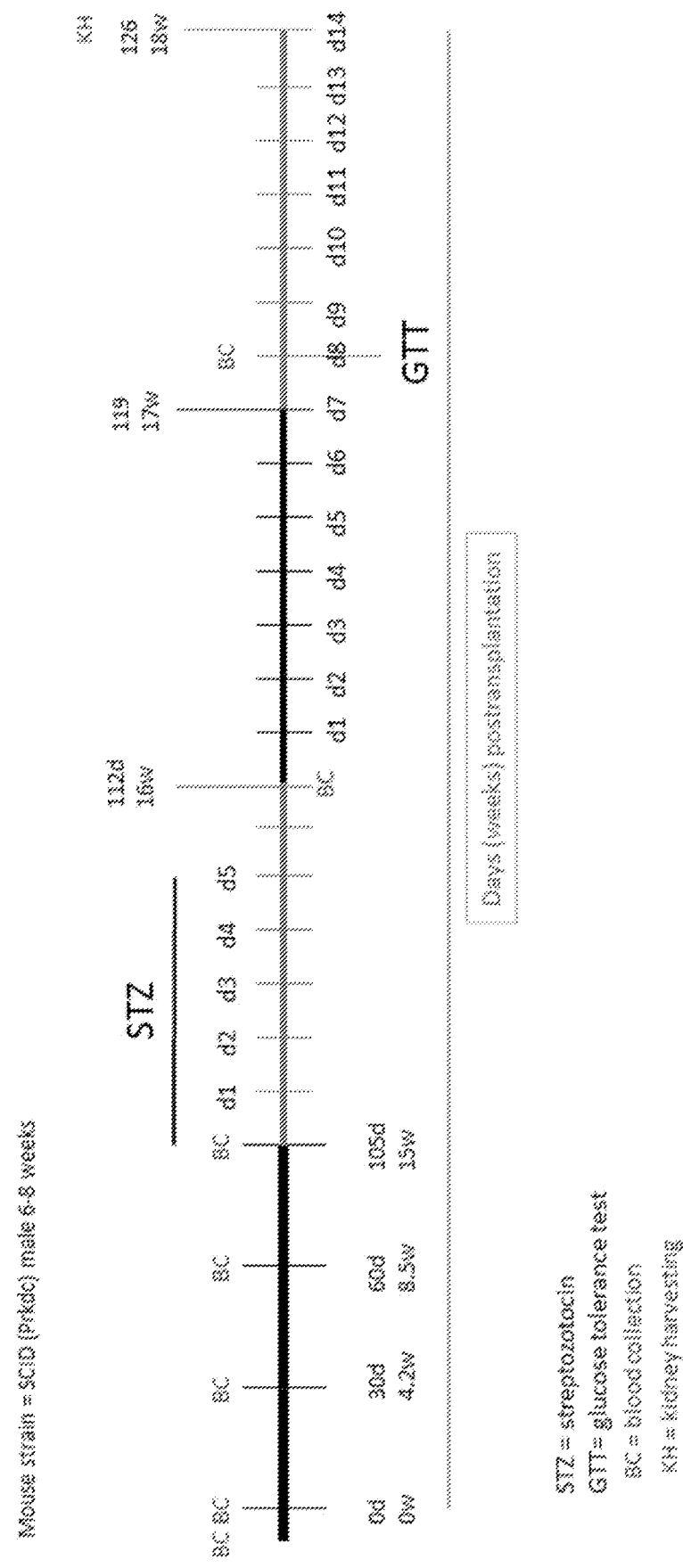
FIG. 29. Chronology of the procedures performed in SCID mice after cell tranplantation.

Cells within collagen I, IV, and laminin I scaffolds will be transplanted into the kidney capsule or dermis of SCID mice. After 120 days, the mice will be treated with streptozotocin (STZ) to destroy native beta cells and after two weeks a glucose tolerance test will be performed in these mice. The kidneys will be removed for immunohistochemical analysis. Blood samples will be collected at different time points after transplantation according to the graphic protocol (FIG. 29).

The percentage of iPSC-derived beta cells and ECs will be analyzed to optimize the function of iPSC-derived beta cells according to the following Table 6:

TABLE 6

Proportion of iPSC-derived beta cells (iBeta Cells) and iECs transplanted into the kidney capsule or dermis of SCID mice.
Proportion of Cells Transplanted into the Kidney Capsule or dermis of SICD mMice

| 0% iBeta-Cells | 25% iBeta-Cells | 50% iBeta-Cells | 75% iBeta-Cells | 100% iBeta Cells |
|---|---|---|---|---|
| 100% iECs | 75% iECs | 50% iECs | 25% iECs | 0% iECs |
| 10 mice | 10 mice | 10 mice | 10 mice | 10 mice |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods of deriving insulin-producing cells from pluripotent stem cells, preparing, isolating, or modifying cells used in the described differentiation techniques, derivation of insulin-producing cell lines from the aforementioned techniques, treatment of diseases and/or conditions that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

Nakagawa, M., and Yamanaka, S. (2010). CHAPTER 14 REPROGRAMMING OF SOMATIC CELLS TO PLURIPOTENCY. Gene 215-224.

Pan, X., Xue, W., Li, Y., Feng, X., Tian, X., and Ding, C. (2011). Islet graft survival and function: concomitant culture and transplantation with vascular endothelial cells in diabetic rats. Transplantation 92, 1208-1214.

Takahashi, K., and Yamanaka, S. (2006). Induction of pluripotent stem cells from mouse embryonic and adult fibroblast cultures by defined factors. Cell 126, 663-676.

Talavera-Adame, D., Dafoe, D. C., Ng, T. T., Wachsmann-Hogiu, S., Castillo-Henkel, C., and Farkas, D. L. (2009). Enhancement of embryonic stem cell differentiation promoted by avian chorioallantoic membranes. Tissue Engineering. Part A 15, 3193-3200.

Talavera-Adame, D., Ng, T. T., Gupta, A., Kurtovic, S., Wu, G. D., and Dafoe, D. C. (2011a). Characterization of microvascular endothelial cells isolated from the dermis of adult mouse tails. Microvascular Research 82, 97-104.

Talavera-Adame, D., Wu, G., He, Y., Ng, T. T., Gupta, A., Kurtovic, S., Hwang, J. Y., Farkas, D. L., and Dafoe, D. C. (2011b). Endothelial Cells in Co-culture Enhance Embryonic Stem Cell Differentiation to Pancreatic Progenitors and Insulin-Producing Cells through BMP Signaling. Stem Cell Reviews 7, 532-543.

Zhu, F. F., Zhang, P. B., Zhang, D. H., Sui, X., Yin, M., Xiang, T. T., Shi, Y., Ding, M. X., and Deng, H. (2011). Generation of pancreatic insulin-producing cells from rhesus monkey induced pluripotent stem cells. Diabetologia 2325-2336.

The invention claimed is:

1. A method of differentiating a human induced pluripotent stem cell (iPSC) into a mature insulin producing cell comprising:
   (a) providing a quantity of human iPSCs;
   (b) culturing the human iPSCs in the presence of activin A at 100 ng/mL and wingless-related MMTV integration site 3A (WNT3A) at 25 ng/mL for 3 days to generate definitive endoderm cells that are positive for C-X-C motif chemokine receptor 4 (CXCR4) and SRY-box transcription factor 17 (SOX17);
   (c) further culturing the definitive endoderm cells with endothelial cells in a collagen I, collagen IV, and laminin I gel mixture, in the presence of all-trans retinoic acid (RA) at 2 μmol/L and keratinocyte growth factor (KGF) at 50 ng/mL for about 6 days;
   (d) additionally culturing in the presence of epidermal growth factor (EGF) at 50 ng/mL for 5 or 6 days; and
   (e) further culturing in the presence of hepatocyte growth factor (HGF) at 50 ng/mL, insulin-like growth factor (IGF1) at 50 ng/mL, exendin-4 at 50 ng/mL, and nicotinamide at 10 mmol/L for about 7 days, thereby obtaining the mature insulin producing cells that secrete insulin and/or human C-peptide in response to glucose stimulation, and wherein the mature insulin producing cells express urocortin 3, pancreatic duodenal homeobox 1 (PDX-1), and C-peptide.

2. The method of claim 1, wherein the endothelial cells are human microvascular endothelial cells (HMECs).

3. The method of claim 1, wherein the mature insulin producing cells further express one or more markers selected from the group consisting of: proinsulin, the insulin, glucagon, somatostatin, and Nkx6.1.

4. The method of claim 1, wherein the mature insulin producing cells are pancreatic beta-cells.

5. A method of differentiating a human induced pluripotent stem cell (iPSC) into a mature insulin producing cell comprising:
   (a) providing a quantity of human iPSCs;
   (b) inducing formation of embryoid bodies (EBs) derived from the human iPSCs;
   (c) culturing the EBs derived from the human iPSCs with human endothelial cells (ECs) in the presence of activin A at 100 ng/mL and wingless-related MMTV integration site 3A (WNT3A) at 25 ng/mL in a collagen I, collagen IV, and laminin I gel mixture, for at least a day and up to 3 days;
   (d) further culturing the EB-EC co-culture derived resulting cells from step (c) in the presence of all-trans retinoic acid (RA) at 2 μmol/L and keratinocyte growth factor (KGF) at 50 ng/mL for 6 days;
   (e) additionally culturing in the presence of epidermal growth factor (EGF) at 50 ng/mL for 5 or 6 days; and
   (f) further culturing in the presence of hepatocyte growth factor (HGF) at 50 ng/mL, insulin-like growth factor (IGF1) at 50 ng/mL, exendin-4 at 50 ng/mL and nicotinamide at 10 mmol/L for 7 days,
   thereby producing mature insulin producing cells; wherein the mature insulin producing cells secrete insulin and/or human C-peptide in response to glucose stimulation, and wherein the mature insulin producing cells express urocortin 3, pancreatic duodenal homeobox 1 (PDX-1), and C-peptide.

6. The method of claim 5, wherein the mature insulin producing cells further express proinsulin.

7. The method of claim 5, wherein the human ECs are human microvascular endothelial cells (HMECs).

\* \* \* \* \*

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: GAPDH Forward Primer

<400> SEQUENCE: 1
agccacatcg ctcagacacc                                           20

<210> SEQ ID NO 2
<211> LENGTH: 20
<212> TYPE: DNA
<213> ORGANISM: Artificial Sequence
<220> FEATURE:
<223> OTHER INFORMATION: GAPDH Reverse Primer

<400> SEQUENCE: 2
gtactcagcg gccagcatcg                                           20

<210> SEQ ID NO 3
<211> LENGTH: 20
<212> TYPE: DNA
<213> ORGANISM: Artificial Sequence
<220> FEATURE:
<223> OTHER INFORMATION: Insulin Forward Primer

<400> SEQUENCE: 3
agcctttgtg aaccaacacc                                           20

<210> SEQ ID NO 4
<211> LENGTH: 20
<212> TYPE: DNA
<213> ORGANISM: Artificial Sequence
<220> FEATURE:
<223> OTHER INFORMATION: Insulin Reverse Primer

<400> SEQUENCE: 4
gctggtagag ggagcagatg                                           20

<210> SEQ ID NO 5
<211> LENGTH: 25
<212> TYPE: DNA
<213> ORGANISM: Artificial Sequence
<220> FEATURE:
<223> OTHER INFORMATION: PDX-1 Forward Primer

<400> SEQUENCE: 5
ggatgaagtc taccaaagct cacgc                                     25

<210> SEQ ID NO 6
<211> LENGTH: 26
<212> TYPE: DNA
<213> ORGANISM: Artificial Sequence
<220> FEATURE:
```

<223> OTHER INFORMATION: PDX-1 Reverse Primer

<400> SEQUENCE: 6
ccagatcttg atgtgttctc tcggtc                                          26

<210> SEQ ID NO 7
<211> LENGTH: 20
<212> TYPE: DNA
<213> ORGANISM: Artificial Sequence
<220> FEATURE:
<223> OTHER INFORMATION: Ngn3 Forward Primer

<400> SEQUENCE: 7
caatcgaatg cacaacctca                                                 20

<210> SEQ ID NO 8
<211> LENGTH: 20
<212> TYPE: DNA
<213> ORGANISM: Artificial Sequence
<220> FEATURE:
<223> OTHER INFORMATION: Ngn3 Reverse Primer

<400> SEQUENCE: 8
gggagactgg ggagtagagg                                                 20

<210> SEQ ID NO 9
<211> LENGTH: 23
<212> TYPE: DNA
<213> ORGANISM: Artificial Sequence
<220> FEATURE:
<223> OTHER INFORMATION: GLUT2 Forward Primer

<400> SEQUENCE: 9
aggacttctg tggaccttat gtg                                             23

<210> SEQ ID NO 10
<211> LENGTH: 20
<212> TYPE: DNA
<213> ORGANISM: Artificial Sequence
<220> FEATURE:
<223> OTHER INFORMATION: GLUT2 Reverse Primer

<400> SEQUENCE: 10
gttcatgtca aaagcaggg                                                  20

<210> SEQ ID NO 11
<211> LENGTH: 22
<212> TYPE: DNA
<213> ORGANISM: Artificial Sequence
<220> FEATURE:
<223> OTHER INFORMATION: GKS Forward Primer

<400> SEQUENCE: 11
aagaaggtga tgagacggat gc                                              22

<210> SEQ ID NO 12
<211> LENGTH: 22
<212> TYPE: DNA
<213> ORGANISM: Artificial Sequence
<220> FEATURE:
<223> OTHER INFORMATION: GKS Reverse Primer

<400> SEQUENCE: 12
catctggtgt ttggtcttca cg                                              22

```
<210> SEQ ID NO 13
<211> LENGTH: 28
<212> TYPE: DNA
<213> ORGANISM: Artificial Sequence
<220> FEATURE:
<223> OTHER INFORMATION: SUR1 Forward Primer

<400> SEQUENCE: 13
gtgcacatcc accacagcac atggcttc                                    28

<210> SEQ ID NO 14
<211> LENGTH: 28
<212> TYPE: DNA
<213> ORGANISM: Artificial Sequence
<220> FEATURE:
<223> OTHER INFORMATION: SUR1 Reverse Primer

<400> SEQUENCE: 14
gtgtcttgaa gaagatgtat ctcctcac                                    28

<210> SEQ ID NO 15
<211> LENGTH: 21
<212> TYPE: DNA
<213> ORGANISM: Artificial Sequence
<220> FEATURE:
<223> OTHER INFORMATION: Kir6.2 Forward Primer

<400> SEQUENCE: 15
cgctggtgga cctcaagtgg c                                           21

<210> SEQ ID NO 16
<211> LENGTH: 22
<212> TYPE: DNA
<213> ORGANISM: Artificial Sequence
<220> FEATURE:
<223> OTHER INFORMATION: Kir6.2 Reverse Primer

<400> SEQUENCE: 16
cctcggggct ggtggtcttg cg                                          22

<210> SEQ ID NO 17
<211> LENGTH: 30
<212> TYPE: DNA
<213> ORGANISM: Artificial Sequence
<220> FEATURE:
<223> OTHER INFORMATION: Insulin (RAT) Forward Primer

<400> SEQUENCE: 17
ccctctagac cggctgagct aagaatccag                                  30

<210> SEQ ID NO 18
<211> LENGTH: 35
<212> TYPE: DNA
<213> ORGANISM: Artificial Sequence
<220> FEATURE:
<223> OTHER INFORMATION: Insulin (RAT) Reverse Primer

<400> SEQUENCE: 18
ggcgaccggt gcgggagtta ctgggtctcc actag                            35
```